United States Patent
Nagao et al.

(10) Patent No.: US 11,149,198 B2
(45) Date of Patent: *Oct. 19, 2021

(54) FIBER LIGHT SOURCE INCLUDING PHOSPHOR

(71) Applicant: Panasonic Intellectual Property Management Co., Ltd., Osaka (JP)

(72) Inventors: Nobuaki Nagao, Gifu (JP); Mitsuru Nitta, Kyoto (JP); Yasuhisa Inada, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 588 days.

This patent is subject to a terminal disclaimer.

(21) Appl. No.: 15/933,606

(22) Filed: Mar. 23, 2018

(65) Prior Publication Data

US 2018/0216002 A1    Aug. 2, 2018

Related U.S. Application Data

(63) Continuation-in-part of application No. PCT/JP2017/019466, filed on May 25, 2017, which is
(Continued)

(30) Foreign Application Priority Data

Jul. 4, 2016 (JP) .............................. JP2016-132126
Feb. 16, 2017 (JP) .............................. JP2017-026910
Feb. 27, 2017 (JP) .............................. JP2017-035537

(51) Int. Cl.
*C09K 11/77* (2006.01)
*F21V 9/30* (2018.01)
(Continued)

(52) U.S. Cl.
CPC ........ *C09K 11/7774* (2013.01); *A61B 1/0653* (2013.01); *A61B 1/0684* (2013.01);
(Continued)

(58) Field of Classification Search
CPC ..... C90K 11/7774; F21V 9/30; A61B 1/0653; A61B 1/0684; A61B 1/07; C09K 11/0883; C09K 11/62
See application file for complete search history.

(56) References Cited

U.S. PATENT DOCUMENTS 4,507,585 A * 3/1985 Inoue ...................... H01J 29/34
313/471
4,809,291 A * 2/1989 Byer ...................... H01S 3/109
372/21

(Continued)

FOREIGN PATENT DOCUMENTS

CN    101220272 A    7/2008
CN    102361956 A    2/2012
(Continued)

OTHER PUBLICATIONS

International Search Report of PCT application No. PCT/JP2017/019464 dated Jun. 27, 2017.
(Continued)

*Primary Examiner* — Alexandra L Newton
*Assistant Examiner* — Jae Woo
(74) *Attorney, Agent, or Firm* — McDermott Will and Emery LLP

(57) ABSTRACT

A fiber light source includes a solid-state light source, a wavelength convertor, and an optical fiber. The solid-state light source is configured to emit first light, the first light including blue light with a peak wavelength in a range of 430 to 470 nm, inclusive, and green light with a peak wavelength in a range of 480 to 550 nm, inclusive. The
(Continued)

wavelength convertor is disposed on the light output side or the light incident side of the optical fiber and contains a red phosphor. The red phosphor includes Ce as a luminescent center, and is excited by at least part of the green light to emit second light. The second light has a spectrum with a peak wavelength in a range of 600 to 700 nm, inclusive. The red phosphor contains a nitride or an oxynitride as a host material.

24 Claims, 32 Drawing Sheets

Related U.S. Application Data a continuation-in-part of application No. PCT/JP2017/000935, filed on Jan. 13, 2017.

(51) Int. Cl.

| | | |
|---|---|---|
| A61B 1/06 | (2006.01) | |
| A61B 1/07 | (2006.01) | |
| H01S 5/02251 | (2021.01) | |
| H01S 5/02253 | (2021.01) | |
| C09K 11/08 | (2006.01) | |
| C09K 11/62 | (2006.01) | |
| F21V 8/00 | (2006.01) | |
| H01S 3/00 | (2006.01) | |
| H01S 3/16 | (2006.01) | |
| H01S 3/23 | (2006.01) | |
| H01S 5/30 | (2006.01) | |
| H04N 5/225 | (2006.01) | |
| H04N 9/04 | (2006.01) | |
| F21W 131/105 | (2006.01) | |
| H01S 5/00 | (2006.01) | |

(52) U.S. Cl.
CPC ............ *A61B 1/07* (2013.01); *C09K 11/0883* (2013.01); *C09K 11/62* (2013.01); *F21V 9/30* (2018.02); *G02B 6/0006* (2013.01); *G02B 6/0008* (2013.01); *H01S 3/005* (2013.01); *H01S 3/1611* (2013.01); *H01S 3/1643* (2013.01); *H01S 3/23* (2013.01); *H01S 5/02251* (2021.01); *H01S 5/02253* (2021.01); *H01S 5/3013* (2013.01); *H04N 5/2256* (2013.01); *H04N 9/045* (2013.01); *F21W 2131/105* (2013.01); *H01S 5/0087* (2021.01); *H04N 2005/2255* (2013.01)

(56) References Cited

U.S. PATENT DOCUMENTS

| | | | | |
|---|---|---|---|---|
| 5,202,891 A * | 4/1993 | Sleight | ................ | G02F 1/3551 |
| | | | | 359/328 |
| 5,246,804 A * | 9/1993 | Furukawa | ................ | G03F 1/72 |
| | | | | 356/237.5 |
| 6,228,286 B1 * | 5/2001 | Leblans | ............... | C09K 11/615 |
| | | | | 250/362 |
| 6,569,156 B1 * | 5/2003 | Tankovich | ........... | A61B 18/203 |
| | | | | 606/10 |
| 7,094,362 B2 * | 8/2006 | Setlur | ................ | C09K 11/7774 |
| | | | | 252/301.4 F |
| 8,337,400 B2 * | 12/2012 | Mizuyoshi | ........... | A61B 1/0638 |
| | | | | 600/178 |
| 8,491,816 B2 * | 7/2013 | Hong | ................ | C09K 11/675 |
| | | | | 252/301.4 H |
| 8,790,253 B2 * | 7/2014 | Sunagawa | .......... | A61B 1/0638 |
| | | | | 362/227 |
| 8,858,429 B2 * | 10/2014 | Mizuyoshi | ........... | A61B 1/0653 |
| | | | | 600/118 |
| 9,062,253 B2 | 6/2015 | Won et al. | | |
| 9,526,408 B2 * | 12/2016 | Yamaguchi | ........ | A61B 1/00004 |
| 9,725,648 B2 | 8/2017 | Izawa et al. | | |
| 10,026,876 B2 | 7/2018 | Hosokawa et al. | | |
| 10,411,170 B2 * | 9/2019 | Tragl | ................ | H01L 33/50 |
| 2004/0145308 A1 * | 7/2004 | Rossner | ............ | C09K 11/7774 |
| | | | | 313/512 |
| 2005/0117334 A1 * | 6/2005 | Lee | ................ | H01L 25/0753 |
| | | | | 362/231 |
| 2005/0242329 A1 | 11/2005 | Fiedler et al. | | |
| 2006/0043879 A1 | 3/2006 | Naitou | | |
| 2006/0197098 A1 | 9/2006 | Aihara | | |
| 2007/0126011 A1 | 6/2007 | Lee | | |
| 2007/0159066 A1 | 7/2007 | Cheetham et al. | | |
| 2007/0263678 A1 | 11/2007 | Mizuuchi et al. | | |
| 2008/0150412 A1 | 6/2008 | Yoshimatsu | | |
| 2008/0262316 A1 * | 10/2008 | Ajima | ................. | A61B 1/0669 |
| | | | | 600/178 |
| 2009/0066230 A1 | 3/2009 | Hirosaki et al. | | |
| 2009/0167149 A1 * | 7/2009 | Ito | ........................ | G02B 6/0003 |
| | | | | 313/501 |
| 2009/0312607 A1 * | 12/2009 | Sunagawa | ............ | A61B 5/0071 |
| | | | | 600/160 |
| 2010/0085728 A1 | 4/2010 | Seto et al. | | |
| 2011/0198651 A1 * | 8/2011 | Chen | ................ | C09K 11/7772 |
| | | | | 257/98 |
| 2012/0242912 A1 | 9/2012 | Kitano | | |
| 2012/0256533 A1 | 10/2012 | Seto et al. | | |
| 2012/0300178 A1 * | 11/2012 | Sugiyama | ........... | H04N 9/3164 |
| | | | | 353/31 |
| 2012/0302847 A1 * | 11/2012 | Ozawa | ................ | A61B 1/0638 |
| | | | | 600/339 |
| 2013/0147343 A1 | 6/2013 | Won et al. | | |
| 2013/0234588 A1 * | 9/2013 | Seto | ................... | C09K 11/7706 |
| | | | | 313/503 |
| 2014/0131748 A1 * | 5/2014 | Song | ................... | H01L 25/0753 |
| | | | | 257/89 |
| 2014/0185282 A1 | 7/2014 | Hsu et al. | | |
| 2014/0264402 A1 * | 9/2014 | Mei | ........................ | F21K 9/64 |
| | | | | 257/89 |
| 2014/0285772 A1 | 9/2014 | Tajiri | | |
| 2016/0150200 A1 | 5/2016 | Saka et al. | | |
| 2016/0276549 A1 * | 9/2016 | Yamashita | ............ | H05B 47/10 |
| 2016/0330806 A1 * | 11/2016 | Yamashita | ............ | H05B 45/20 |
| 2017/0263592 A1 * | 9/2017 | Schmidt | ................ | C09K 11/02 |
| 2017/0307163 A1 | 10/2017 | Nagasaki et al. | | |
| 2017/0331012 A1 * | 11/2017 | Heidemann | ........ | C09K 11/7731 |
| 2017/0343188 A1 | 11/2017 | Oshio et al. | | |
| 2018/0002188 A1 * | 1/2018 | Nitta | ........................ | F21S 41/16 |
| 2018/0212112 A1 * | 7/2018 | Nitta | ........................ | H01L 33/62 |
| 2018/0346808 A1 * | 12/2018 | Nitta | ................... | C09K 11/7769 |
| 2019/0171093 A1 * | 6/2019 | Furuyama | ........... | G02B 5/0226 |
| 2019/0177614 A1 * | 6/2019 | Nagao | ................ | C09K 11/7766 |

FOREIGN PATENT DOCUMENTS

| | | |
|---|---|---|
| CN | 102543986 A | 7/2012 |
| CN | 103148395 A | 6/2013 |
| CN | 103254900 A | 8/2013 |
| CN | 103715342 A | 4/2014 |
| EP | 2610217 A1 | 7/2013 |
| JP | 2005-167177 | 6/2005 |
| JP | 2006-008721 | 1/2006 |
| JP | 2006-073656 | 3/2006 |
| JP | 2006-245443 A | 9/2006 |
| JP | 2007-158296 | 6/2007 |
| JP | 2007-515527 A | 6/2007 |
| JP | 2007-231245 A | 9/2007 |
| JP | 2008-088362 | 4/2008 |
| JP | 2008-177484 A | 7/2008 |
| JP | 2008-285659 A | 11/2008 |
| JP | 2009-512741 A | 3/2009 |
| JP | 2009-153712 | 7/2009 |
| JP | 2009-189473 A | 8/2009 |
| JP | 2009-249445 A | 10/2009 |
| JP | 4729480 B2 | 7/2011 |
| JP | 2011-526066 A | 9/2011 |
| JP | 2012-114040 A | 6/2012 |

(56) References Cited

FOREIGN PATENT DOCUMENTS

| | | |
|---|---|---|
| JP | 2012-212129 A | 11/2012 |
| JP | 2014-224230 A | 12/2014 |
| JP | 2016-028124 A | 2/2016 |
| JP | 2016-104232 A | 6/2016 |
| KR | 10-2010-0010922 A | 2/2010 |
| WO | 2007/041563 A2 | 4/2007 |
| WO | 2009/157999 A1 | 12/2009 |
| WO | 2015/025570 A1 | 2/2015 |
| WO | 2016/092743 A1 | 6/2016 |

OTHER PUBLICATIONS

International Search Report of PCT application No. PCT/JP2017/019465 dated Aug. 22, 2017.
International Search Report of PCT application No. PCT/JP2017/019467 dated Aug. 22, 2017.
Yun-Chen Wu et al., "a-(Y,Gd)Fs:Ce3+: a novel red-emitting fluorosulfide phosphor for solid-state lighting", Journal of Materials Chemistry, 21, Oct. 21, 2011, pp. 15163-15166.
The Extended European Search Report dated Jun. 27, 2019 for the related European Patent Application No. 17823889.5.
The Extended European Search Report dated Jun. 28, 2019 for the related European Patent Application No. 17823890.3.
The Extended European Search Report dated Jun. 28, 2019 for the related European Patent Application No. 17823891.1.
The Extended European Search Report dated Jul. 2, 2019 for the related European Patent Application No. 17780614.8.
The Extended European Search Report dated Jun. 27, 2019 for the related European Patent Application No. 17734219.3.
Lihong Liu et al: "Yellow-Emitting Y3Si6N11: Ce3+ Phosphors for White Light-Emitting Diodes (LEDs)", Journal of the American Ceramic Society., vol. 96, No. 6, Jun. 1, 2013 (Jun. 1, 2013), pp. 1688-1690,XP055450326.
Database WPI Week 201372 Thomson Scientific, London, GB; AN 2013-R71607, XP002792144.
International Search Report of PCT application No. PCT/JP2017/019466 dated Aug. 22, 2017.
International Search Report of PCT application No. PCT/JP2017/000935 dated Mar. 7, 2017.
Yongchao Jia et al., "First-principles study of Ce3+-F-doped lanthanum silicate nitride phosphors: Neutral excitation, Stokes shift, and luminescent center identification", Physical Review B93, 155111, Apr. 6, 2016.
R. Le Toquin et al., "Red-emitting cerium-based phosphor materials for solid-state lighting applications", Chemical Physics Letters, vol. 423, Issues4-6, Jun. 1, 2006, pp. 352-356.
Qiang-Qiang Zhu et al., "Extra-Broad Band Orange-Emitting Ce3+-Doped Y3Si5N9O Phosphor for Solid-State Lighting: Electronic, Crystal Structures and Luminescence Properties", Chemistry of Materials, vol. 28, Jun. 20, 2016, pp. 4829-4839.
Notice of Allowance issued in U.S. Appl. No. 15/636,747, dated Oct. 17, 2018.
Non-Final Office Action issued in U.S. Appl. No. 15/723,240, dated May 1, 2020.
English Translation of Chinese Search Report dated May 8, 2020 for the related Chinese Patent Application No. 201780002095.2.
English Translation of Chinese Search Report dated May 8, 2020 for the related Chinese Patent Application No. 201780002084.4.
Non-Final Office Action issued in U.S. Appl. No. 15/933,455, dated Sep. 5, 2019.
Notice of Allowance issued in U.S. Appl. No. 15/933,455, dated Mar. 10, 2020.
Non-Final Office Action issued in U.S. Appl. 15/933,624, dated Jul. 9, 2020.
Non-Final Office Action issued in U.S. Appl. No. 16/245,101, dated Oct. 31, 2019.
Notice of Allowance issued in U.S. Appl. No. 16/245,101, dated Mar. 13, 2020.
English Translation of Chinese Search Report dated Jan. 27, 2021 for the related Chinese Patent Application No. 201780002095.2.
English Translation of Chinese Search Report dated Jan. 27, 2021 for the related Chinese Patent Application No. 201780002084.4.
English Translation of Chinese Search Report dated Jan. 6, 2021 for the related Chinese Patent Application No. 201780002085.9.
English Translation of Chinese Search Report dated Jun. 2, 2021 for the related Chinese Patent Application No. 201780001107.X.
English Translation of Chinese Search Report dated Jun. 3, 2021 for the related Chinese Patent Application No. 201780000449.X.
"Effect of Y3+ on the local structure and luminescent properties of La3-xYxSi6N11:Ce3+ phosphors for high power LED lighting," Fu Du et al. , RSC Adv , Aug. 9, 2016, vol. 6, pp. 77059-77065.
"Effect of Al/Si substitution on the structure and luminescence properties of CaSrSiO4:Ce3+ phosphors: analysis based an the polyhedral distortion," Shihai Miao et al., Journal of Materials Chemistry C, May 14, 2015, vol. 3, No. 18, pp. 4616-4622.

* cited by examiner

FIBER LIGHT SOURCE INCLUDING PHOSPHOR

BACKGROUND

1. Technical Field

The present disclosure relates to a fiber light source including a phosphor.

2. Description of the Related Art

In recent years, solid-state light sources, such as white light-emitting diodes (LEDs) and laser-excited light sources, have been widely used. Existing typical white LEDs include a combination of a blue LED chip, which is a blue light-emitting device, and a phosphor. In such typical white LEDs, light from a blue LED chip is partly subjected to color conversion with a phosphor, and blue light from the blue LED chip and light from the phosphor are mixed to produce white light. In more recent years, high-power white-light-emitting apparatuses including a combination of a laser diode (LD) and a phosphor have been developed. At present, white solid-state light sources mainly include a combination of a blue LED chip or a blue LD and a yellow phosphor. In order to improve color rendering properties and color reproducibility or in order to produce low-color-temperature white, white light sources including a red phosphor in addition to a blue light source and a yellow phosphor are being developed.

Yellow phosphors including Ce as a luminescent center, such as the phosphor represented by the general formula $Y_3Al_5O_{12}:Ce^{3+}$ (hereinafter abbreviated to YAG:Ce) or with the general formula $La_3Si_6N_{11}:Ce^{3+}$ (hereinafter abbreviated to LSN:Ce) described in Japanese Patent No. 4459941, are known. Also known are red phosphors including Eu as a luminescent center, such as the phosphor represented by the general formula $(Sr,Ca)AlSiN_3:Eu^{2+}$ (hereinafter abbreviated to CASN:Eu) described in Japanese Patent No. 3837588.

Such a light-emitting apparatus including a combination of a solid-state light source, such as a LD, and a phosphor is compact and has high power, and is therefore also utilized as a fiber light source for use in endoscopes. For example, Japanese Unexamined Patent Application Publication No. 2009-153712 discloses a fiber light source that includes first and second semiconductor light sources, which emit light in different wavelength regions, a wavelength converter containing a phosphor, and an optical fiber. The phosphor in the wavelength converter absorbs light emitted from the first semiconductor light source and emits light in a wavelength region different from that of light emitted from the first and second semiconductor light sources. The fiber light source disclosed in Japanese Unexamined Patent Application Publication No. 2009-153712 can turn on and off the light sources to change the color of output light.

SUMMARY

One non-limiting and exemplary embodiment provides a fiber light source in which the power and color controllability can be improved.

In one general aspect, the techniques disclosed here feature a fiber light source that includes a solid-state light source, a wavelength convertor, and an optical fiber. The solid-state light source emits first light, the first light including blue light with a peak wavelength in a range of 430 to 470 nm, inclusive, and green light with a peak wavelength in a range of 480 to 550 nm, inclusive. The wavelength convertor is disposed on the light output side or the light incident side of the optical fiber and contains a red phosphor. The red phosphor includes Ce as a luminescent center, and is excited by at least part of the green light to emit second light. The second light has a spectrum with a peak wavelength in a range of 600 to 700 nm, inclusive. The red phosphor contains a nitride or an oxynitride as a host material.

According to a fiber light source of the present disclosure, the power and color controllability can be improved.

It should be noted that general or specific embodiments of the present disclosure may be implemented as a light source, an endoscope, a phosphor, a device, an apparatus, a system, a vehicle, a method, or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

Figure 1A:
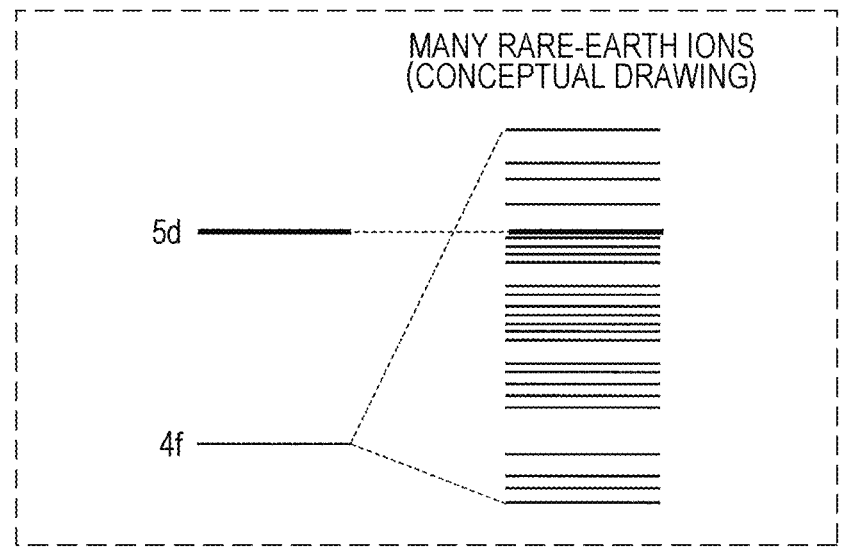
FIG. 1A is a schematic view of splitting of the 4f orbital and the 5d orbital of rare-earth ions.

DETAILED DESCRIPTION (Underlying Knowledge Forming Basis of the Present Disclosure)

A white-light-emitting apparatus including a combination of a phosphor and a solid-state light source, such as LD, may be any of the following apparatus.

A first apparatus is a pseudo white light source including a combination of a blue LED and a yellow phosphor YAG:Ce. A light-emitting apparatus of this type is widely used because of its lower power consumption and high drive controllability of the LED. Only having two color components, however, such a white light source cannot produce warm light, for example, of the incandescent lamp color, and has poor color controllability.

A second apparatus is a white light source including a combination of a blue LED, a yellow phosphor YAG:Ce, and a red phosphor CASN:Eu. A light-emitting apparatus of this type can produce white composed of three color components and can control the light intensity of each color component to produce any white light. Thus, a light-emitting apparatus of this type has higher color controllability than light-emitting apparatuses with two color components as described above. The yellow phosphor YAG:Ce used in such a light-emitting apparatus has high emission quantum efficiency, and has almost constant emission quantum efficiency even when excited by a high-power blue LED or blue LD. By contrast, the red phosphor CASN:Eu has a problem of decreased emission quantum efficiency when excited by high-power light and is therefore used only in relatively low power light sources. This is because phosphors including Eu as a luminescent center have a longer emission lifetime than phosphors including Ce as a luminescent center and therefore tends to reach luminance saturation during high-energy excitation. Thus, no high-power color-controllable white light source has been developed.

For example, in order to increase the probability of finding a diseased tissue, there is a demand for a fiber light source for use in endoscopes that can emit high-power white light. A diseased tissue is identified using light with a wavelength appropriate for each lesion. In order to increase the probability of finding a diseased tissue, therefore, it is also important for a fiber light source for use in endoscopes to have high color controllability.

The present inventors have extensively studied to develop a high-power color-controllable fiber light source that can emit white light.

(Summary of Aspect of the Present Disclosure)

A fiber light source according to a first aspect of the present disclosure includes a solid-state light source, a wavelength convertor, and an optical fiber. The solid-state light source emits first light, the first light including blue light with a peak wavelength in a range of 430 to 470 nm, inclusive, and green light with a peak wavelength in a range of 480 to 550 nm, inclusive. The wavelength convertor is disposed on the light output side or the light incident side of the optical fiber and contains a red phosphor. The red phosphor includes Ce as a luminescent center, and is excited by at least part of the green light to emit second light. The second light has a spectrum with a peak wavelength in a range of 600 to 700 nm, inclusive. The red phosphor contains a nitride or an oxynitride as a host material.

The fiber light source according to the first aspect contains the red phosphor including the Ce luminescent center. The red phosphor is excited by green light with high absorption efficiency, and therefore the fiber light source can produce high power. Furthermore, white light emitted from the fiber light source according to the first aspect is composed of blue light and green light emitted from the solid-state light source and red light emitted from the red phosphor, and it is therefore easy to control the color of the white light. Thus, the fiber light source according to the first aspect has high power and high color controllability.

In a second aspect, for example, the peak wavelength of the green light in the fiber light source according to the first aspect may be in a range of 510 to 540 nm, inclusive.

In the red phosphor, a longer wavelength of excitation light (i.e., green light emitted from a solid-state light source) results in a smaller energy conversion loss (e.g., Stokes' loss) of the phosphor and higher energy conversion efficiency. Thus, the fiber light source according to the second aspect can produce high power because the peak wavelength of the green light is 510 nm or more.

In a third aspect, for example, the wavelength convertor of the fiber light source according to the first or second aspect may include a first phosphor layer containing the red phosphor and a second phosphor layer containing a phosphor different from the red phosphor.

The fiber light source according to the third aspect has higher color controllability because the wavelength convertor contains the second phosphor different from the red phosphor.

In a fourth aspect, for example, the excitation efficiency of the red phosphor of the fiber light source according to the third aspect may be lower for the blue light than for the green light. The second phosphor may be excited by at least part of the blue light. The first phosphor layer may be closer to a light incident side of the wavelength converter than the second phosphor layer.

In the fiber light source according to the fourth aspect, the first phosphor layer disposed on the light incident side contains a red phosphor including Ce as a luminescent center. The excitation efficiency of the red phosphor is lower for blue light than for green light. Thus, in the fiber light source according to the fourth aspect, the second phosphor in the second phosphor layer can be efficiently excited by blue excitation light.

In a fifth aspect, for example, the second phosphor of the fiber light source according to the third or fourth aspect may be at least one selected from the group consisting of a yellow phosphor and a green phosphor.

The fiber light source according to the fifth aspect has higher color controllability due to the yellow phosphor and/or the green phosphor in the second phosphor layer. For example, the yellow phosphor has an emission peak wavelength in a range of 560 to 600 nm, inclusive. For example, the green phosphor has an emission peak wavelength of 500 nm or more and less than 560 nm.

In a sixth aspect, for example, the solid-state light source of the fiber light source according to at least one aspect of the first to fifth aspects may include a GaN semiconductor laser.

The fiber light source according to the sixth aspect can produce high power by using the GaN semiconductor laser.

In a seventh aspect, for example, the GaN semiconductor laser of the fiber light source according to the sixth aspect may emit the blue light. The solid-state light source may further include a YAG:Nd solid-state laser that emits the green light and that includes a second harmonic generator.

The fiber light source according to the seventh aspect can produce high power by using the GaN semiconductor laser and the YAG:Nd solid-state laser.

In an eighth aspect, for example, each of all phosphors in the wavelength convertor of the fiber light source according to at least one aspect of the first to seventh aspects may have a lie afterglow value of not more than 100 ns.

All phosphors in the fiber light source according to the eighth aspect have good luminance saturation characteristics and can have high quantum efficiency even at high power. Thus, the fiber light source according to the eighth aspect can have high quantum efficiency and color reproducibility even at high power.

In a ninth aspect, for example, the red phosphor of the fiber light source according to at least one aspect of the first to eighth aspects may contain a host material, the host material containing Y or a lanthanoid element other than Ce.

The red phosphor in the fiber light source according to the ninth aspect contains a host material, the host material containing Y or a lanthanoid element other than Ce. Ions of the lanthanoid element other than Ce and Y have the same valence as $Ce^{3+}$. Furthermore, the ionic radii of the lanthanoid element other than Ce and Y are relatively close to the ionic radius of $Ce^{3+}$. Thus, the host material can stably take $Ce^{3+}$ into its crystal structure. Thus, the fiber light source according to the ninth aspect containing the red phosphor can have high luminous efficiency.

In a tenth aspect, for example, the red phosphor of the fiber light source according to at least one aspect of the first to ninth aspects may contain a nitride or an oxynitride as a host material. Or, the red phosphor may contain an oxide as a host material.

A nitride or an oxynitride has high thermal conductivity and is less likely to become hot. Thus, the fiber light source according to the tenth aspect can reduce the decrease in luminous efficiency of the phosphor caused by temperature quenching.

In an eleventh aspect, for example, the red phosphor of the fiber light source according to at least one aspect of the first to tenth aspects may contain a host material having a tetragonal crystal structure.

In a twelfth aspect, for example, the red phosphor of the fiber light source according to at least one aspect of the first to eleventh aspects may contain a crystal phase having the chemical composition $Ce_xM_{3-x-y}\beta_{6}\gamma_{11-z}$, wherein M denotes one or two or more elements selected from the group consisting of Sc, Y, La, Pr, Nd, Sm, Eu, Gd, Tb, Dy, Ho, Er, Tm, Yb, and Lu, β includes Si in an amount of not less than 50% by mole of a total amount of Si, γ includes N in an amount of not less than 80% by mole of a total amount of N, and x, y and z satisfy 0<x≤0.6, 0≤y≤1.0, and 0≤z≤1.0.

The fiber light source according to the twelfth aspect can have higher quantum efficiency than known fiber light sources at high power. Furthermore, when used as a white-light-emitting apparatus, the fiber light source according to the twelfth aspect can exhibit good color rendering properties and color reproducibility.

In a thirteenth aspect, for example, the red phosphor of the fiber light source according to the twelfth aspect may contain a crystal phase having the chemical composition $Ce_xM_{3-x}Si_{6-q}Al_qN_{11-z}$, wherein q satisfies 0≤q≤2.0. In other words, β in the chemical composition of the twelfth aspect may be Si or Si and Al.

The fiber light source according to the thirteenth aspect can have higher quantum efficiency than known fiber light sources at high power. Furthermore, when used as a white-light-emitting apparatus, the fiber light source according to the thirteenth aspect can exhibit good color rendering properties and color reproducibility.

In a fourteenth aspect, for example, the red phosphor of the fiber light source according to the thirteenth aspect may contain a crystal phase having the chemical composition $Ce_xLa_{3-z}Si_{6-q}Al_qN_{11-z}$. In other words, in the chemical composition of the thirteenth aspect, M may be La, and 0<q.

The fiber light source according to the fourteenth aspect can have higher quantum efficiency than known fiber light sources at high power. Furthermore, when used as a white fiber light source, the fiber light source according to the fourteenth aspect can exhibit good color rendering properties and color reproducibility.

In a fifteenth aspect, for example, the red phosphor of the fiber light source according to the thirteenth aspect may contain a crystal phase having the chemical composition $Ce_xY_pLa_{3-x-p}Si_6N_{11}$, wherein (1.5-x)≤p≤(3-x). In other words, in the chemical composition of the thirteenth aspect, β may be Si, and M may be Y and La.

The fiber light source according to the fifteenth aspect can have higher quantum efficiency than known fiber light sources at high power. Furthermore, when used as a white-light-emitting apparatus, the fiber light source according to the fifteenth aspect can exhibit good color rendering properties and color reproducibility.

In a sixteenth aspect, for example, the wavelength convertor of the fiber light source according to at least one aspect of the first to fifteenth aspects may further contain a phosphor containing a garnet crystal including Ce as a luminescent center. The phosphor may be a green phosphor or a yellow-green phosphor. Examples of the yellow-green phosphor include a yellow phosphor and a green phosphor.

Containing at least two phosphors having different emission wavelengths, the fiber light source according to the sixteenth aspect can control emission color. The phosphors for use in the fiber light source according to the sixteenth aspect have good luminance saturation characteristics. Thus, the fiber light source according to the sixteenth aspect can have high quantum efficiency even at high power.

In a seventeenth aspect, for example, in the fiber light source according to at least one aspect of the first to sixteenth aspects, the solid-state light source may include a blue laser that emits the blue light and a green laser that emits the green light, and the fiber light source may further include a dichroic mirror by which the blue light and the green light are coaxially multiplexed to be incident on the optical fiber.

The fiber light source according to the seventeenth aspect can coaxially multiplex excitation lights to facilitate alignment correction of emission spots of phosphors and can reduce useless stray light.

In an eighteenth aspect, for example, the fiber light source according to at least one aspect of the first to seventeenth aspects may further include a coupler lens that is disposed on the light incident side of the optical fiber and enables light to be incident on the optical fiber.

In a nineteenth aspect, for example, the wavelength convertor in the fiber light source according to at least one aspect of the first to eighteenth aspects may be disposed on the light output side of the optical fiber and may receive the first light from the solid-state light source through the optical fiber.

In a twentieth aspect, for example, the fiber light source according to the nineteenth aspect may further include a condenser lens disposed on an optical path between a light output end of the optical fiber and the wavelength convertor, and an objective lens disposed on a light output side of the wavelength convertor.

In a twenty-first aspect, for example, the fiber light source according to at least one aspect of the first to eighteenth aspects, the wavelength convertor may be disposed on the light incident side of the optical fiber, and the fiber light source may further include a condenser lens disposed on an optical path between the wavelength convertor and a light incident end of the optical fiber, and an objective lens disposed on the light output side of the optical fiber.

In the fiber light source according to the twenty-first aspect, the wavelength convertor is disposed on the light incident side of the optical fiber. Thus, for example, when used in an endoscope, the fiber light source according to the twenty-first aspect can reduce heat transfer from the wavelength convertor to the body and improve safety.

An endoscope according to a twenty-second aspect of the present disclosure includes the fiber light source according to any one aspect of the first to twenty-first aspects, and an image sensor for outputting an electric signal depending on the amount of light received, the light being emitted from the fiber light source and reflected by an object.

The endoscope according to the twenty-second aspect includes a high-power color-controllable fiber light source. Thus, the twenty-second aspect of the present disclosure can provide an endoscope suitable to identify a diseased tissue.

In a twenty-third aspect, for example, the endoscope according to the twenty-second aspect may include an enlongated insert, wherein at least a light output portion of the fiber light source and the image sensor may be disposed in the insert.

In a twenty-fourth aspect, for example, the endoscope according to the twenty-second or twenty-third aspect may further include an optical system that faces an imaging plane of the image sensor and converges light reflected from the object onto the imaging plane.

An endoscope system according to a twenty-fifth aspect of the present disclosure includes the endoscope according to any one aspect of the twenty-second to twenty-fourth aspects, a processing apparatus that is electrically connected to the image sensor and outputs an image signal based on the electric signal, and a display unit that is electrically connected to the processing apparatus and displays an image based on the image signal.

The twenty-fifth aspect of the present disclosure can provide an endoscope system with an endoscope suitable to identify a diseased tissue.

Embodiments of the Present Disclosure

The embodiments of the present disclosure will be described in detail below. It goes without saying that the present disclosure is not limited to these embodiments, and these embodiments may be modified within the technical scope of the present disclosure. The same or substantially the same constituents are denoted by the same reference numerals and letters and will not be described again.

First Embodiment

A first embodiment describes an embodiment of a fiber light source according to the present disclosure.

The fiber light source of the first embodiment includes a solid-state light source, a wavelength convertor, which converts the wavelength of output light emitted from the solid-state light source, and an optical fiber. The solid-state light source emits at least blue light and green light. The wavelength convertor contains at least a red phosphor including Ce as a luminescent center. The red phosphor has an emission spectrum with a peak wavelength in the range of 600 to 700 nm. The blue light has a peak wavelength in the range of 430 to 470 nm. The green light has a peak wavelength in the range of 480 to 550 nm, desirably 510 to 540 nm. The red phosphor has an emission peak wavelength in the range of 600 to 700 nm.

The red phosphor including the Ce luminescent center for use in the fiber light source according to the first embodiment (hereinafter also referred to as the "red phosphor in the first embodiment") will be described below.

The red phosphor in the first embodiment contains a host material and Ce as the luminescent center. The host material may contain Y or a lanthanoid element other than Ce. The host material may be a nitride or an oxynitride. The host material may have a tetragonal crystal structure. Furthermore, the host material may contain an oxide or may be an oxide. Sulfide phosphors are likely to be hydrolyzed and produce hydrogen sulfide. Thus, it is difficult to use sulfide phosphors from a practical standpoint. By contrast, many oxide, oxynitride, and nitride phosphors are stable in the air. Nitride phosphors require heat treatment in a high-pressure atmosphere and require large-scale facilities. On the other hand, oxides can be synthesized by firing in the air, require a simple synthesis process, and can be produced at low cost.

The red phosphor in the first embodiment may contain a crystal phase having the chemical composition $Ce_xM_{3-x-y}\beta_{6\gamma}11_{-z}$, for example. The red phosphor containing the crystal phase having the chemical composition $Ce_xM_{3-x-y}\beta_{6\gamma}11_{-z}$ is hereinafter also referred to as the red phosphor of a first example in the first embodiment. The variable x satisfies $0<x\le0.6$. Since x is more than 0, Ce can emit light. In order to increase emission intensity, x is desirably 0.0003 or more, more desirably 0.015 or more. The maximum value of x is not particularly limited as long as the phosphor can emit light. However, an excessively large x results in low emission intensity due to concentration quenching. Thus, the decrease in emission intensity can be reduced when x is 0.6 or less. In order to increase emission intensity, x is desirably 0.3 or less, more desirably 0.15 or less.

M denotes one or two or more rare-earth elements other than Ce. More specifically, M denotes one or two or more elements selected from the group consisting of Sc, Y, La, Pr, Nd, Sm, Eu, Gd, Tb, Dy, Ho, Er, Tm, Yb, and Lu. M may contain La in an amount of not less than 90% by mole of a total amount of La. The element group other than La has an ionic radius close to that of La and therefore can occupy the M site.

The variable y satisfies $0\le y\le1.0$. When y is 1.0 or less, the structure of the crystal phase can be stabilized.

$\beta$ includes Si in an amount of not less than 50% by mole of a total amount of Si. More specifically, $\beta$ is Si alone, or includes Si in an amount of equal to or more than 50% by mole and less than 100% by mole and other element(s) in an amount of not more than 50% by mole. For example, $\beta$ may include one or two elements selected from the group consisting of Al and Ga. $(100x/6)\%$ or more by mole of $\beta$ may be the one or two elements. Thus, the amount of the one or two elements in $Ce_xM_{3-x-y}\beta_{6\gamma}11_{-z}$ may be greater than or equal to the amount of Ce. Furthermore, $(300x/6)\%$ or more by mole of $\beta$ may be the one or two elements. Thus, the amount of the one or two elements in $Ce_xM_{3-x-y}\beta_{6\gamma}11_{-z}$ may be at least three times the amount of Ce. $\beta$ may further include other element(s) as long as the phosphor can emit light.

$\gamma$ includes N in an amount of not less than 80% by mole of a total amount of N. More specifically, $\gamma$ is N alone, or includes N in an amount of equal to or more than 80% by mole and less than 100% by mole and other element(s) in an amount of not more than 20% by mole. For example, $\gamma$ may include oxygen (O). For example, substitution of Al (or Ga) at part of the Si sites around Ce or substitution of O at part of the N sites results in low symmetry of a ligand of Ce and emission of light with a longer wavelength.

The variable z satisfies $0\le z\le1.0$. A loss of N (that is, z of more than 0) results in low symmetry of a ligand of Ce and emission of light with a longer wavelength. When z is 1.0 or less, the structure of the crystal phase can be stabilized.

The red phosphor of the first example in the first embodiment has an emission spectrum with the maximum peak in the wavelength range of 600 to 800 nm. The maximum peak herein refers to the peak with the maximum value of the spectrum. A peak of the emission spectrum appears upon excitation at a wavelength of 535 nm, for example.

The red phosphor of the first example in the first embodiment has an excitation spectrum with a first peak in the wavelength range of 500 to 600 nm. The red phosphor of the first example in the first embodiment may have an excitation spectrum with an additional second peak with a wavelength of 350 nm or more and less than 500 nm. The first or second peak may be the maximum peak of the excitation spectrum.

The red phosphor of the first example in the first embodiment may have a 1/e emission lifetime of 100 ns or less. The emission lifetime has an influence on the luminance saturation characteristics. Phosphors containing Eu, such as a known red phosphor CASN:Eu, have a longer emission lifetime than phosphors containing Ce. Thus, phosphors containing Eu are likely to reach luminance saturation due to a decrease in quantum efficiency during high-energy excitation. Thus, the phosphor including the Ce luminescent center of the first embodiment is expected to be a red phosphor with higher quantum efficiency than known red phosphors even at high power.

The crystal phase having the chemical composition $Ce_xM_{3-x-y}\beta_{6y11-z}$ in the red phosphor of the first example in the first embodiment may be a tetragonal crystal. The crystal phase may contain a region with a space group P4bm (#100). The crystal phase of the red phosphor of the first example in the first embodiment may have almost the same crystal structure as a crystal represented by the general formula $La_3Si_6N_{11}$.

The red phosphor of the first example in the first embodiment may have diffraction peaks at (1) 2θ=17.8 to 18.8 degrees, (2) 2θ=26.2 to 27.2 degrees, (3) 2θ=27.2 to 28.2 degrees, (4) 2θ=30.5 to 31.5 degrees, (5) 2θ=32.8 to 33.8 degrees, and (6) 2θ=35.8 to 36.8 degrees in an X-ray diffraction pattern with Cu-Kα radiation. These diffraction peaks may have Miller indices (001), (211), (310), (221), (311), and (410), respectively.

The crystal phase of the red phosphor of the first example in the first embodiment may have the following characteristics in XAFS measurement. In an EXAFS radial distribution function spectrum of the K absorption edge of Ce, the first neighbor shell of Ce may have a lower peak height than the second neighbor shell of Ce. The peak height of the first neighbor shell may be 0.8 to 0.9 times the peak height of the second neighbor shell.

The coordination number of the first neighbor shell of Ce obtained from the EXAFS radial distribution function spectrum of the K absorption edge of Ce may be seven coordination. In this case, for example, the coordination structure around Ce has a nitrogen defect around an A site of La in $La_3Si_6N_{11}$ and may be a coordination structure of seven coordination with low symmetry. A known crystal represented by the general formula $La_3Si_6N_{11}$ has a coordination structure of eight coordination with high symmetry. Thus, in the coordination structure of seven coordination with low symmetry, larger splitting of the 5d orbital and a smaller energy difference between the 5d orbital and the 4f orbital can induce the emission of light with a longer wavelength than before.

The crystal phase may be a crystal phase represented by the chemical composition $Ce_xM_{3-x-y}Si_{6-q}A_qN_{11-z}$, for example, M may denote one or two or more elements selected from the group consisting of Sc, Y, La, Pr, Nd, Sm, Eu, Gd, Tb, Dy, Ho, Er, Tm, Yb, and Lu. A may be one or two elements selected from the group consisting of Al and Ga. The variable x may satisfy $0<x\leq0.6$. The variable y may satisfy $0\leq y\leq1.0$. The variable z may satisfy $0\leq z\leq1.0$. The variable q may satisfy $x\leq q\leq3.0$. When A denotes Al alone, q may satisfy $0\leq q\leq2.0$.

In the red phosphor in the first embodiment, for example, M of the chemical composition $Ce_xM_{3-x}Si_{6-q}Al_qN_{11-z}$ may be La alone. Thus, the red phosphor in the first embodiment may contain a crystal phase having the chemical composition $Ce_xM_{3-x}Si_{6-q}Al_qN_{11-z}$. In this chemical composition, q may satisfy $0<q\leq2.0$.

In the chemical composition $Ce_xM_{3-x}Si_{6-q}Al_qN_{11-z}$ of the red phosphor in the first embodiment, for example, M may be Y alone or Y and La, q may be 0, and z may be 0. Thus, the red phosphor in the first embodiment may contain a crystal phase having the chemical composition $Ce_xY_pLa_{3-p}Si_6N_{11}$. In this chemical composition, p may satisfy $(1.5-x)\leq p\leq(3-x)$.

<Method for Producing Red Phosphor of First Example in First Embodiment>

A method for producing a red phosphor containing the crystal phase represented by the chemical composition $Ce_xM_{3-x-y}Si_{6-q}Si_{6-q}A_qN_{11-z}$ as an example of the red phosphor of the first example in the first embodiment will be described below. In the following description, M denotes La. For example, a compound(s) containing Ce, La, Si, and Al may be used as a raw material. Al may be replaced by Ga. Alternatively, Ce alone, La alone, Si alone, and Al alone may be used as raw materials. Al alone may be replaced by Ga alone. The compound may be a compound that can be converted into a nitride by firing in a nitrogen atmosphere, a high-purity (purity of 99% or more) nitride, or a metal alloy. A small amount of fluoride (such as ammonium fluoride) may be added to promote the reaction.

For example, a Ce compound, a La compound, and a Si compound may be prepared at a chemical composition ratio represented by $Ce_xLa_{3-x-y}Si_6N_{11-z}$ ($0<x\leq0.6$, $0\leq y\leq1.0$, and $0\leq z\leq1.0$). Furthermore, an Al compound (or Al alone) may also be prepared. The Si compound may be replaced by Si alone. Specific raw materials may be a $CeF_3$ powder, a LaN powder, a $Si_3N_4$ powder, and an AlN powder, for example. The $CeF_3$ powder may be replaced by a CeN powder. The $Si_3N_4$ powder may be replaced by a powder of Si alone. The AlN powder may be replaced by a powder of Al alone. The amount of the LaN powder may be approximately 24% more than the theoretical value. LaN is likely to be decomposed during firing, and the addition of excess LaN in the preparation of the raw materials can reduce the production of a by-product $LaSi_3N_5$ crystals.

A phosphor is produced by firing a mixture of the raw materials. The raw materials may be mixed by wet blending in a solution or by dry blending of dry powders. Industrially commonly used ball mills, medium stirring mills, planetary mills, vibrating mills, jet mills, V-type mixers, and agitators may be used. The firing is performed in a high-pressure nitrogen atmosphere at a temperature in the range of 1500° C. to 2000° C. for approximately 1 to 50 hours. The pressure is typically 3 atm or more, desirably 4 atm or more, more desirably 8 atm or more. After firing, the phosphor may be washed in a 10% nitric acid solution for 1 hour, for example. The resulting phosphor powder may be ground again in a ball mill or a jet mill and, if necessary, may be washed or classified to adjust the particle size distribution and flowability of the phosphor powder.

The red phosphor in the first embodiment will be further described below. The following also describes how the present inventors have developed the red phosphor.

<Principle of Light Emission of Rare-Earth Phosphor>

The following describes how the present inventors have studied the principle of light emission of a rare-earth phosphor and have focused on a $Ce^{3+}$ phosphor.

The divalent or trivalent ions of Ce, Pr, Nd, Pm, Sm, Eu, Gd, Tb, Dy, Ho, Er, Tm, and Yb of rare-earth elements have a valence electron in the 4f orbital. Among these, most of the rare-earth ions have multiple electrons in the 4f orbital and, as conceptually illustrated in FIG. 1A, lifting of the 4f orbital degeneracy causes large splitting of the 4f orbital. Thus, transition from one 4f level to another 4f level (f-f transition) can be utilized to emit light. Because the f-f transition is forbidden transition, excited electrons characteristically have a long life. Thus, phosphors containing a rare-earth ion are often used as laser media. When such phosphors are used in incoherent light sources, such as general illumination, however, the emission intensity is immediately saturated.

Figure 1B:
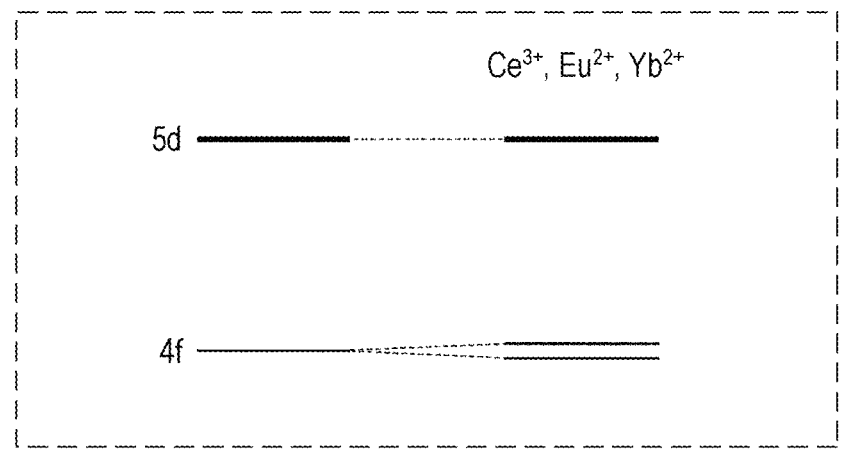
FIG. 1B is a schematic view of splitting of the 4f orbital and the 5d orbital of $Ce^{3+}$, $Eu^{2+}$, and $Yb^{2+}$.

$Ce^{3+}$ has only one valence electron in the 4f orbital. Thus, as conceptually illustrated in FIG. 1B, splitting of the 4f orbital is much smaller in $Ce^{3+}$ than in other rare-earth ions. Exceptionally, energy splitting of the 4f orbital in $Eu^{2+}$ and $Yb^{2+}$ is also small. This is because $Eu^{2+}$ has a semiclosed shell with seven electrons in the 4f orbital, and $Yb^{2+}$ has a closed shell with 14 electrons in the 4f orbital.

Due to the small splitting of the 4f orbital, $Ce^{3+}$, $Eu^{2+}$, and $Yb^{2+}$ have a large energy difference between the 4f ground level and the 5d orbital. Furthermore, there is no 4f orbital with large energy between the 4f ground level and the 5d orbital. Thus, transition between 4f and 5d (4f-5d transition) can be easily utilized.

The 4f-5d transition is allowed transition, and excited electrons therefore have short lives. Thus, excitation immediately induces light emission, and even excitation with strong excitation light is less likely to cause saturation (luminance saturation).

The present inventors have further focused on $Ce^{3+}$ out of $Ce^{3+}$, $Eu^{2+}$, and $Yb^{2+}$. $Ce^{3+}$ has only one electron involved in 4f-5d transition, and the 4f orbitals are completely vacant during transition from the 5d excited state to the 4f ground state; that is, the 4f orbital involved in transition has a high state density. Thus, the present inventors thought that $Ce^{3+}$ has the shortest emission lifetime. By contrast, $Eu^{2+}$ has six electrons in 4f after excitation of an electron to 5d, and $Yb^{2+}$ has 13 electrons remaining in 4f after excitation of an electron to 5d. Thus, $Eu^{2+}$ and $Yb^{2+}$ have a low state density in the 4f orbital and are expected to have a longer emission lifetime than $Ce^{3+}$. Thus, $Ce^{3+}$ phosphors have the shortest emission lifetimes among the rare-earth elements and are less likely to reach luminance saturation. Actually, YAG:Ce has a 1/e emission lifetime of approximately 70 ns, and CASN:Eu has a 1/e emission lifetime in the range of approximately 600 to 800 ns.

On the basis of these considerations, $Ce^{3+}$ phosphors are superior to $Eu^{2+}$ phosphors. Actually, almost all commercially available white LEDs include YAG:Ce. However, CASN:Eu is widely used as a red phosphor. The present inventors think that this is because $Ce^{3+}$ phosphors with red-light emission are difficult to develop, and promising materials have not been found. The reason for that and the principle that determines the emission wavelength will be described below.

<Emission Wavelength of Phosphor>

Phosphors with a $Ce^{3+}$ luminescent center and phosphors with a $Eu^{2+}$ luminescent center utilize transition from the ground state of the 4f orbital to the excited state of the 5d orbital (4f-5d transition). $Ce^{3+}$ and $Eu^{2+}$ introduced into a host crystal for a phosphor are mainly affected by the nearest bonded anion atom (ligand), and the energy of the 4f and 5d orbitals and the emission wavelength are changed. Thus, the emission wavelength of the phosphor depends on the host crystal.

Figure 2:
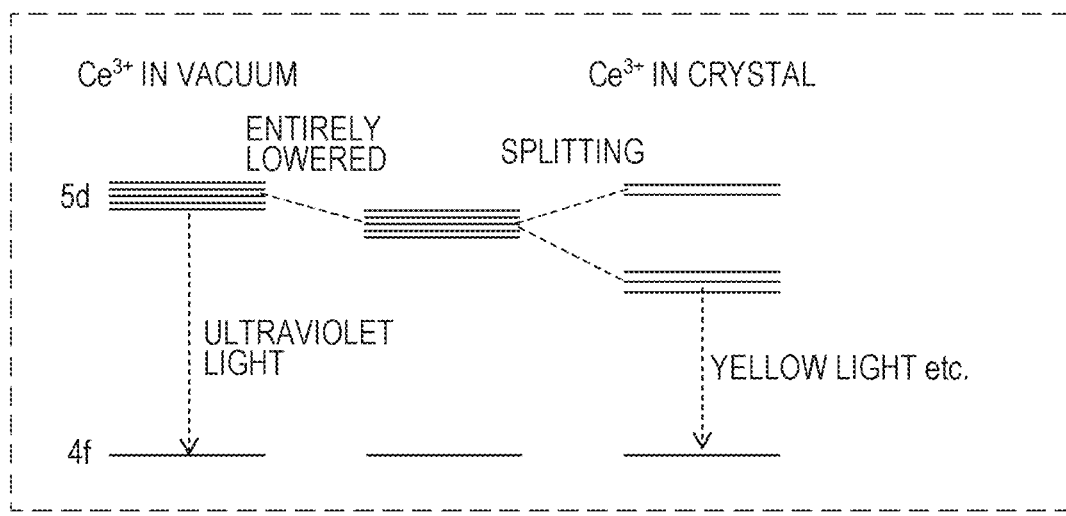
FIG. 2 is an energy level diagram of $Ce^{3+}$ in a vacuum and in a crystal.

The influence of the ligand includes the energy shift of the 4f or 5d orbital and the lifting of degeneracy of five levels of the 5d orbital (that is, splitting of the 5d orbital). The energy shift depends greatly on the expansion of the wave function of the 4f or 5d orbital and the positional relationship of the ligand. In the splitting of the 5d orbital, as illustrated in FIG. 2, the 5d orbital splits while the total energy of the five levels of the 5d orbital is maintained. Thus, an increase in the energy of one level is associated with a decrease in the energy of another level. Thus, splitting of the 5d orbital can be enlarged to decrease the lowest energy of the 5d orbital.

As illustrated in FIG. 2, light emission due to 4f-5d transition is caused by transition from the lowest energy level of the 5d orbital to 4f. Thus, $Ce^{3+}$ or $Eu^{2+}$ can be introduced into the crystal to decrease the 4f-5d energy difference and to increase the emission wavelength.

Although $Ce^{3+}$ in a vacuum (that is, not introduced into the crystal) has a large 4f-5d energy difference and emits light in a deep ultraviolet region, $Eu^{2+}$ emits blue light. Thus, $Eu^{2+}$ can emit red light with a smaller long-wavelength shift, and CASN:Eu is practically used. Practically used $Ce^{3+}$ phosphors having the longest wavelength are yellow phosphors YAG:Ce. Practically used $Ce^{3+}$ red phosphors have not been developed.

<Studied by the Present Inventors>

Figure 3:
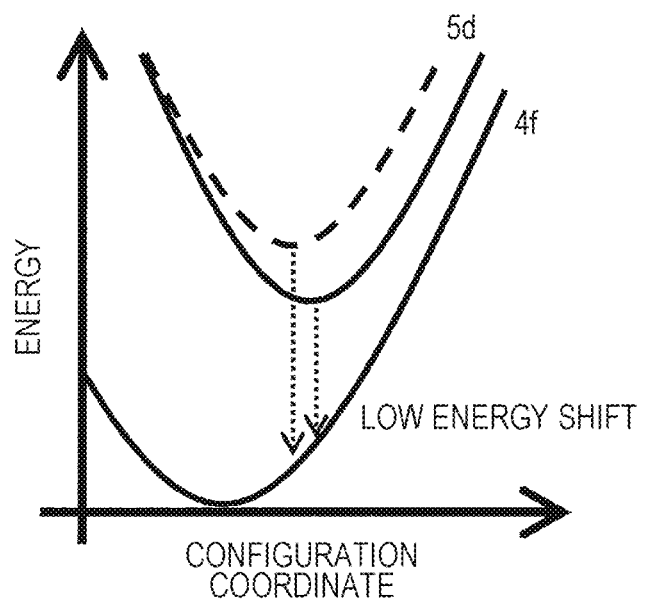
FIG. 3 is a configuration coordinate model diagram between the 4f orbital and the 5d orbital.

The present inventors have conducted studies considering that the 5d orbital or the 4f orbital is needed to be shifted to develop a Ce red phosphor, as illustrated in FIG. 3.

In order to shift the 5d orbital or the 4f orbital, it should be important for a ligand of $Ce^{3+}$ to satisfy (1) the short ligand distance and (2) low symmetry of the ligand.

Regarding (1), a short ligand distance between $Ce^{3+}$ and its nearest anion results in a large influence of the orbital of the anion on the 4f orbital, the 5d orbital, or both and a large energy shift of the 4f orbital, the 5d orbital, or both. This results in an increase in the energy of the 4f orbital or a decrease in the lowest energy level of the 5d orbital due to large splitting of the 5d orbital. These effects decrease the 4f-5d energy difference. Regarding (2), low symmetry of the ligand results in stabilization of the 5d orbital, which has a wave function extending in a direction in which no ligand exists. This decreases the 4f-5d energy difference.

On the basis of these guidelines, the present inventors have searched for a new material. More specifically, the present inventors examined the calculation of the emission wavelength by crystal structure simulation. Through these approaches, the present inventors have found new red phosphors that exhibit red. These approaches will be described below.

<Calculation of Emission Wavelength of Ce Phosphor>

In order to determine the relationship between the emission wavelength and the excitation wavelength of a phosphor including Ce as a luminescent center, the present inventors simulated the relationship between the emission wavelength and the excitation wavelength of various crystals doped with Ce. The results and discussion of the crystal structure simulation will be described below.

The present inventors calculated the emission wavelength using a technique described in the literature "Y Jia et al., Physical Review B 93, 155111 (2016)". In the technique, the excitation wavelength is calculated from the difference between the total energy at the equilibrium point of the ground state and the total energy of the excited state on the atomic coordinates. In the technique, the emission wavelength is calculated from the difference between the total energy at the equilibrium point at which the excited state is relaxed and the total energy of the ground state on the atomic coordinates. According to the literature, the calculated emission wavelengths and excitation wavelengths of three phosphors YAG:Ce, $LaSi_3N_5$:Ce, and $La_3Si_6N_{11}$:Ce agree well with experimental values. The present inventors calculated the emission wavelength and the excitation wavelength of $YAlO_3$:Ce as well as $LaSi_3N_5$:Ce and $La_3Si_6N_{11}$:Ce and confirmed that the calculation can precisely reproduce the experimental results as in the literature. Table 1 lists the excitation wavelength and the emission wavelength of each phosphor determined by the simulation.

TABLE 1

| | Chemical composition | | |
|---|---|---|---|
| | $(Y,Ce)AlO_3$ | $(La,Ce)Si_3N_5$ | $(La_3,Ce)Si_6N_{11}$ |
| Excitation wavelength (nm) | 310 | 366 | 470 |
| Emission wavelength (nm) | 349 | 445 | 543 |

<New Composition $(La,Y)_3Si_6N_{11}$:Ce Phosphor>

First, the present inventors intended to substitute $Y^{3+}$ at a $La^{3+}$ site of $La_3Si_6N_{11}$:Ce to shorten the ligand distance.

$Y^{3+}$ has a smaller ionic radius than $La^{3+}$. Thus, substitution of $Y^{3+}$ at a $La^{3+}$ site can decrease the lattice constant. A decrease in lattice constant is expected to shorten the ligand distance.

Figure 4:
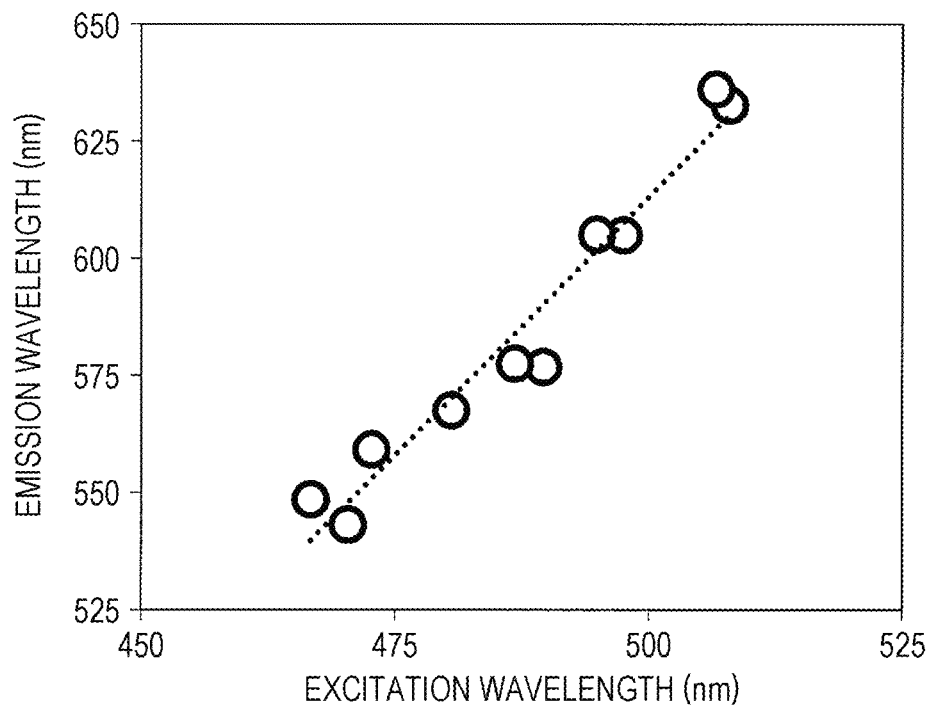
FIG. 4 is a graph showing the relationship between the excitation wavelength and the emission wavelength of a $(La,Y)_3Si_6N_{11}:Ce$ phosphor.
Figure 5:
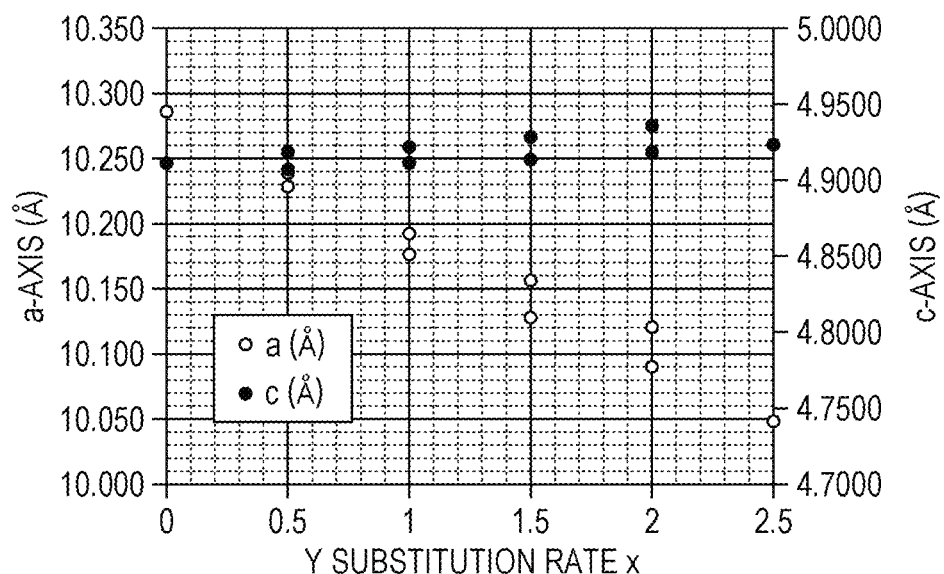
FIG. 5 is a graph showing the relationship between the $Y^{3+}$ substitution rate x and the lattice constant of the a-axis and the relationship between the $Y^{3+}$ substitution rate x and the lattice constant of the c-axis of the $(La,Y)_3Si_6N_{11}:Ce$ phosphor.
Figure 6:
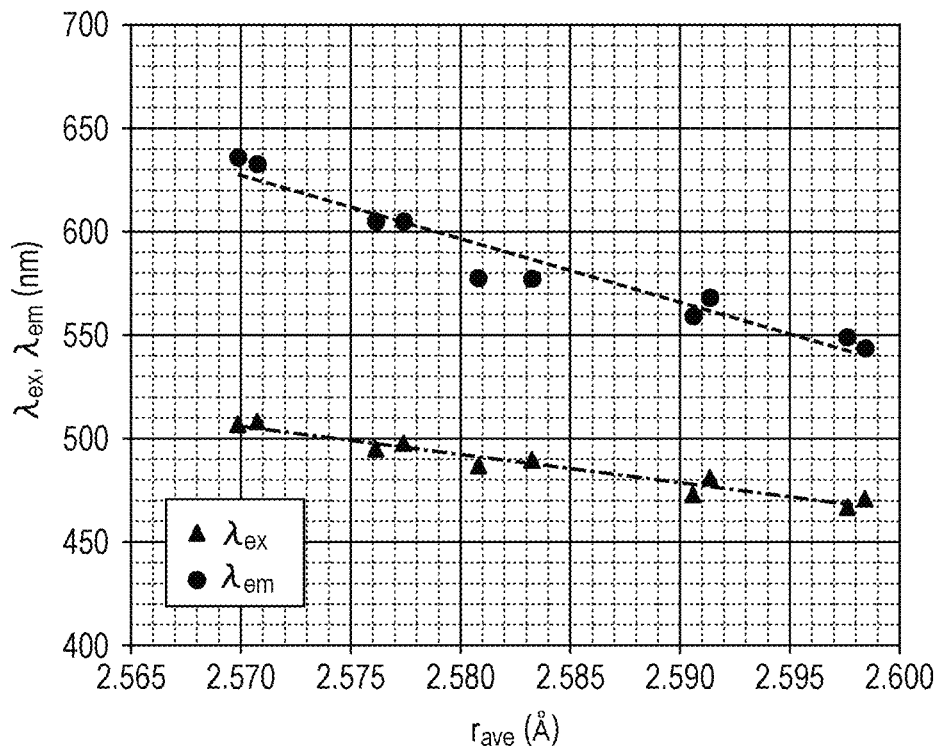
FIG. 6 is a graph showing the relationship between the average coordination distance $r_{ave}$ and the excitation wavelength $\lambda_{ex}$ and the relationship between the average coordination distance $r_{ave}$ and the emission wavelength $\lambda_{em}$ of the $(La,Y)_3Si_6N_{11}:Ce$ phosphor.
Figure 7:
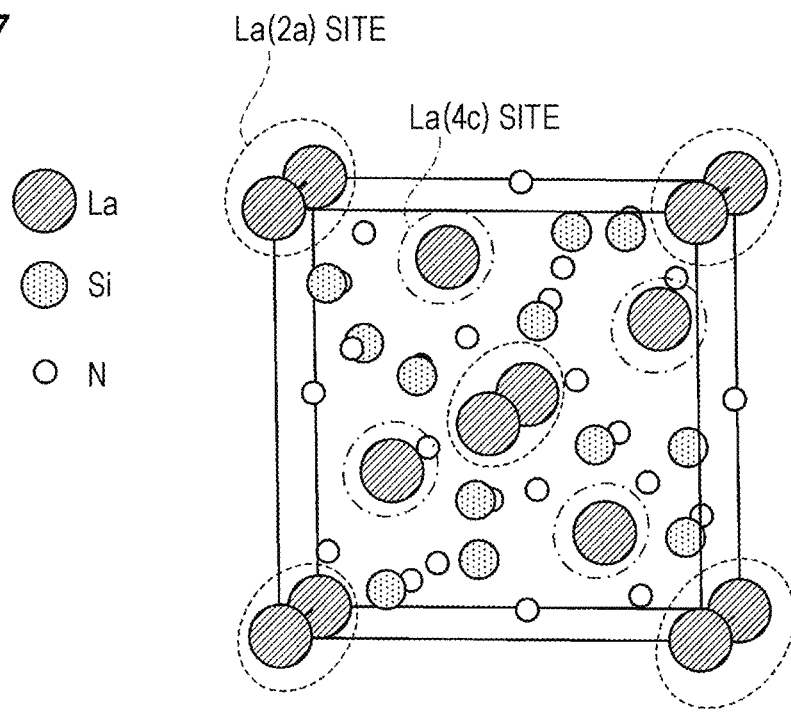
FIG. 7 is a schematic view of a $La_3Si_6N_{11}$ crystal structure and two different sites of La.
Figure 8A:
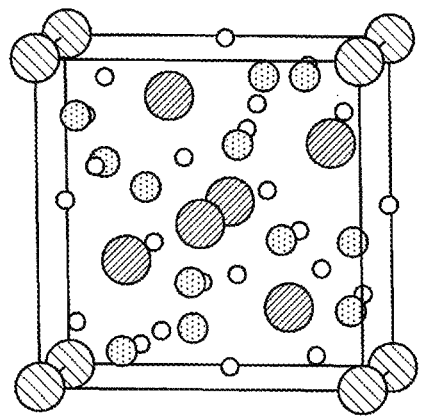
FIG. 8A is a schematic view of the crystal structure of a sample No. 1 of the $(La,Y)_3Si_6N_{11}:Ce$ phosphor.
Figure 8B:
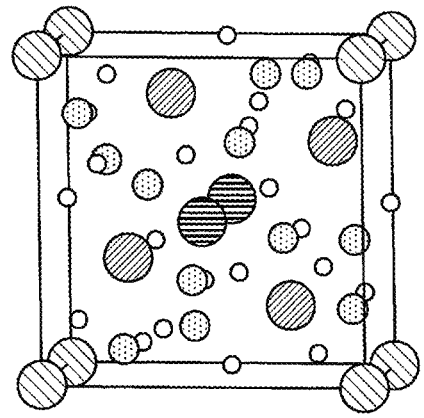
FIG. 8B is a schematic view of the crystal structure of a sample No. 2 of the $(La,Y)_3Si_6N_{11}:Ce$ phosphor.
Figure 8C:
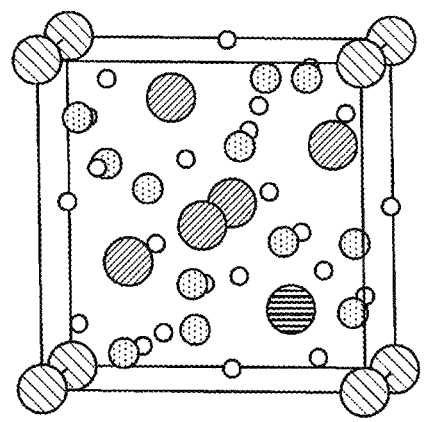
FIG. 8C is a schematic view of the crystal structure of a sample No. 3 of the $(La,Y)_3Si_6N_{11}:Ce$ phosphor.
Figure 8D:
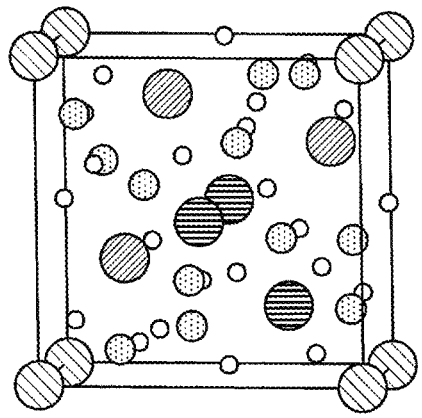
FIG. 8D is a schematic view of the crystal structure of a sample No. 4 of the $(La,Y)_3Si_6N_{11}:Ce$ phosphor.
Figure 8E:
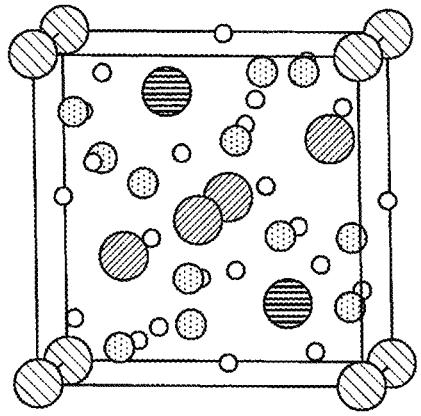
FIG. 8E is a schematic view of the crystal structure of a sample No. 5 of the $(La,Y)_3Si_6N_{11}:Ce$ phosphor.
Figure 8F:
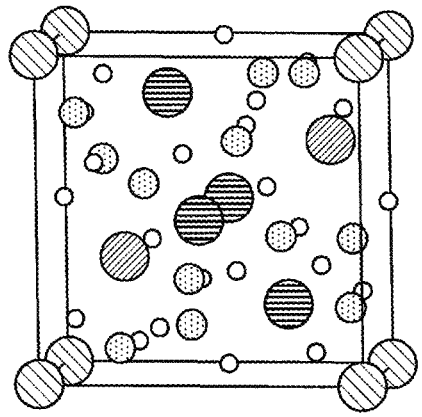
FIG. 8F is a schematic view of the crystal structure of a sample No. 6 of the $(La,Y)_3Si_6N_{11}:Ce$ phosphor.
Figure 8G:
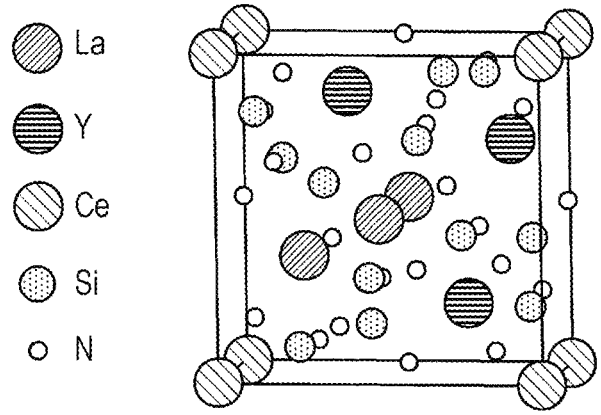
FIG. 8G is a schematic view of the crystal structure of a sample No. 7 of the $(La,Y)_3Si_6N_{11}:Ce$ phosphor.
Figure 8H:
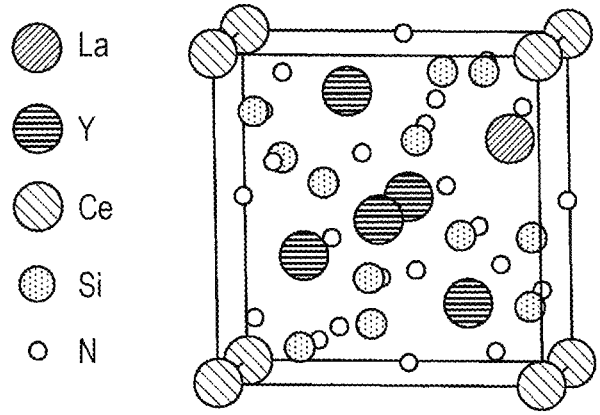
FIG. 8H is a schematic view of the crystal structure of a sample No. 8 of the $(La,Y)_3Si_6N_{11}:Ce$ phosphor.
Figure 8I:
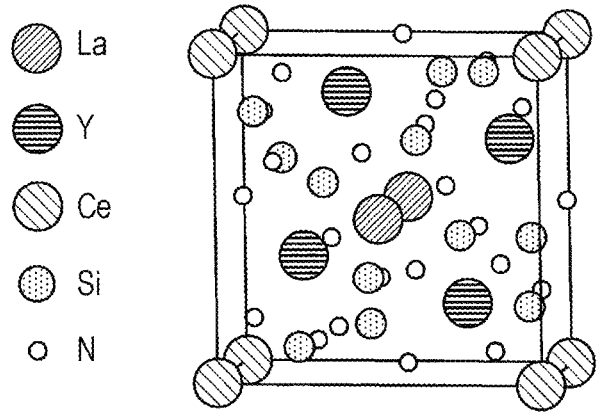
FIG. 8I is a schematic view of the crystal structure of a sample No. 9 of the $(La,Y)_3Si_6N_{11}:Ce$ phosphor.
Figure 8J:
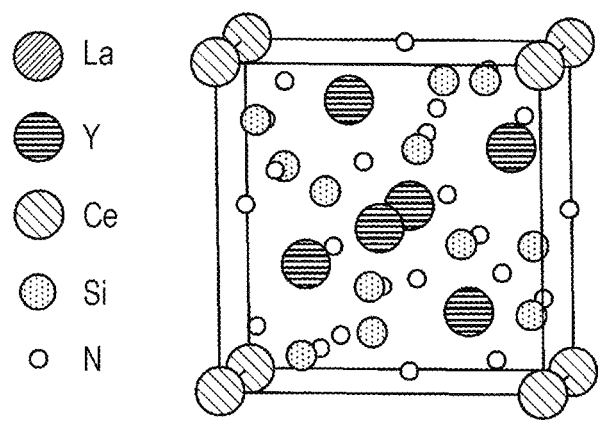
FIG. 8J is a schematic view of the crystal structure of a sample No. 10 of the $(La,Y)_3Si_6N_{11}$:Ce phosphor.
Figure 9:
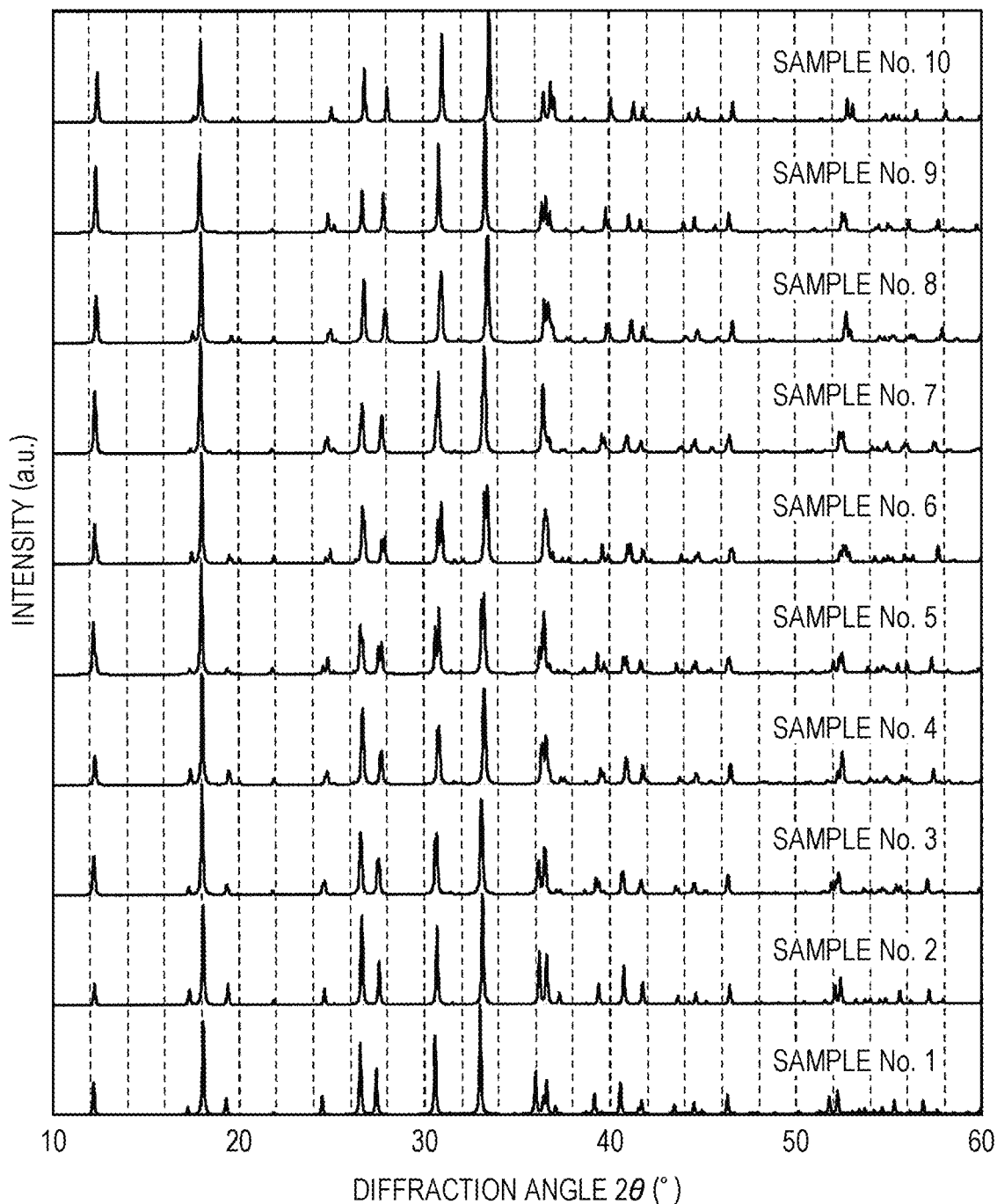
FIG. 9 is a graph of powder XRD diffraction patterns calculated from the crystal structures of the phosphors of the samples No. 1 to No. 10 illustrated in FIGS. 8A to 8J.

A new composition $(La,Y)_3Si_6N_{11}$:Ce phosphor was studied by the calculation technique. The phosphor of this composition includes substitution of $Y^{3+}$ at a $La^{3+}$ site of $La_3Si_6N_{11}$:Ce. $Y^{3+}$ has a smaller ionic radius than $La^{3+}$. Thus, the ligand distance of $Ce^{3+}$ is smaller in $(La,Y)_3Si_6N_{11}$ than in $La_3Si_6N_{11}$. This is expected to increase the emission wavelength. Table 2 shows the calculation results of the average coordination distance $r_{ave}$ between Ce and N, the excitation wavelength $\lambda_{ex}$, and the emission wavelength $\lambda_{em}$ with different $Y^{3+}$ substitution rates. FIG. 4 is a graph showing the relationship between the excitation wavelength and the emission wavelength. FIG. 5 shows the relationship between the $Y^{3+}$ substitution rate x and the lattice constant of the a-axis and the relationship between the $Y^{3+}$ substitution rate x and the lattice constant of the c-axis. FIG. 6 shows the relationship between the average coordination distance $r_{ave}$ and the excitation wavelength $\lambda_{ex}$ and the relationship between the average coordination distance $r_{ave}$ and the emission wavelength $\lambda_{em}$. FIG. 7 illustrates a $La_3Si_6N_{11}$ crystal structure and two different sites of La. In FIG. 7, La(2a) sites are indicated by broken lines, and La(4c) sites are indicated by dash-dot lines. FIGS. 8A to 8J illustrate the crystal structures of samples No. 1 to No. 10. FIG. 9 shows powder XRD diffraction patterns calculated from the crystal structures of the samples No. 1 to No. 10. The symbol * in Table 2 shows that the sample is a comparative example. In the column "Y substitution site and substitution rate" of Table 2, the Y substitution site and the substitution rate are represented by "Y substitution site←Y substitution rate".

TABLE 2

| Sample No. | Composition formula | Y substitution site and substitution rate | $r_{ave}$ (Å) | $\lambda_{ex}$ (nm) | $\lambda_{em}$ (nm) |
|---|---|---|---|---|---|
| *1 | $(La_{2.5},Ce_{0.5})Si_6N_{11}$ | — | 2.5984 | 470 | 543 |
| *2 | $(La_2,Y_{0.5},Ce_{0.5})Si_6N_{11}$ | La(2a)←$Y_{0.5}$ | 2.5976 | 467 | 549 |
| *3 | $(La_2,Y_{0.5},Ce_{0.5})Si_6N_{11}$ | La(4c)←$Y_{0.5}$ | 2.5913 | 481 | 568 |
| *4 | $(La_{1.5},Y_1,Ce_{0.5})Si_6N_{11}$ | La(2a)←$Y_{0.5}$, La(4c)←$Y_{0.5}$ | 2.5905 | 473 | 559 |
| *5 | $(La_{1.5},Y_1,Ce_{0.5})Si_6N_{11}$ | La(4c)←$Y_1$ | 2.5832 | 490 | 577 |
| *6 | $(La_1,Y_{1.5},Ce_{0.5})Si_6N_{11}$ | La(2a)←$Y_{0.5}$, La(4c)←$Y_1$ | 2.5808 | 487 | 578 |
| 7 | $(La_1,Y_{1.5},Ce_{0.5})Si_6N_{11}$ | La(4c)←$Y_{1.5}$ | 2.5774 | 498 | 605 |
| 8 | $(La_{0.5},Y_2,Ce_{0.5})Si_6N_{11}$ | La(2a)←$Y_{0.5}$, La(4c)←$Y_{1.5}$ | 2.5761 | 495 | 605 |
| 9 | $(La_{0.5},Y_2,Ce_{0.5})Si_6N_{11}$ | La(4c)←$Y_2$ | 2.5707 | 508 | 633 |
| 10 | $(Y_{2.5},Ce_{0.5})Si_6N_{11}$ | La(2a)←$Y_{0.5}$, La(4c)←$Y_2$ | 2.5698 | 507 | 636 |

Table 2 and FIG. 4 show that the emission wavelength tends to increase with the $Y^{3+}$ substitution rate. The excitation peak wavelength also increases with the emission wavelength. In the compositions of the samples 7 to 10 that emit red light at an emission wavelength of 600 nm or more, the peak excitation wavelength is in a green region of 490 nm or more. As is clear from FIG. 5, an increase in $Y^{3+}$ substitution rate results in a decrease in the lattice constant of the a-axis and an increase in the lattice constant of the c-axis. As is clear from Table 2 and FIG. 6, an increase in $Y^{3+}$ substitution rate results in a decrease in the average coordination distance $r_{ave}$ between Ce and N, and a decrease in $r_{ave}$ results in an increase in emission wavelength and excitation wavelength.

$Eu^{2+}$ has a much longer emission lifetime than $Ce^{3+}$. The emission lifetime correlates with the 4f-5d transition probability of $Eu^{2+}$ and $Ce^{3+}$, and a longer emission lifetime results in a lower transition probability. Thus, the excitation probability of 4f-5d transition of $Eu^{2+}$ is much lower than the excitation probability of 4f-5d transition of $Ce^{3+}$. However, the 5d excitation level of $Eu^{2+}$ is likely to overlap the conduction band of the host material $((La,Y)_3Si_6N_{11})$. This enables efficient energy absorption between the 4f ground level of $Eu^{2+}$ and the conduction band of the host material. The absorbed energy corresponds to energy in a blue light region. $Eu^{2+}$ has seven electrons in the 4f orbital. Each of the electrons has a wide energy level, and $Eu^{2+}$ therefore has a broad excitation wavelength. Thus, a red phosphor with a $Eu^{2+}$ luminescent center has a broad excitation wavelength with a peak in a blue region. Thus, a light source containing the red phosphor with the $Eu^{2+}$ luminescent center includes an excitation light source that can emit blue light with the highest absorption efficiency.

By contrast, the 5d excitation level of a phosphor with a $Ce^{3+}$ luminescent center is less likely to overlap the conduction band of the host material. Energy absorption between the 4f ground level and the conduction band of the host material is therefore not expected. Thus, 4f-5d transition is main energy absorption.

On the basis of the study results, the present inventors proved that the energy difference in 4f-5d transition of a red phosphor with $Ce^{3+}$ corresponds to the energy difference in a green light region. Thus, a red phosphor with $Ce^{3+}$ has higher absorption efficiency with an excitation light source of green light than with an excitation light source of blue light. The use of green light can increase light output. A method for converting green light to red light according to the present application can have a smaller energy conversion loss (e.g., Stokes' loss) and can emit higher-power light than a known method for converting blue light to red light.

From these results, the present inventors have developed a new red phosphor containing a crystal phase having the chemical composition $Ce_xY_pLa_{3-x-p}Si_6N_{11}$, wherein $0<x\leq0.6$ and $(1.5-x)\leq p\leq(3-x)$. This new red phosphor is hereinafter referred to as a red phosphor of a second example in the first embodiment and will be described in detail below.

In the chemical composition of the red phosphor of the second example in the first embodiment, x satisfies $0<x\leq0.6$. Since x is more than 0, Ce can emit light. In order to increase emission intensity, x is desirably 0.0003 or more, more desirably 0.015 or more. The maximum value of x is not particularly limited as long as the phosphor can emit light. However, an excessively large x results in low emission intensity due to concentration quenching. Thus, the decrease in emission intensity can be reduced when x is 0.6 or less. In order to increase emission intensity, x is desirably 0.3 or less, more desirably 0.15 or less.

In the red phosphor of the second example in the first embodiment, in order to increase the emission wavelength and the excitation wavelength, it is desirable to increase substitution of Y for La. Thus, in the chemical composition of the red phosphor of the second example in the first embodiment, x and p desirably satisfy $(1.5-0.5x)\leq p\leq(3-x)$, more desirably $1.5\leq p\leq(3-x)$.

The red phosphor of the second example in the first embodiment has an emission spectrum peak in the wavelength range of 600 to 660 nm. The red phosphor of the second example in the first embodiment may have an emission spectrum peak with a wavelength of 605 nm or more, for example. The red phosphor of the second example in the first embodiment may have an emission spectrum peak with a wavelength of 640 nm or less or an emission spectrum peak with a wavelength of 636 nm or less, for example.

The red phosphor of the second example in the first embodiment has an excitation spectrum peak in the wavelength range of 480 to 550 nm. The red phosphor of the second example in the first embodiment may have an excitation spectrum peak with a wavelength of 490 nm or more or an excitation spectrum peak with a wavelength of 495 nm or more, for example. The red phosphor of the second example in the first embodiment may have an excitation spectrum peak with a wavelength of 530 nm or less or an excitation spectrum peak with a wavelength of 508 nm or less, for example.

When the excitation spectrum peak in the wavelength range of 480 to 550 nm is referred to as a first excitation spectrum peak, the red phosphor of the second example in the first embodiment may further have a second excitation spectrum peak in the wavelength range of 350 nm or more and less than 480 nm. The first or second excitation spectrum peak may be the maximum peak of the excitation spectrum.

The crystal phase of the red phosphor of the second example in the first embodiment may have a 1/e emission lifetime of 100 ns or less. The emission lifetime has an influence on the luminance saturation characteristics. Phosphors containing Eu, such as a known red phosphor CASN:Eu, have a longer emission lifetime than phosphors containing Ce. Thus, phosphors containing Eu are likely to reach luminance saturation due to a decrease in quantum efficiency during high-energy excitation. Thus, the red phosphor including the Ce luminescent center of the first embodiment is expected to be a red phosphor with higher quantum efficiency than known red phosphors even at high power.

The host material of the red phosphor of the second example in the first embodiment may contain a tetragonal crystal. In other words, a crystal phase having the chemical composition $Ce_xY_pLa_{3-x-p}Si_6N_{11}$ in the red phosphor of the second example in the first embodiment may have a tetragonal crystal structure. The crystal phase may have almost the same crystal structure as a crystal represented by the general formula $La_3Si_6N_{11}$.

The crystal phase of the red phosphor of the second example in the first embodiment may have a crystal structure in which Ce substitutes at least part of the La(2a) sites of the $La_3Si_6N_{11}$ crystal structure. The crystal phase of the red phosphor of the second example in the first embodiment may have a crystal structure in which Y substitutes at least part of the La(4c) sites of the $La_3Si_6N_{11}$ crystal structure or a crystal structure in which Y substitutes the majority of the La(4c) sites of the $La_3Si_6N_{11}$ crystal structure.

As illustrated in FIG. 7, La in the $La_3Si_6N_{11}$ crystal structure has two coordination states: the La(2a) sites and the La(4c) sites. The La(2a) sites have high symmetry, and the La(4c) sites have low symmetry. For example, substitution of Ce with a large ionic radius for La at a La(2a) site with high symmetry decreases the enthalpy of formation by approximately 48 meV as determined by first principle calculation and is thermodynamically stable. From this standpoint, the crystal phase of the phosphor of the first embodiment desirably has a crystal structure in which Ce substitutes at least part of the La(2a) sites of the $La_3Si_6N_{11}$ crystal structure. Furthermore, for example, substitution of Y for La at a La(4c) site with low symmetry enlarges the splitting of the 5d orbital of Ce due to large lattice distortion. This decreases the energy difference between the 4f orbital and the 5d orbital and can shift the excitation wavelength and the emission wavelength to the long wavelength side. From this standpoint, the crystal phase of the phosphor of the first embodiment desirably has a crystal structure in which Y substitutes at least part of the La(4c) sites of the $La_3Si_6N_{11}$ crystal structure. Furthermore, the crystal phase of the phosphor of the first embodiment more desirably has a crystal structure in which Y substitutes the majority of the La(4c) sites of the $La_3Si_6N_{11}$ crystal structure.

<Method for Producing Red Phosphor of Second Example in First Embodiment>

A method for producing the red phosphor of the second example in the first embodiment will be described below.

For example, a Ce compound, a La compound, a Si compound, and a Y compound may be used as raw materials, or each of Ce, La, Si, and Y may be used as a raw material. The compound may be a compound that can be converted into a nitride by firing in a nitrogen atmosphere, a high-purity (purity of 99% or more) nitride, or a metal alloy. A small amount of fluoride (such as ammonium fluoride) may be added to promote the reaction.

For example, a Ce compound, a La compound, a Si compound, and a Y compound may be prepared at a chemical composition ratio represented by $Ce_xY_yLa_{3-x-y}Si_6N_{11}$ ($0<x\leq0.6$, $(1.5-x)\leq y\leq(3-x)$). The Si compound may be replaced by Si alone. Specific raw materials may be a $CeF_3$ powder, a LaN powder, a $Si_3N_4$ powder, and a YN powder, for example. The $CeF_3$ powder may be replaced by a CeN powder. The $Si_3N_4$ powder may be replaced by a powder of Si alone. The amount of the LaN powder may be approximately 24% more than the theoretical value. LaN is likely to be decomposed during firing, and the addition of excess LaN in the preparation of the raw materials can reduce the production of a by-product $LaSi_3N_5$ crystals.

The red phosphor of the second example in the first embodiment is produced by firing a mixture of the raw materials. The raw materials may be mixed by wet blending in a solution or by dry blending of dry powders. Industrially commonly used ball mills, medium stirring mills, planetary mills, vibrating mills, jet mills, V-type mixers, and agitators may be used. The firing is performed in a high-pressure nitrogen atmosphere at a temperature in the range of 1500° C. to 2000° C. for approximately 1 to 50 hours. The pressure is typically 3 atm or more, desirably 4 atm or more, more desirably 8 atm or more. After firing, the phosphor may be washed in a 10% nitric acid solution for 1 hour, for example. The resulting phosphor powder may be ground again in a ball mill or a jet mill and, if necessary, may be washed or classified to adjust the particle size distribution and flowability of the phosphor powder.

<New Composition $La_3(Si,Al)_6N_{11}$:Ce Phosphor>

In order to increase the emission wavelength of a phosphor to provide a Ce red phosphor, the present inventors intended to reduce the symmetry of a ligand of Ce. More specifically, the present inventors intended to introduce $Al^{3+}$ into $La_3Si_6N_{11}$:Ce.

$Al^{3+}$ has a much smaller ionic radius than $La^{3+}$. Thus, substitution of $Al^{3+}$ at a $La^{3+}$ site greatly distorts the crystal and is expected to reduce the symmetry of the ligand. Alternatively, having an ionic radius similar to that of $Si^{4+}$, $Al^{3+}$ may occupy a $Si^{4+}$ site. In this case, $N^{3-}$ may be simultaneously substituted by $O^{2-}$ to adjust the valence. Furthermore, substitution of $Al^{3+}$ at three $Si^{4+}$ sites may be accompanied by a loss of $N^{3-}$. In both cases, the symmetry of the ligand is reduced.

On the basis of these findings, the present inventors have found a crystal structure that potentially includes a ligand with lower symmetry than a ligand of Ce in known LSN:Ce yellow phosphors, as described later. A phosphor having the chemical composition LSN:Ce disclosed in Japanese Patent No. 4459941 as an example of known LSN:Ce yellow phosphors has an emission peak wavelength in the range of 574 to 594 nm and an excitation peak wavelength in the range of 455 to 460 nm.

The results and discussion of the crystal structure simulation will be described below. In order to examine a site of the $La_3Si_6N_{11}$ crystal structure that can be substituted by Ce, first principle calculation was used in substitution of Ce at a La site of $La_3Si_6N_{11}$ and in structural optimization. CASTEP available from Dassault Systemes Biovia K. K. was used for the first principle calculation. GGA was used as a functional, and PBE was used for exchange-correlation interaction.

Figure 10:
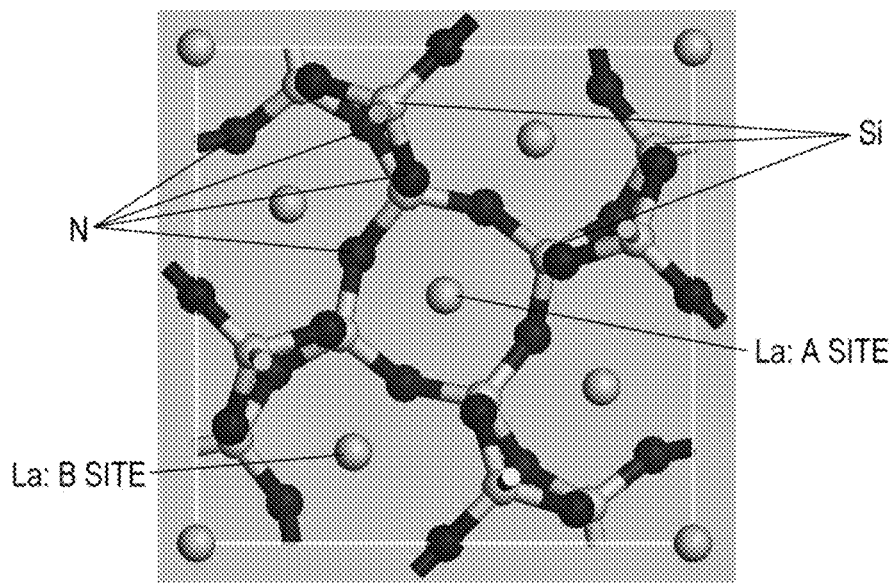
FIG. 10 is a schematic view of a 1×1×3 supercell structure of $La_3Si_6N_{11}$ after structural optimization.
Figure 11:
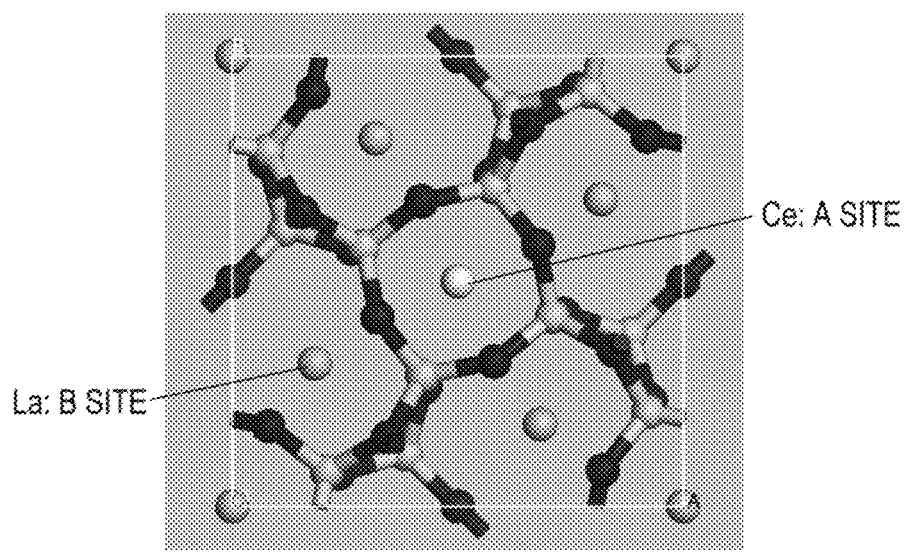
FIG. 11 is a schematic view of a 1×1×3 supercell structure of $La_3Si_6N_{11}$:Ce after substitution of Ce for La at an A site and after structural optimization.
Figure 12:
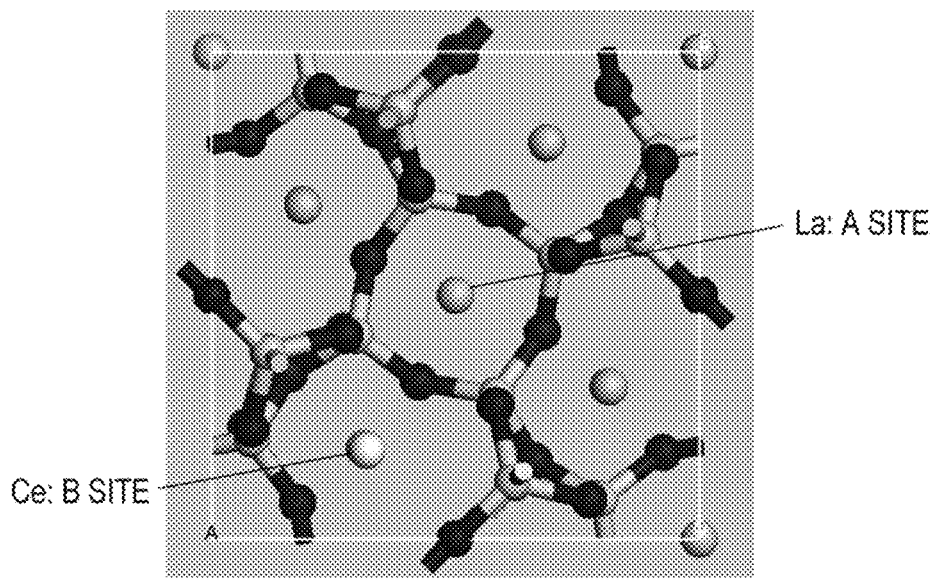
FIG. 12 is a schematic view of a 1×1×3 supercell structure of $La_3Si_6N_{11}$:Ce after substitution of Ce for La at a B site and after structural optimization.

FIG. 10 illustrates the structural optimization results of the 1×1×3 supercell of $La_3Si_6N_{11}$. The space group of a unit cell of $La_3Si_6N_{11}$ is P4bm (#100). The coordination state of La includes an A site with high symmetry and a B site with low symmetry. FIG. 11 illustrates a crystal structure 1 including substitution of Ce for La at an A site and subjected to structural optimization. FIG. 12 illustrates a crystal structure 2 including substitution of Ce for La at a B site and subjected to structural optimization.

FIG. 11 shows that eight N atoms are located at almost equal distances around Ce at an A site. Two quadrangular pyramids with Ce at the vertex share the vertex and have eight coordination geometry with square bottoms twisted 45 degrees with respect to each other. The eight coordination geometry includes a ligand of Ce with high symmetry FIG. 12 shows that eight N atoms are located at different distances and angles around Ce at a B site. A ligand of Ce has lower symmetry at the B site than at the A site.

Table 3 lists the Ce-N distance and its standard deviation of the crystal structure 1 including substitution of Ce for La at an A site of the $La_3Si_6N_{11}$ crystal structure and the crystal structure 2 including substitution of Ce for La at a B site of the $La_3Si_6N_{11}$ crystal structure for quantification of symmetry.

the enthalpy of formation being lower by 48 meV in the crystal structure 1 than in the crystal structure 2.

Thus, in known LSN:Ce yellow phosphors, Ce is located at an energetically stable A site at which a ligand has high symmetry, for example, as in the crystal structure 1. This probably results in yellow light emission.

These analysis results show that the equilibrium point of the 4f orbital and the 5d orbital shifts due to low symmetry of a ligand of Ce in $La_3Si_6N_{11}$:Ce including substitution of Ce for La at a B site as in the crystal structure 2. Thus, it is possible to emit light with a longer wavelength than light emitted from known LSN:Ce yellow phosphors.

The red phosphor of the first embodiment may contain Al in the starting material, and therefore Al may be incorporated into the crystal phase of the phosphor. Furthermore, O in the raw materials may be incorporated into the phosphor crystal phase. Si and Al as well as N and O are interchangeable due to their similar ionic radii. The ionic radii are Al>Si and N>O. Thus, substitution of Al for Si increases the lattice constant, and substitution of O for N decreases the lattice constant. Simultaneous substitution of Al for Si and O for N can further stabilize the crystal. Simultaneous substitution of Al for Si and O for N can also maintain the valence of the crystal. Thus, the numbers of moles of Al and O in the crystal phase may be the same.

Figure 13:
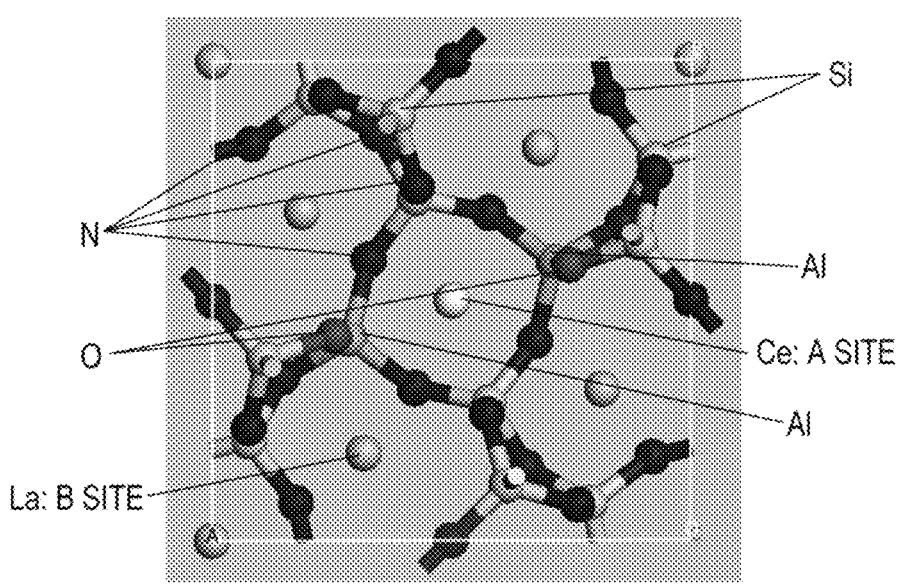
FIG. 13 is a schematic view of a 1×1×3 supercell structure of $La_3Si_6N_{11}$:Ce after substitution of Ce for La at an A site, substitution of Al at a Si site, and substitution of O at a N site, and after structural optimization.
Figure 14:
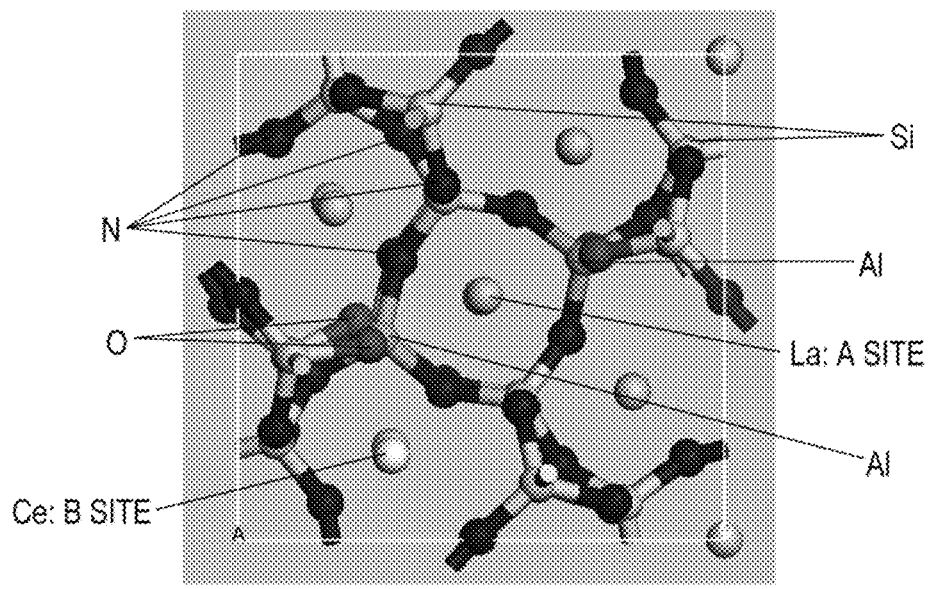
FIG. 14 is a schematic view of a 1×1×3 supercell structure of $La_3Si_6N_{11}$:Ce after substitution of Ce for La at a B site, substitution of Al at a Si site, and substitution of O at a N site, and after structural optimization.

From these viewpoints, and in order to reduce symmetry, a crystal structure including substitution of Al at part of the Si sites and substitution of O at part of the N sites near Ce of $La_3Si_6N_{11}$:Ce was studied. FIG. 13 illustrates a crystal structure 3 including substitution of Ce for La at an A site in the original crystal structure and subjected to structural optimization. FIG. 14 illustrates a crystal structure 4 including substitution of Ce for La at a B site in the original crystal structure and subjected to structural optimization. Table 3 lists the Ce—N distance and its standard deviation of the crystal structure 3 and the crystal structure 4. The standard deviations of the crystal structure 3 and the crystal structure 4 are larger than that of the crystal structure 1, thus showing a decrease in the symmetry of a ligand of Ce.

These analysis results show that the equilibrium point of the 4f orbital and the 5d orbital of a crystal structure

TABLE 3

| | Ce—N distance (Å) | | | | | | | | Standard deviation |
|---|---|---|---|---|---|---|---|---|---|
| | Ce—N1 | Ce—N2 | Ce—N3 | Ce—N4 | Ce—N5 | Ce—N6 | Ce—N7 | Ce—N8 | σCe—N |
| Crystal structure 1 | 2.628 | 2.614 | 2.621 | 2.629 | 2.650 | 2.646 | 2.662 | 2.665 | 0.019 |
| Crystal structure 2 | 2.508 | 2.366 | 2.508 | 2.366 | 2.696 | 2.775 | 2.697 | 2.774 | 0.171 |
| Crystal structure 3 | 2.717 | 2.462 | 3.593 | 3.007 | 2.810 | 3.595 | 2.469 | 2.735 | 0.450 |
| Crystal structure 4 | 3.099 | 2.303 | 3.670 | 3.107 | 2.551 | 3.670 | 2.314 | 2.578 | 0.560 |

The results also show that the Ce ligand has lower symmetry in the crystal structure 2 including substitution of Ce for La at a B site than in the crystal structure 1 including substitution of Ce for La at an A site.

In order to determine which of La at an A site or La at a B site is easy to substitute by Ce, the enthalpy of formation of each crystal was calculated by first principle calculation. It was found that the crystal structure 1 including substitution of Ce for La at an A site is more stable than the crystal structure 2 including substitution of Ce for La at a B site with including substitution of Al at part of the Si sites and substitution of O at part of the N sites near Ce of $La_3Si_6N_{11}$:Ce, such as the crystal structure 3 or the crystal structure 4, shifts due to low symmetry of a ligand of Ce, and therefore such a structure can emit light with a longer wavelength than light emitted from known LSN:Ce yellow phosphors. In this case, in order to emit light with a longer wavelength than light emitted from known LSN:Ce yellow phosphors, it is desirable that the crystal phase contain a larger amount of Al or O or both than Ce.

Furthermore, a crystal structure including substitution of Al at part of the Si sites near Ce of $La_3Si_6N_{11}$:Ce and including a defect at a N site was examined. In order to adjust the valence in substitution of $Al^{3+}$ for $Si^{4+}$, it is desirable that substitution of three $Al^{3+}$ ions for three $Si^{4+}$ ions be simultaneously accompanied by a loss of one $N^{3-}$. Substitution of Al for coordinating Si near Ce simultaneous with a loss of N reduces the symmetry of a ligand of Ce.

in Table 4. In Comparative Example 1, no AlN powder was added. The mixing method was dry blending with a mortar in a glove box in a nitrogen atmosphere. The mixed raw powders were placed in a boron nitride crucible. The raw powders were fired in a 0.5 MPa nitrogen atmosphere at 1900° C. for 2 hours. The fired sample was washed in a 10% nitric acid solution for 1 hour. Examples 1 to 4 and Comparative Example 1 were produced from the starting materials listed in Table 4 in this way.

TABLE 4

|  | LaN | $Si_3N_4$ | AlN | $CeF_3$ | x | Emission peak wavelength | Excitation peak wavelength |
|---|---|---|---|---|---|---|---|
| Example 1 | 1.316 g | 0.659 g | 0.096 g | 0.042 g | 0.09 | 642 nm | 540 nm |
| Example 2 | 1.206 g | 0.604 g | 0.265 g | 0.038 g | 0.09 | 642 nm | 537 nm |
| Example 3 | 1.113 g | 0.557 g | 0.407 g | 0.035 g | 0.09 | 642 nm | 539 nm |
| Example 4 | 0.932 g | 0.467 g | 0.682 g | 0.030 g | 0.09 | 641 nm | 539 nm |
| Comparative example 1 | 1.380 g | 0.691 g | 0 g | 0.044 g | 0.09 | 536 nm | 450 nm |

Thus, it is possible to emit light with a longer wavelength than light emitted from known LSN:Ce yellow phosphors.

In this case, in order to emit light with a longer wavelength than light emitted from known LSN:Ce yellow phosphors, it is desirable that at least the amount of Al be greater than or equal to the amount of Ce. Furthermore, substitution of Al at three Si sites can provide charge compensation for a N defect. Thus, it is desirable that the amount of Al be at least three times the amount of Ce.

The results of the crystal structure simulation show that a phosphor having any of the following crystal structures can emit light with a longer wavelength than light emitted from known LSN:Ce yellow phosphors: (1) a crystal structure including substitution of Ce for La at a B site of a $La_3Si_6N_{11}$ crystal, (2) a crystal structure including substitution of Ce at at least one of an A site and a B site of La of a $La_3Si_6N_{11}$ crystal and substitution of Al—O for part of Si-N near Ce, and (3) a crystal structure including substitution of Ce at an A site and/or a B site of La of a $La_3Si_6N_{11}$ crystal, substitution of Al for Si near Ce, and a loss of N.

The simulation results suggest the reason why the phosphor of the first embodiment emits red light with a longer wavelength than light emitted from known LSN:Ce yellow phosphors. The simulation results are described by way of example only and do not limit the crystal structure of the phosphor of the first embodiment.

From these results, the present inventors have found a new red phosphor containing a crystal phase having the chemical composition $Ce_xLa_{3-x}Si_{6-q}Al_qN_{11-z}$. In the new red phosphor, x, q, and z satisfy $0<x\leq0.6$, $0<q\leq3.0$, and $0\leq z \leq 1.0$. This new red phosphor is hereinafter referred to as a red phosphor of a third example in the first embodiment and will be further described in the following examples.

EXAMPLES 1 TO 4 AND COMPARATIVE EXAMPLE 1

A method for producing a phosphor will be described below. A LaN powder, a $Si_3N_4$ powder, an AlN powder, and a $CeF_3$ powder were prepared as starting materials. First, the LaN powder, the $Si_3N_4$ powder, and the $CeF_3$ powder were weighed and mixed at a composition represented by the general formula $La_{2.91}Ce_{0.09}Si_6N_{11}$. The amount of the LaN powder was 24% more than the theoretical value. The mixed powder was mixed with the AlN powder in the amount listed

COMPARATIVE EXAMPLE 2

A $Ca_3N_2$ powder, a $Si_3N_4$ powder, an AlN powder, and a EuN powder were prepared as starting materials. The $Ca_3N_2$ powder, the $Si_3N_4$ powder, the AlN powder, and the EuN powder were weighed and mixed at a composition represented by the general formula $Ca_{0.97}Eu_{0.03}AlSiN_3$. The mixing method was dry blending with a mortar in a glove box in a nitrogen atmosphere. The mixed raw powders were placed in a boron nitride crucible. The raw powders were fired in a 0.5 MPa nitrogen atmosphere at 1600° C. for 2 hours. The fired sample was washed in a 10% nitric acid solution for 1 hour. Comparative Example 2 represented by CASN:Eu was produced in this way.

<Evaluation of Emission/Excitation Spectrum>

Figure 15:
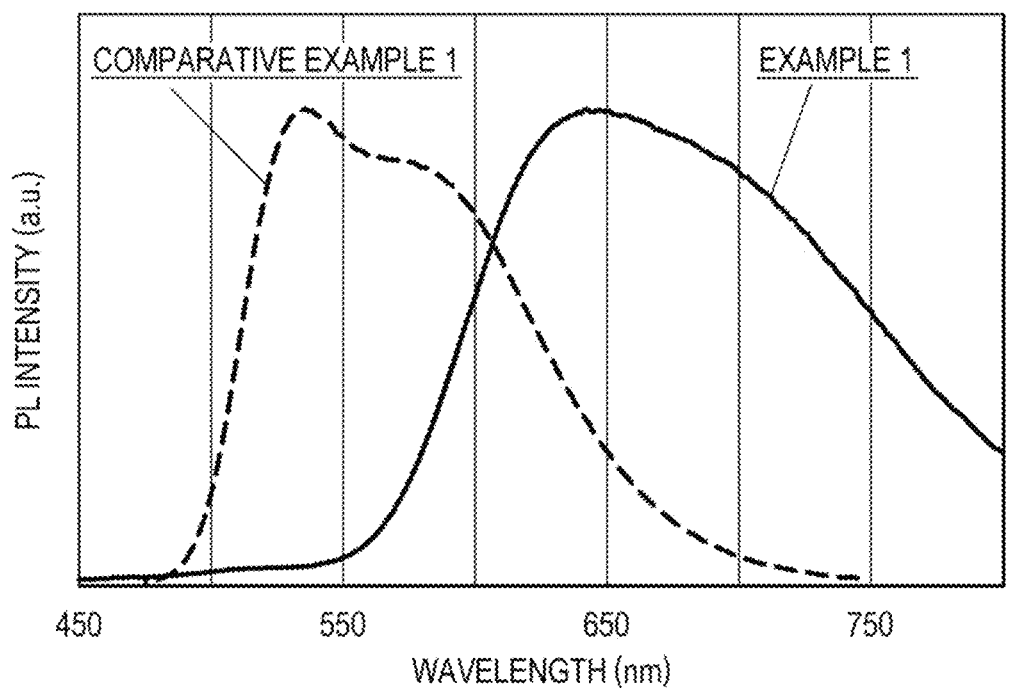
FIG. 15 is a graph of emission spectra of Example 1 and Comparative Example 1.
Figure 16:
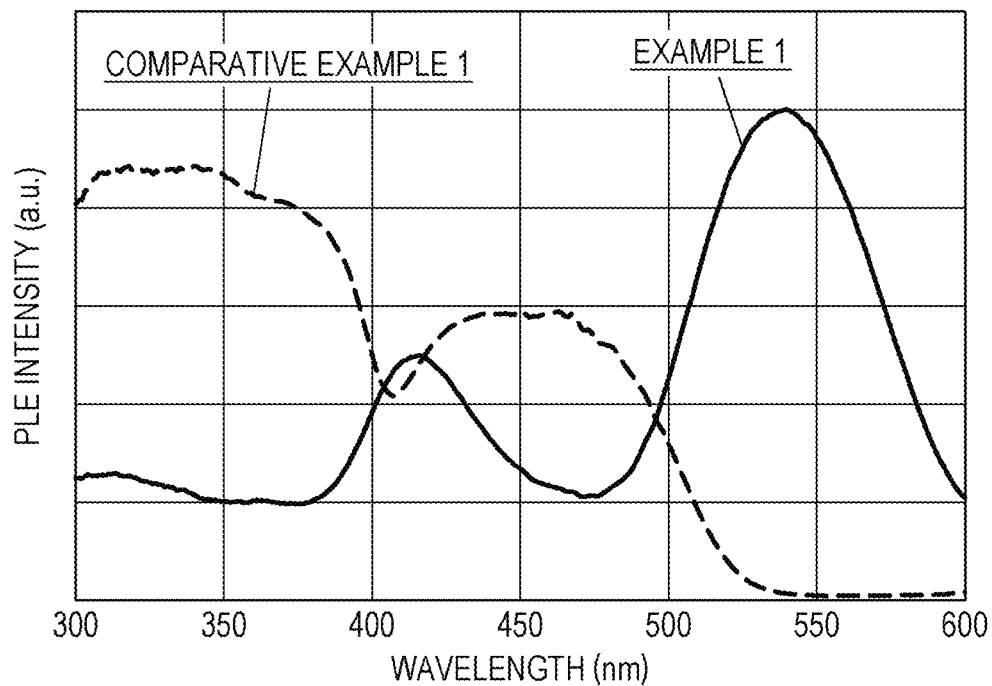
FIG. 16 is a graph of excitation spectra of Example 1 and Comparative Example 1.

The emission spectra and excitation spectra of Examples 1 to 4 and Comparative Example 1 were measured with a spectrofluorophotometer (FP-6500 manufactured by JASCO Corporation). FIG. 15 shows the emission spectra of Example 1 and Comparative Example 1. FIG. 16 shows the excitation spectra of Example 1 and Comparative Example 1. Table 4 lists the emission peak wavelength in the range of 450 to 800 nm and the excitation peak wavelength in the range of 400 to 600 nm. A Xe lamp was used as an excitation light source. The emission spectrum was measured while the excitation peak wavelength of each sample listed in Table 4 was used as the wavelength of the excitation light source. The excitation spectrum was measured while the emission peak wavelength of each sample listed in Table 4 was used as the monitor wavelength.

Comparative Example 1 containing no AlN in the starting materials emitted yellow light with an emission peak wavelength of 536 nm. The excitation peak wavelength was 450 nm. It is generally known that a phosphor crystal represented by $La_3Si_6N_{11}$ doped with Ce has an emission peak (approximately 535 nm) on the short wavelength side and an emission peak (approximately 580 nm) on the long wavelength side. These are almost the same as the emission peak on the short wavelength side and the emission peak on the long wavelength side of the phosphor described in Japanese Patent No. 4459941. The position of the excitation peak wavelength was also almost the same as in Japanese Patent No. 4459941.

Examples 1 to 4 emitted red light with an emission peak wavelength of approximately 640 nm. It was found that Examples 1 to 4 had an excitation peak at a wavelength of approximately 540 nm. These demonstrate that Examples 1 to 4 had different light-emitting properties from those of Comparative Example 1. Examples 1 to 4 had an additional excitation spectrum peak in the wavelength range of 350 nm or more and less than 500 nm.

<Evaluation of Emission Lifetime>

Figure 17:
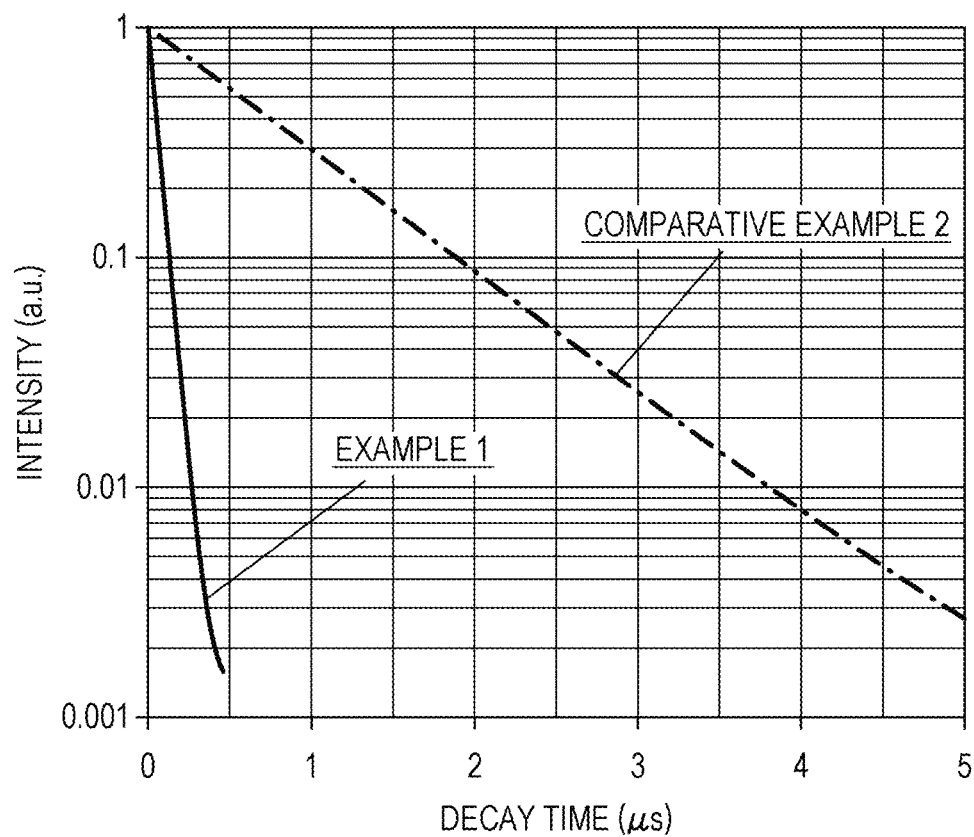
FIG. 17 is a graph of afterglow spectra of Example 1 and Comparative Example 2.

The emission lifetimes of Examples 1 to 4 and Comparative Examples 1 and 2 were measured with a fluorescence lifetime measuring apparatus (Quantaurus-Tau compact fluorescence lifetime measurement system manufactured by Hamamatsu Photonics K. K.). FIG. 17 shows the afterglow spectra of Example 1 and Comparative Example 2, wherein emission intensity changes are plotted as a function of time after the excitation light is blocked. Table 5 lists the 1/e emission lifetimes of Examples 1 to 4 and Comparative Examples 1 and 2.

TABLE 5

|  | 1/e emission lifetime |
| --- | --- |
| Example 1 | 54 ns |
| Example 2 | 55 ns |
| Example 3 | 54 ns |
| Example 4 | 53 ns |
| Comparative example 1 | 42 ns |
| Comparative example 2 | 820 ns |

Example 1 had a 1/e emission lifetime of 54 ns. Examples 1 to 4 and Comparative Example 1 had a 1/e emission lifetime of approximately 50 ns, thus confirming that the 1/e emission lifetime is 100 ns or less. It is known that the emission lifetime of Ce generally ranges from approximately 10 to 100 ns. Thus, the light emission in Examples 1 to 4 and Comparative Example 1 is probably emitted from Ce.

CASN:Eu of Comparative Example 2 had an emission lifetime of 820 ns. The emission lifetime has an influence on the luminance saturation characteristics. It is known that as compared with phosphors containing Ce, phosphors containing Eu are more likely to reach luminance saturation due to a decrease in quantum efficiency during high-energy excitation. The phosphors of Examples 1 to 4 and Comparative Example 1 have much shorter emission lifetimes than CASN:Eu and are less likely to reach luminance saturation. Thus, the phosphors of Examples 1 to 4 and Comparative Example 1 in combination with a high-power excitation light source can provide a high-power light-emitting device.

<Evaluation of Crystal Structure>

The X-ray powder diffraction patterns of Examples 1 to 4 and Comparative Example 1 were measured with an X-ray diffractometer (RINT2100 manufactured by Rigaku). The measurement was performed with Cu-Kα radiation under the conditions listed in Table 6.

TABLE 6

| Start angle | Final angle | Sampling width | Scanning speed | Tube voltage | Tube current | Divergence slit | Scattering slit | Light-receiving slit |
| --- | --- | --- | --- | --- | --- | --- | --- | --- |
| 10° | 60° | 0.02° | 4°/min | 40 kV | 40 mA | 1° | 1° | 0.15 mm |

Figure 18:
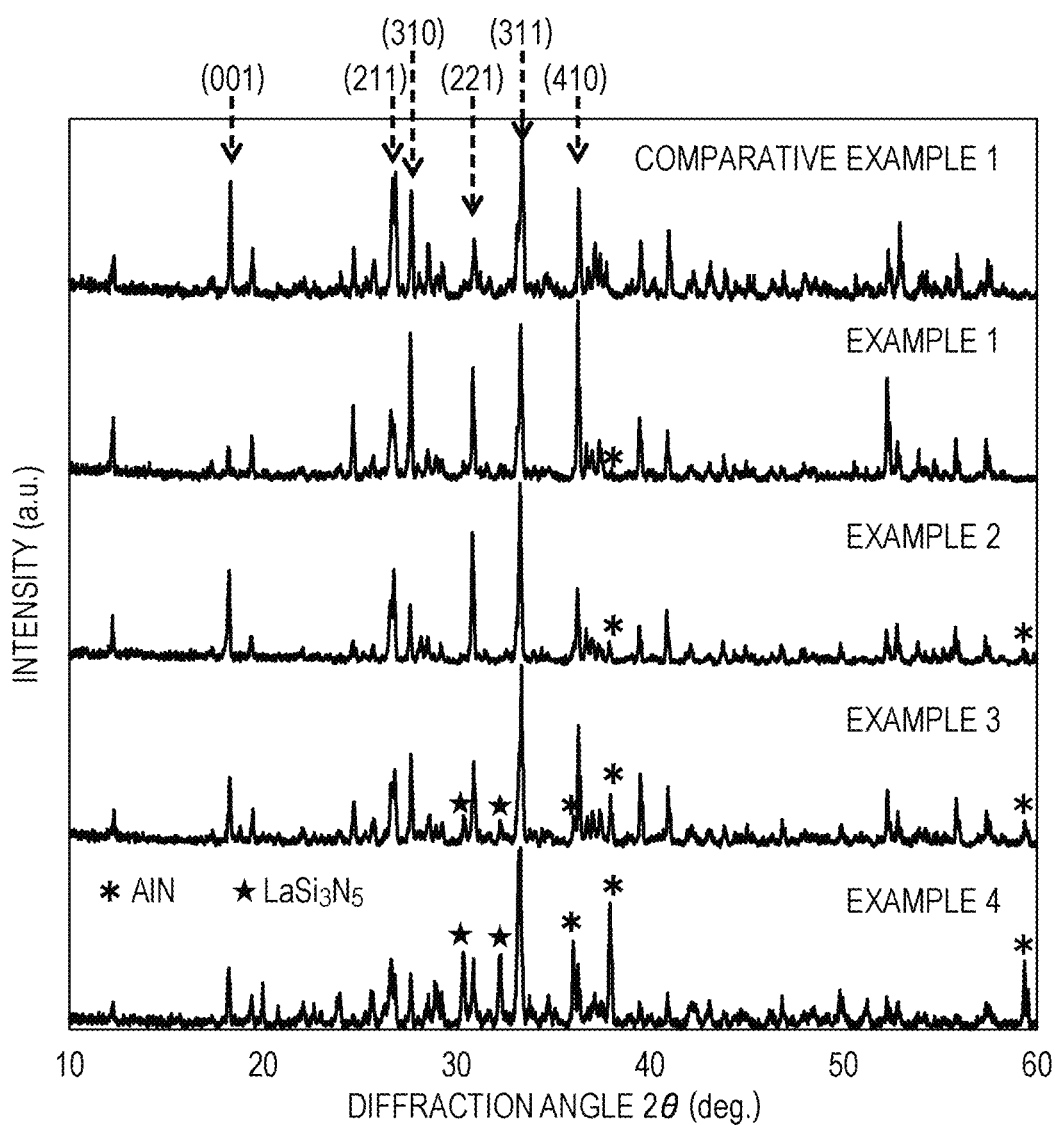
FIG. 18 is a graph of XRD diffraction patterns of Examples 1 to 4 and Comparative Example 1.
Figure 19A:
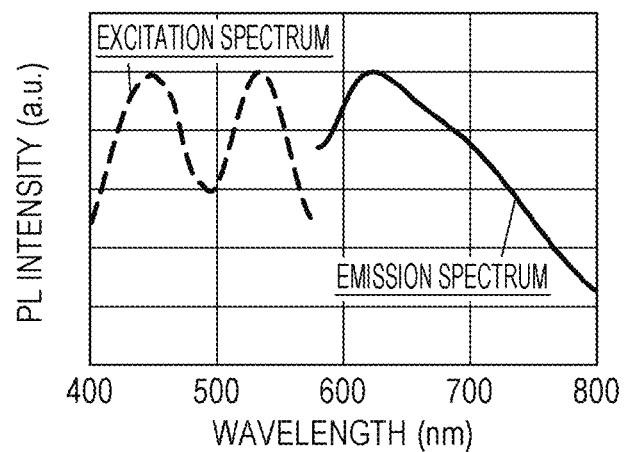
FIG. 19A is a graph of an emission spectrum and an excitation spectrum of Example 5.
Figure 19B:
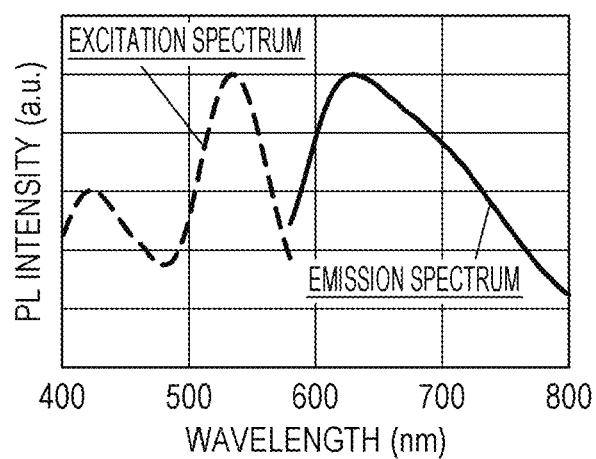
FIG. 19B is a graph of an emission spectrum and an excitation spectrum of Example 6.
Figure 19C:
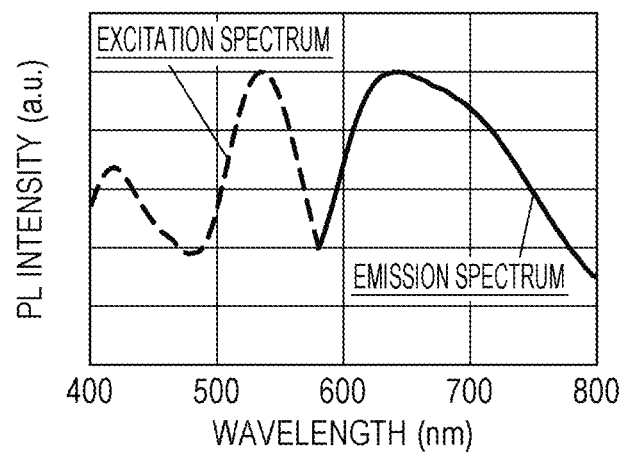
FIG. 19C is a graph of an emission spectrum and an excitation spectrum of Example 7.
Figure 19D:
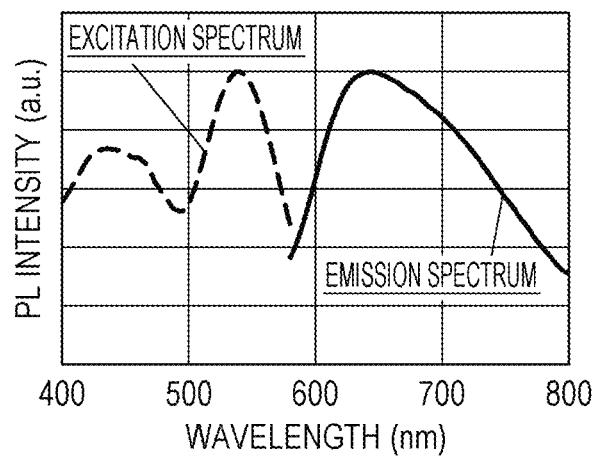
FIG. 19D is a graph of an emission spectrum and an excitation spectrum of Example 8.
Figure 19E:
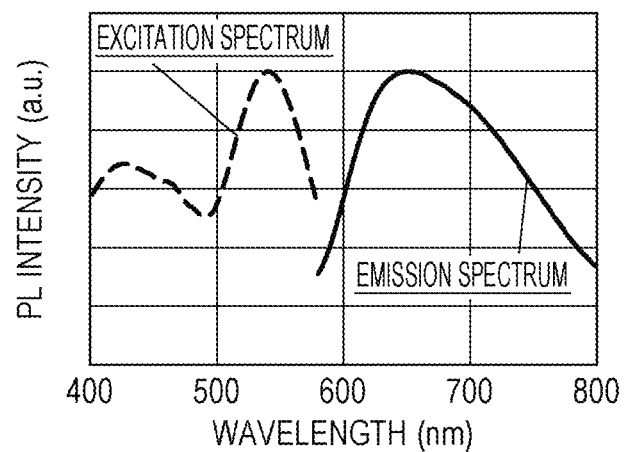
FIG. 19E is a graph of an emission spectrum and an excitation spectrum of Example 9.
Figure 19F:
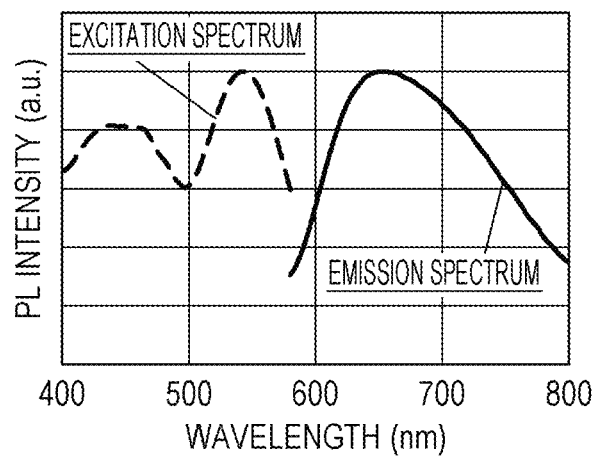
FIG. 19F is a graph of an emission spectrum and an excitation spectrum of Example 10.

FIG. 18 shows the X-ray diffraction patterns. FIG. 18 shows that although the X-ray diffraction patterns of Examples 1 to 4 slightly shift to the low angle side relative to the X-ray diffraction pattern of Comparative Example 1, these X-ray diffraction patterns are almost the same.

Among the diffraction peaks, six diffraction peaks corresponding to the $La_3Si_6N_{11}$ crystal type are designated as peaks 1 to 6 from the low angle side. Table 7 lists 2θ of each of the diffraction peaks.

TABLE 7

|  | Peak 1 | Peak 2 | Peak 3 | Peak 4 | Peak 5 | Peak 6 |
| --- | --- | --- | --- | --- | --- | --- |
| Example 1 | 18.20° | 26.62° | 27.60° | 30.84° | 33.30° | 36.26° |
| Example 2 | 18.24° | 26.76° | 27.60° | 30.82° | 33.28° | 36.24° |
| Example 3 | 18.28° | 26.80° | 27.64° | 30.88° | 33.36° | 36.30° |
| Example 4 | 18.24° | 26.62° | 27.64° | 30.88° | 33.30° | 36.04° |
| Comparative example 1 | 18.32° | 26.84° | 27.68° | 30.90° | 33.38° | 36.30° |

Table 7 shows that the X-ray diffraction patterns of the phosphors had diffraction peaks in the range of (1) 2θ=17.8 to 18.8 degrees, (2) 2θ=26.2 to 27.2 degrees, (3) 2θ=27.2 to 28.2 degrees, (4) 2θ=30.5 to 31.5 degrees, (5) 2θ=32.8 to 33.8 degrees, and (6) 2θ=35.8 to 36.8 degrees, corresponding to the peaks 1 to 6, respectively. The peaks 1 to 6 had Miller indices of (001), (211), (310), (221), (311), and (410), respectively. Furthermore, FIG. 18 shows that the diffraction intensity of the diffraction peak corresponding to AlN or $LaSi_3N_5$ increases with the amount of AlN added. For AlN, this is probably because AlN added remained unreacted. For $LaSi_3N_5$, this is probably because a deviation from the stoichiometry composition of the $La_3Si_6N_{11}$ crystal facilitated the formation of the $LaSi_3N_5$ phase.

The space group of the phosphor of Example 1 was analyzed with a single-crystal X-ray structure analyzer (VariMax manufactured by Rigaku). As a result, it was found that the space group was a tetragonal crystal. Thus, Examples 1 to 4 and Comparative Example 1 have almost the same crystal structure as a crystal represented by the general formula $La_3Si_6N_{11}$.

EXAMPLES 5 TO 10

A method for producing a phosphor will be described below. A LaN powder, a $Si_3N_4$ powder, an AlN powder, and a CeN powder were prepared as starting materials. First, the LaN powder, the $Si_3N_4$ powder, and the CeN powder were weighed and mixed at a composition represented by the general formula $La_{3-x}Ce_xSi_6N_{11}$. The amount of the LaN powder was 24% more than the theoretical value. The mixed powder was mixed with the AlN powder. The mixing method was dry blending with a mortar in a glove box in a nitrogen atmosphere. The mixed raw powders were placed in a boron nitride crucible. The raw powders were fired in a 0.5 MPa nitrogen atmosphere at 1900° C. for 2 hours. The fired sample was washed in a 10% nitric acid solution for 1 hour. Examples 5 to 10 were produced from the starting materials listed in Table 8 in this way.

TABLE 8

|  | LaN | Si$_3$N$_4$ | AlN | CeN | x | Emission peak wavelength | Excitation peak wavelength |
|---|---|---|---|---|---|---|---|
| Example 5 | 1.028 g | 0.505 g | 0.074 g | 0.004 g | 0.015 | 624 nm | 534 nm |
| Example 6 | 1.024 g | 0.505 g | 0.074 g | 0.008 g | 0.03 | 630 nm | 534 nm |
| Example 7 | 1.007 g | 0.505 g | 0.074 g | 0.025 g | 0.09 | 644 nm | 536 nm |
| Example 8 | 0.991 g | 0.505 g | 0.074 g | 0.042 g | 0.15 | 644 nm | 540 nm |
| Example 9 | 0.974 g | 0.505 g | 0.074 g | 0.058 g | 0.21 | 650 nm | 541 nm |
| Example 10 | 0.957 g | 0.504 g | 0.074 g | 0.075 g | 0.27 | 653 nm | 542 nm |

<Evaluation of Emission/Excitation Spectrum>

The emission spectra and excitation spectra of Examples 5 to 10 were measured with a spectrofluorophotometer (FP-6500 manufactured by JASCO Corporation). FIGS. 19A to 19F show the emission spectra and the excitation spectra of Examples 5 to 10, respectively. A Xe lamp was used as an excitation light source. The emission spectrum was measured while the excitation peak wavelength of each sample listed in Table 8 was used as the wavelength of the excitation light source. The excitation spectrum was measured while the emission peak wavelength of each sample listed in Table 8 was used as the monitor wavelength. All samples of Examples 5 to 10 emitted red light with an emission peak wavelength of 600 nm or more. The emission peak wavelength ranged from 624 to 653 nm.

All samples of Examples 5 to 10 had an excitation peak wavelength of 500 nm or more. The excitation peak wavelength ranged from 534 to 542 nm. An increase in the Ce concentration (x) of the phosphor results in an increase in overlap of the wave function of the excitation level between Ce atoms. This also results in an increase in excitation level energy width, formation of a band, and a decrease in energy difference from the ground level. Thus, an increase in Ce concentration caused a shift of the emission peak wavelength to the long wavelength side.

Examples 5 to 10 also had an additional excitation spectrum peak in the wavelength range of 350 nm or more and less than 500 nm.

<Evaluation of Internal Quantum Efficiency>

Figure 20:
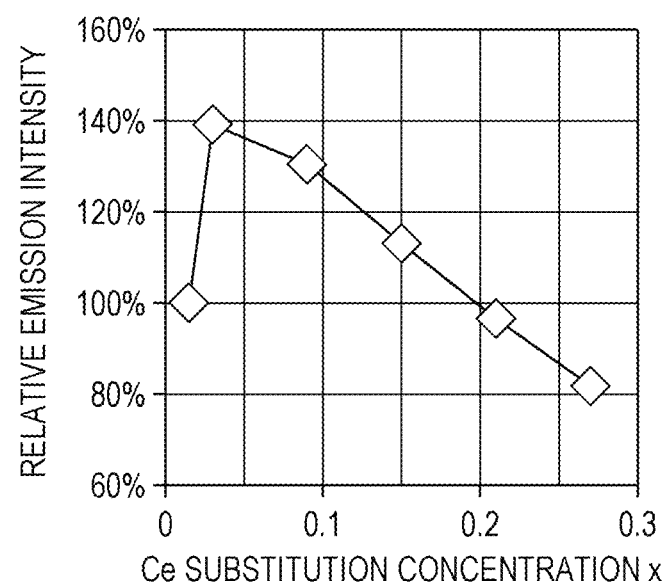
FIG. 20 is a graph showing the relationship between the Ce substitution concentration and the relative emission intensity of Examples 5 to 10.

The internal quantum efficiency (IQE) of Examples 5 to 10 was measured with an absolute PL quantum yield measurement system (C9920-02 manufactured by Hamamatsu Photonics K. K.). FIG. 20 shows the relative emission intensity of Examples 5 to 10. The relative emission intensity in the present example refers to the relative value of each sample with respect to the IQE of Example 5 (100%).

FIG. 20 shows that the relative emission intensity varies with the Ce concentration x of the phosphor. For example, at a Ce substitution concentration x of more than 0.03, the relative emission intensity decreases with increasing Ce substitution concentration x. This is probably due to concentration quenching. Since x is more than 0, Ce can emit light. FIG. 20 shows that x is desirably 0.015 or more, for example. The maximum value of x is not particularly limited as long as the phosphor can emit light. However, an excessively large x results in low emission intensity due to concentration quenching. Thus, x is desirably 0.6 or less. FIG. 20 shows that x is desirably 0.3 or less, more desirably 0.15 or less, for example. For example, at a Ce substitution concentration x in such a range, the phosphor can have higher emission intensity.

<Evaluation of Emission Lifetime>

The emission lifetimes of Examples 5 to 10 were measured with a fluorescence lifetime measuring apparatus (Quantaurus-Tau compact fluorescence lifetime measurement system manufactured by Hamamatsu Photonics K. K.). Table 9 lists the 1/e emission lifetimes of Examples 5 to 10.

TABLE 9

|  | 1/e emission lifetime |
|---|---|
| Example 5 | 64 ns |
| Example 6 | 60 ns |
| Example 7 | 56 ns |
| Example 8 | 49 ns |
| Example 9 | 45 ns |
| Example 10 | 42 ns |

In Examples 5 to 10, the 1/e emission lifetime was 100 ns or less. Thus, the phosphors of Examples 5 to 10 in combination with a high-power excitation light source can provide a high-power light-emitting device. An increase in Ce concentration facilitates energy transfer between adjacent Ce atoms and causes energy migration. During energy migration, an electron trapped in a crystal defect is relaxed by non-radiative transition. Thus, an increase in Ce concentration results in an increase in the non-luminescence (non-radiative transition) probability of an electron with a relatively low transition probability, thus resulting in a shorter emission lifetime.

<Evaluation of Crystal Structure>

The X-ray powder diffraction patterns of Examples 5 to 10 and Comparative Example 1 were measured with an X-ray diffractometer (RINT2100 manufactured by Rigaku). The measurement was performed with Cu-Kα radiation under the conditions listed in Table 10.

TABLE 10

| Start angle | Final angle | Sampling width | Scanning speed | Tube voltage | Tube current | Divergence slit | Scattering slit | Light-receiving slit |
|---|---|---|---|---|---|---|---|---|
| 10° | 60° | 0.01° | 1°/min | 40 kV | 40 mA | 1° | 1° | 0.15 mm |

Figure 21:
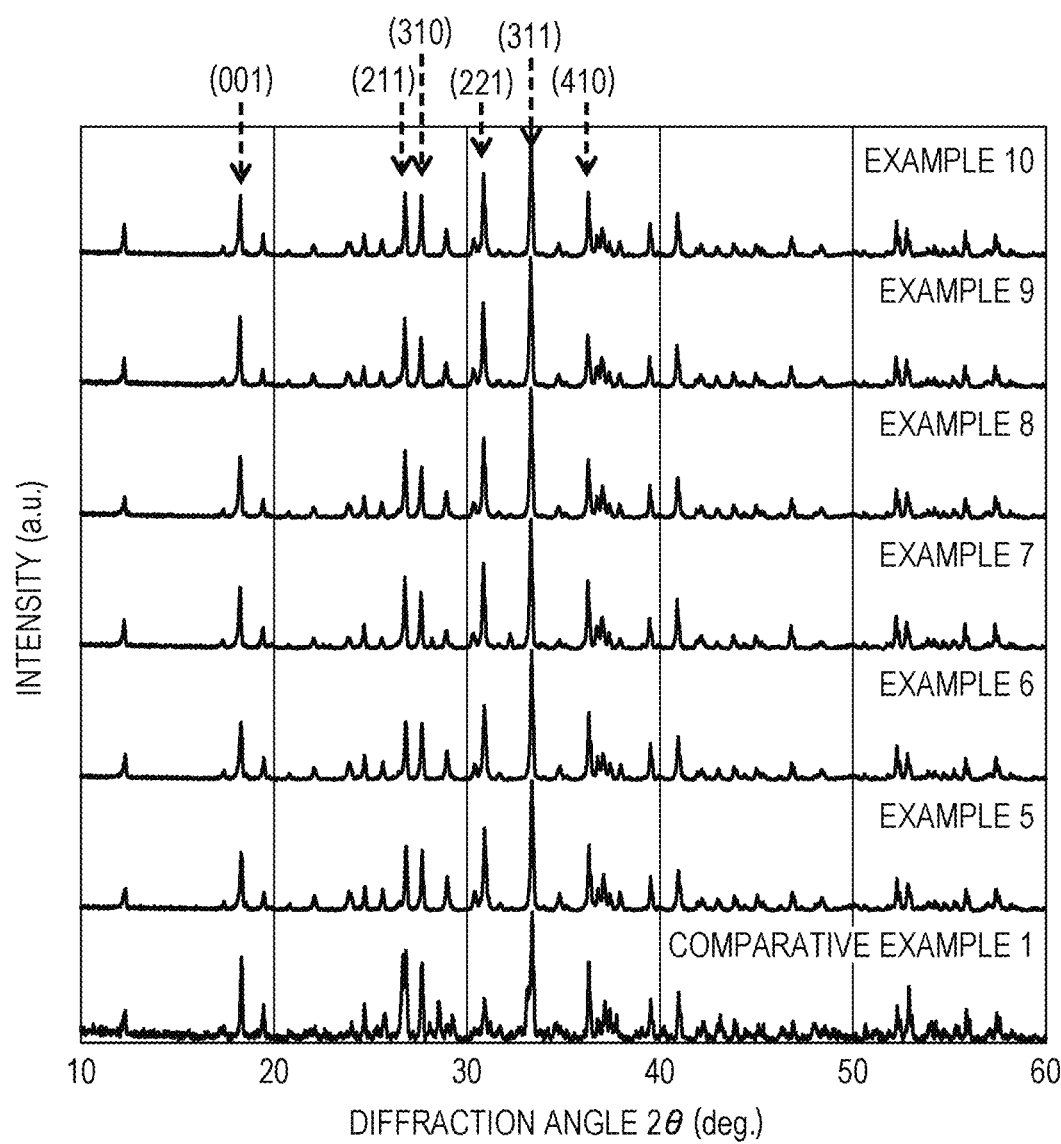
FIG. 21 is a graph of XRD diffraction patterns of Examples 5 to 10 and Comparative Example 1.

FIG. 21 shows measured X-ray diffraction patterns. Although the X-ray diffraction patterns of Examples 5 to 10 slightly shift to the low angle side relative to the X-ray diffraction pattern of Comparative Example 1, these X-ray diffraction patterns are almost the same.

Among the diffraction peaks, six diffraction peaks corresponding to the $La_3Si_6N_{11}$ crystal type are designated as peaks 1 to 6 from the low angle side. Table 11 lists 2θ of each of the diffraction peaks.

TABLE 11

|  | Peak 1 | Peak 2 | Peak 3 | Peak 4 | Peak 5 | Peak 6 |
| --- | --- | --- | --- | --- | --- | --- |
| Example 5 | 18.31° | 26.85° | 27.68° | 30.92° | 33.37° | 36.32° |
| Example 6 | 18.30° | 26.84° | 27.67° | 30.91° | 33.36° | 36.32° |
| Example 7 | 18.25° | 26.78° | 27.62° | 30.86° | 33.32° | 36.27° |
| Example 8 | 18.25° | 26.80° | 27.65° | 30.86° | 33.31° | 36.29° |
| Example 9 | 18.24° | 26.78° | 27.61° | 30.84° | 33.30° | 36.27° |
| Example 10 | 18.26° | 26.81° | 27.64° | 30.87° | 33.33° | 36.29° |

Table 11 shows that the X-ray diffraction patterns of the phosphors had diffraction peaks in the range of (1) 2θ=17.8 to 18.8 degrees, (2) 2θ=26.2 to 27.2 degrees, (3) 2θ=27.2 to 28.2 degrees, (4) 2θ=30.5 to 31.5 degrees, (5) 2θ=32.8 to 33.8 degrees, and (6) 2θ=35.8 to 36.8 degrees, corresponding to the peaks 1 to 6, respectively. The peaks 1 to 6 had Miller indices of (001), (211), (310), (221), (311), and (410), respectively. These results show that the space group of the phosphors of Examples 5 to 10 is a tetragonal crystal, as in Examples 1 to 4 and Comparative Example 1, and has almost the same crystal structure as a crystal represented by the general formula $La_3Si_6N_{11}$.

EXAMPLE 11 AND COMPARATIVE EXAMPLE 3

A method for producing a phosphor will be described below. A LaN powder, a $Si_3Na$ powder, an AlN powder, and a CeN powder were prepared as starting materials. First, the LaN powder, the $Si_3Na$ powder, and the CeN powder were weighed and mixed at a composition represented by the general formula $La_{3-x}Ce_xSi_6N_{11}$. The amount of the LaN powder was 24% more than the theoretical value. The mixed powder was mixed with the AlN powder. The mixing method was dry blending with a mortar in a glove box in a nitrogen atmosphere. The mixed raw powders were placed in a boron nitride crucible. The raw powders were fired in a 0.5 MPa nitrogen atmosphere at 1900° C. for 2 hours. The fired sample was washed in a 3% hydrochloric acid solution for 24 hours. Example 11 and Comparative Example 3 were produced from the starting materials listed in Table 12 in this way.

As in Examples 1 to 10, red-light emission with an emission peak wavelength of 600 nm or more was observed in Example 11. The excitation peak wavelength was 500 nm or more.

TABLE 12

|  | LaN | $Si_3N_4$ | AlN | CeN | x | Emission peak wavelength | Excitation peak wavelength |
| --- | --- | --- | --- | --- | --- | --- | --- |
| Example 11 | 6.271 g | 3.305 g | 0.483 g | 0.490 g | 0.27 | 642 nm | 531 nm |
| Comparative example 3 | 6.271 g | 3.305 g | 0 g | 0.490 g | 0.27 | 536 nm | 450 nm |

<Evaluation of Emission Lifetime>

The emission lifetimes of Example 11 and Comparative Example 3 were measured with a fluorescence lifetime measuring apparatus (Quantaurus-Tau compact fluorescence lifetime measurement system manufactured by Hamamatsu Photonics K.K.). Table 13 lists the 1/e emission lifetimes of Example 11 and Comparative Example 3.

TABLE 13

|  | 1/e emission lifetime |
| --- | --- |
| Example 11 | 49 ns |
| Comparative example 3 | 38 ns |

In Example 11, the 1/e emission lifetime was 100 ns or less.

<Evaluation of Crystal Structure>

Figure 22A:
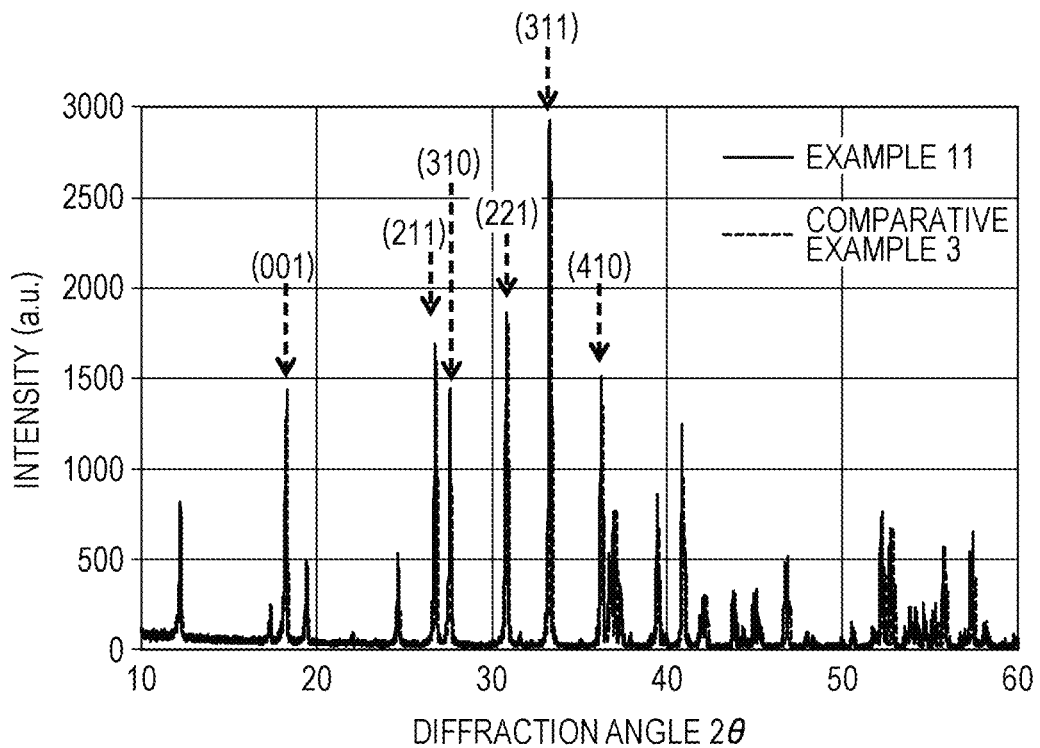
FIG. 22A is a graph of XRD diffraction patterns of Example 11 and Comparative Example 3.
Figure 22B:
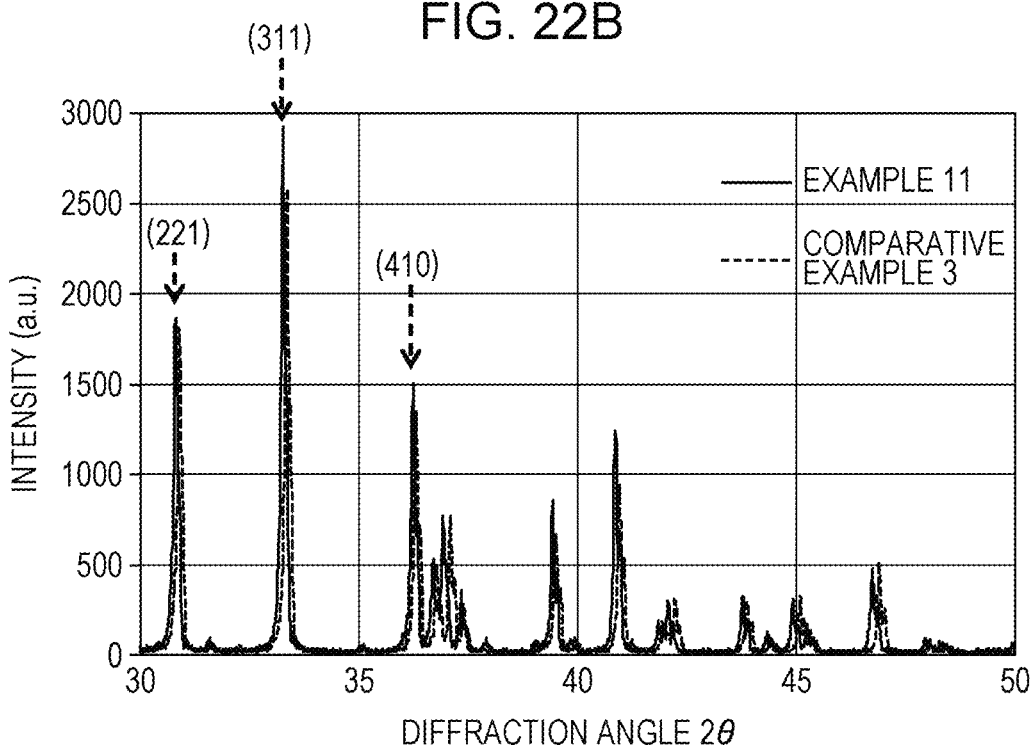
FIG. 22B is a graph of enlarged XRD diffraction patterns of Example 11 and Comparative Example 3.

The X-ray powder diffraction patterns of Example 11 and Comparative Example 3 were measured with an X-ray diffractometer (RINT2100 manufactured by Rigaku). The measurement was performed with Cu-Kα radiation under the conditions listed above in Table 12. FIGS. 22A and 22B show measured X-ray diffraction patterns.

The X-ray diffraction pattern of Example 11 was almost the same as the X-ray diffraction pattern of Comparative Example 3. The X-ray diffraction peaks in Example 11 shift slightly to the low-angle side with respect to the X-ray diffraction peaks in Comparative Example 3.

Among the diffraction peaks, six diffraction peaks corresponding to the $La_3Si_6N_{11}$ crystal type are designated as peaks 1 to 6 from the low angle side. Table 14 lists 2θ of each of the diffraction peaks.

TABLE 14

|  | Peak 1 | Peak 2 | Peak 3 | Peak 4 | Peak 5 | Peak 6 |
| --- | --- | --- | --- | --- | --- | --- |
| Example 11 | 18.23° | 26.75° | 27.60° | 30.82° | 33.28° | 36.25° |
| Comparative example 3 | 18.30° | 26.84° | 27.66° | 30.91° | 33.37° | 36.32° |

Table 14 shows that the X-ray diffraction patterns of the phosphors had diffraction peaks in the range of (1) 2θ=17.8 to 18.8 degrees, (2) 2θ=26.2 to 27.2 degrees, (3) 2θ=27.2 to 28.2 degrees, (4) 2θ=30.5 to 31.5 degrees, (5) 2θ=32.8 to 33.8 degrees, and (6) 2θ=35.8 to 36.8 degrees, corresponding to the peaks 1 to 6, respectively. The peaks 1 to 6 had Miller indices of (001), (211), (310), (221), (311), and (410), respectively. These results show that the space group of the phosphor of Example 11 is a tetragonal crystal, as in Examples 1 to 10 and Comparative Examples 1 and 3, and has almost the same crystal structure as a crystal represented by the general formula $La_3Si_6N_{11}$.

<Evaluation of Composition>

The composition analysis of Example 11 and Comparative Example 3 was performed by inductively coupled plasma-atomic emission spectrometry (ICP-AES). Pretreatment for measurement will be described below. After alkali fusion with sodium peroxide, the melt was dissolved in hydrochloric acid and was diluted with pure water to determine the Si content. After alkali fusion with lithium tetraborate and sodium carbonate, the melt was dissolved in hydrochloric acid and was diluted with pure water to determine the La, Al, and Ce contents. Table 15 shows the results.

TABLE 15

|  | La | Ce | Al | Si |
|---|---|---|---|---|
| Example 11 | 48.5 mass % | 4.00 mass % | 4.89 mass % | 20.5 mass % |
| Comparative example 3 | 50.6 mass % | 4.26 mass % | 0 mass % | 23.1 mass % |

Table 15 shows that Example 11 contained Al.
Table 16 lists the mole fraction of each element when the total Al and Si content is assumed to be 6 mol.

TABLE 16

|  | La | Ce | Al | Si |
|---|---|---|---|---|
| Example 11 | 2.30 mol | 0.19 mol | 1.19 mol | 4.81 mol |
| Comparative example 3 | 2.66 mol | 0.22 mol | 0 mol | 6 mol |

Table 16 shows that the total La and Ce content of each sample of Example 11 and Comparative Example 3 is smaller than the stoichiometric composition (3 mol). This is probably because the starting materials LaN and CeN are decomposed during firing. As long as light can be emitted, La and Ce may be less than the stoichiometric composition. For example, the total La and Ce content may be in a range of 2 to 3 mol.

The nitrogen and oxygen contents were then measured. The samples of Example 11 and Comparative Example 3 were melted at 2300° C. in an inert gas. The oxygen content was measured by a non-dispersive infrared absorption method (NDIR). The nitrogen content was measured by a thermal conductivity method (TCD). Table 17 shows the results.

TABLE 17

|  | O | N |
|---|---|---|
| Example 11 | 0.5 mass % | 21.4 mass % |
| Comparative example 3 | 1.4 mass % | 20.6 mass % |

Table 17 shows that the sample of Example 11 contained O. As long as light can be emitted, O may be contained. Because it is difficult to simultaneously absolutely quantify anions and cations, the absolute value of each element content in Tables 15 to 17 includes an error. Thus, the composition of a phosphor of the present disclosure is not limited to the absolute value of each element content listed in Tables 15 to 17.

<Evaluation of Local Structure of Ce Ligand>

The local structure of each Ce ligand of Example 11 and Comparative Example 3 was analyzed by X-ray absorption fine structure spectroscopy (XAFS). The XAFS measurement was performed in National Research and Development Agency RIKEN (the Institute of Physical and Chemical Research), SPring 8 beam line 16B2.

Pretreatment for measurement will be described below. 0.16 g of the sample of Example 11 was mixed with 0.01 g of a BN powder in a mortar and was formed into pellets 8 mm in diameter using a mold. Likewise, 0.16 g of the sample of Comparative Example 3 was mixed with 0.01 g of a BN powder in a mortar and was formed into pellets 8 mm in diameter using a mold. An absorption spectrum near the K absorption edge of Ce was measured to determine the local structure of Ce and a ligand around the Ce. Extended X-ray absorption fine structure (EXAFS) oscillations were analyzed using open source EXAFS analysis software Athena to determine the radial distribution function around the Ce atom.

Table 18 lists the analysis parameters.

TABLE 18

| Background removal parameters | |
|---|---|
| E0 | 40463.755 |
| Algorithm | autobk |
| Rbkg | 1.000 |
| k-weight | 2 |
| Normalization order | 3 |
| Pre-edge range | [−150.000:−75.000] |
| Normalization range | [150.000:1400.778] |
| Spline range (k) | [0.000:12.000] |
| Spline range (E) | [0.000:548.638] |
| Edge step | 3.64E−01 |
| Standard | None |
| Lower clamp | None |
| Upper clamp | Strong |
| Forward Fourier transform parameters | |
| k-range | [3.000:17.847] |
| dk | 1.000 |
| Window | hanning |
| Arb. kw | 0.5 |
| Phase correction | no |
| Backward Fourier transform parameters | |
| R-range | [1.000:3.000] |
| dR | 0.000 |
| Window | hanning |
| Plotting parameters | |
| Plot multiplier | 1.00E+00 |
| y offset | 0.000 |

Figure 23:
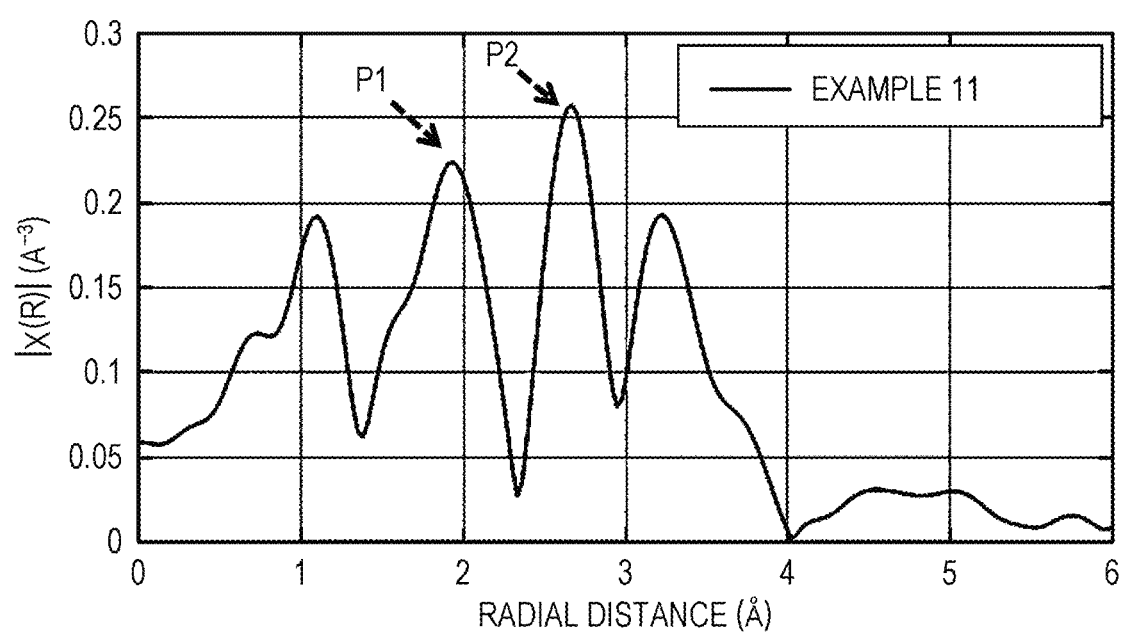
FIG. 23 is a graph of the radial distribution function around a Ce atom in Example 11.
Figure 24:
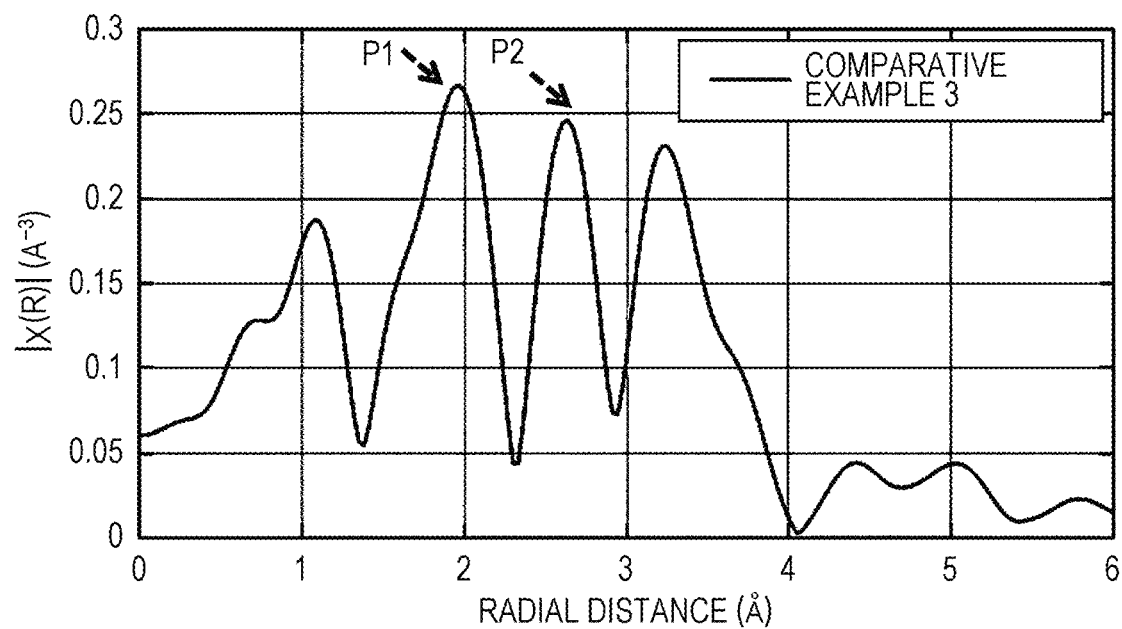
FIG. 24 is a graph of the radial distribution function around a Ce atom in Comparative Example 3.

FIG. 23 is a graph of the radial distribution function of Example 11. FIG. 24 is a graph of the radial distribution function of Comparative Example 3. In general, the horizontal axis (radial distance) of the radial distribution function corresponds to the distance to an adjacent atom. The vertical axis (peak height) represents the coordination number n. In FIGS. 23 and 24, the peak at approximately 1.1 angstroms is a ghost peak due to measurement signal noise. The peak at approximately 1.9 angstroms (P1) is a peak of the first neighbor shell of Ce. The peak at approximately 2.6 angstroms (P2) is a peak of the second neighbor shell of Ce. The peak at approximately 3.3 angstroms is a peak of the third neighbor shell of Ce.

As is clear from FIG. 24, in Comparative Example 3, the peak (P1) height of the first neighbor shell is higher than the peak (P2) height of the second neighbor shell. As is clear from FIG. 23, in Example 11, the peak (P1) height of the first neighbor shell is lower than the peak (P2) height of the second neighbor shell (approximately 0.84 times). The P2 height in Example 11 is almost the same as the P2 height in Comparative Example 3. On the other hand, the P1 height in Example 11 is obviously lower than the P1 height in Comparative Example 3.

These results show that the coordination number of the first neighbor shell of Ce in Example 11 is smaller than the coordination number of the first neighbor shell of Ce in Comparative Example 3.

The radial distribution functions in FIGS. 23 and 24 were analyzed with respect to the coordination atoms using open source EXAFS analysis software Artemis. It was found that both the Ce atom in Example 11 and the Ce atom in Comparative Example 3 are substituted for La at an A site of the crystal structure. It was also found that eight nitrogen atoms are coordinated to the first neighbor shell of Ce in Comparative Example 3, but only seven nitrogen atoms are coordinated to the first neighbor shell of Ce in Example 11.

These results show that the coordination structure around Ce in Comparative Example 3 includes coordination of eight nitrogen atoms as in an A site of La in $La_3Si_6N_{11}$ and has relatively high symmetry. It was also found that the coordination structure around Ce in Example 11 has a nitrogen defect around an A site of La in $La_3Si_6N_{11}$ and is a coordination structure of seven coordination with low symmetry.

Thus, in Example 11, low symmetry of the coordination structure around Ce, for example, due to a Frenkel defect probably resulted in large splitting of the 5d orbital and a decreased energy difference from the 4f orbital. This increased the emission wavelength and provided a Ce phosphor that can emit red light.

The phosphors of Examples 1 to 11 had almost the same crystal structure as a crystal represented by the general formula $La_3Si_6N_{11}$ but emitted red light with a longer wavelength than light emitted from known LSN:Ce yellow phosphors. Although the reason for this is not clear, for example, the following is a possible reason. The phosphors of Examples 1 to 11 might have emitted red light, unlike known phosphors, due to Al (for example, an AlN powder) contained in the raw materials. The phosphors of Examples 1 to 11 might have emitted red light, for example, because the phosphors have a crystal structure including substitution of Ce for part of the A sites of La in the $La_3Si_6N_{11}$ crystal, substitution of Al for part of Si around Ce (or substitution of Al—O for part of Si—N), and a loss of part of N.

<Fiber Light Source>

The fiber light source of the first embodiment will be described below. As described above, the fiber light source of the first embodiment includes the solid-state light source, the wavelength convertor, which converts the wavelength of output light emitted from the solid-state light source, and the optical fiber.

The solid-state light source emits at least blue light and green light. The blue light has a peak wavelength in the range of 430 to 470 nm. The green light has a peak wavelength in the range of 480 to 550 nm, desirably 510 to 540 nm.

The solid-state light source is a LED or LD, for example. The solid-state light source may be a GaN LED or LD, desirably a GaN LD. The solid-state light source may include a GaN semiconductor laser that emits blue light and a YAG:Nd solid-state laser that emits green light and that includes a second harmonic generator.

The solid-state light source may include a blue laser that emits blue light and a green laser that emits green light. In this case, the fiber light source of the present embodiment may further include a dichroic mirror by which blue light and green light are coaxially multiplexed to be incident on the fiber. The term "coaxially multiplex", as used herein, refers to mixing of light beams such that the light beams have the same central axis.

The wavelength convertor contains at least a red phosphor including Ce as a luminescent center. The red phosphor including the Ce luminescent center has been described in detail above.

The wavelength convertor in the present embodiment may include a plurality of phosphor layers. In this case, a phosphor layer of the phosphor layers closest to the light incident side may contain the red phosphor including the Ce luminescent center. The wavelength convertor may include a first phosphor layer containing at least a red phosphor including Ce as a luminescent center and a second phosphor layer containing a yellow phosphor and/or a green phosphor.

The first phosphor layer may be closer to the light incident side than the second phosphor layer. A phosphor in the second phosphor layer is a phosphor containing a crystal phase having the chemical composition $Y_3Al_5O_{12}$:Ce (YAG: Ce) or a phosphor containing a crystal phase having the chemical composition $La_3Si_6N_{11}$:Ce (LSN:Ce), for example.

As described above, the fiber light source of the present embodiment includes the solid-state light source that emits blue light and green light and the red phosphor including the Ce luminescent center, unlike known fiber light sources. The red phosphor including the Ce luminescent center is less likely to reach luminance saturation even when excited by strong excitation light. Thus, the red phosphor in the present embodiment can be excited even by a laser beam with a high energy density. Thus, the fiber light source of the present embodiment can include a light source that emits light with a high light power density, such as a LD device, as a solid-state light source. Consequently, the present embodiment can provide a compact high-power fiber light source. Containing the red phosphor including the Ce luminescent center, the fiber light source of the present embodiment can control the color of output light using at least blue light and green light of a light source and red light emitted from the phosphor. Thus, the fiber light source of the present embodiment has high color controllability.

The red phosphor including the Ce luminescent center in the wavelength convertor in the present embodiment may have a 1/e emission lifetime of 100 ns or less. The emission lifetime has an influence on the luminance saturation characteristics. Phosphors containing Eu, such as a known red phosphor CASN:Eu, have a longer emission lifetime than phosphors containing Ce. Thus, phosphors containing Eu are likely to reach luminance saturation due to a decrease in quantum efficiency during high-energy excitation. Thus, the red phosphor including the Ce luminescent center is expected to be a red phosphor with higher quantum efficiency than known red phosphors even at high power. Each of all phosphors in the wavelength convertor in the present embodiment may have a 1/e emission lifetime of 100 ns or less. In this case, the wavelength convertor does not contain a phosphor that has decreased emission quantum efficiency when excited by high-power light and therefore can further increase the power of the fiber light source of the present embodiment.

In the fiber light source of the present embodiment, the wavelength convertor may be disposed on the light incident side of the optical fiber or on the light output side of the optical fiber. The position of the wavelength convertor can be appropriately determined for each application of the fiber light source.

For the fiber light source of the present embodiment including the wavelength convertor disposed on the light incident side of the optical fiber, output light from the solid-state light source is incident on the wavelength convertor and is subjected to wavelength conversion. Light subjected to wavelength conversion in the wavelength convertor and light passing through the wavelength convertor without wavelength conversion are incident on the optical fiber, are transmitted through the optical fiber to a target position, and are emitted from the fiber light source. In this structure, the fiber light source of the present embodiment may further include a condenser lens on the optical path between the wavelength convertor and the light incident end of the optical fiber. In this structure, the fiber light source of the present embodiment may further include an objective lens on the light output side of the optical fiber.

In the fiber light source of the present embodiment including the wavelength convertor on the light output side of the optical fiber, output light from the solid-state light source is incident on the optical fiber and is transmitted through the optical fiber. Light from the optical fiber is incident on the wavelength convertor. Light incident on the wavelength convertor is subjected to wavelength conversion in the wavelength convertor. Light subjected to wavelength conversion in the wavelength convertor and light passing through the wavelength convertor without wavelength conversion are emitted from the fiber light source. In this structure, the fiber light source of the present embodiment may include a condenser lens on the optical path between the light output end of the optical fiber and the wavelength convertor. In this structure, the fiber light source of the present embodiment may further include an objective lens on the light output side of the wavelength convertor.

The fiber light source of the present embodiment may further include a coupler lens on the light incident side of the optical fiber. The coupler lens enables light to be incident on the optical fiber.

With such a structure, the fiber light source of the present embodiment has high power and high color controllability.

Second Embodiment

A second embodiment describes as an example of a fiber light source of the present disclosure a fiber lighting apparatus that includes a LD that emits blue light and another LD that emits green light as solid-state light sources.

Figure 25:
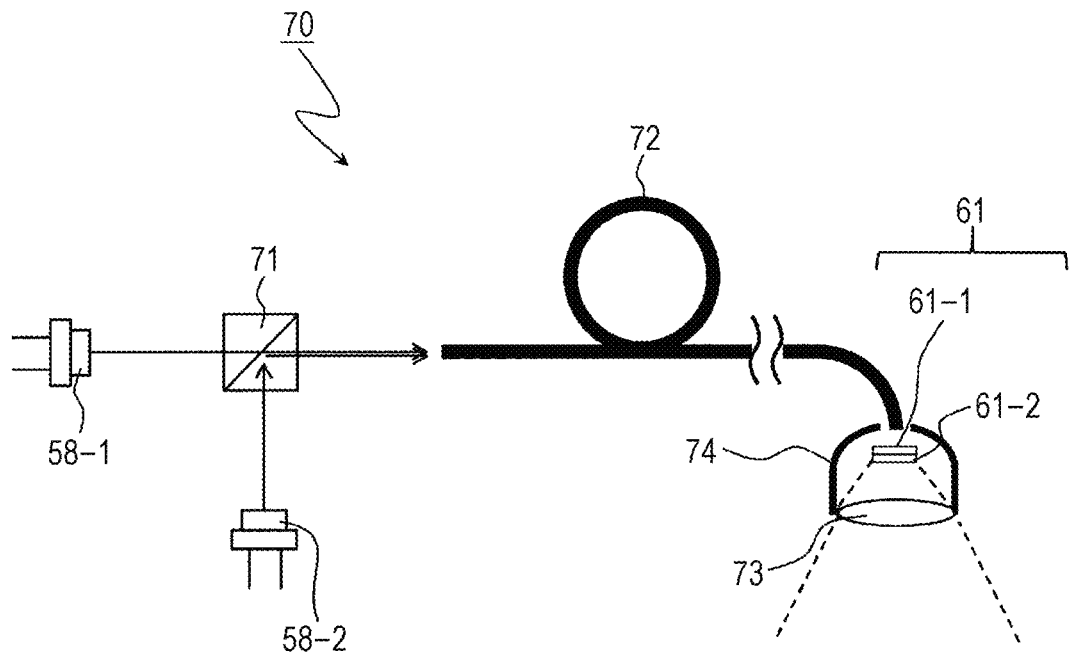
FIG. 25 is a schematic view of a fiber lighting apparatus according to a second embodiment.

FIG. 25 is a schematic view of a fiber lighting apparatus 70 according to the second embodiment.

The fiber lighting apparatus 70 includes a LD device 58-1 and a LD device 58-2 as solid-state light sources, a dichroic mirror 71, an optical fiber 72, a wavelength conversion member 61 as a wavelength convertor, an objective lens 73, and a housing 74.

The LD device 58-1 is a LD that emits blue light. The LD device 58-2 is a LD that emits green light. The LD device 58-1 emits light in a blue region and has an emission spectrum peak in the wavelength range of 430 to 470 nm. More specifically, the LD device 58-1 is a LD device that emits blue light. The LD device 58-1 may be a GaN semiconductor laser, that is, a GaN LD. The LD device 58-2 emits light in a green region and has an emission spectrum peak in the wavelength range of 480 to 550 nm, desirably 510 to 540 nm. More specifically, the LD device 58-2 is a LD device that emits green light. The LD device 58-2 may be a GaN semiconductor laser, that is, a GaN LD. The LD device 58-2 may also be a YAG: Nd solid-state laser with a second harmonic generator.

Blue light emitted from the LD device 58-1 and green light emitted from the LD device 58-2 are coaxially multiplexed by the dichroic mirror 71 and are incident on the optical fiber 72. Thus, the dichroic mirror 71 is disposed on the optical path between the LD devices 58-1 and 58-2 and the optical fiber 72. The optical path is a common optical path of blue light and green light.

The optical fiber 72 transmits incident light to a target position. In the fiber lighting apparatus 70 of the present embodiment, the optical fiber 72 transmits incident light to the wavelength conversion member 61 and emits incident light to the wavelength conversion member 61.

The wavelength conversion member 61 has a layered structure composed of a first phosphor layer 61-1 containing a red phosphor including Ce as a luminescent center and a second phosphor layer 61-2 containing a yellow-green phosphor. In the wavelength conversion member 61 in the present embodiment, the first phosphor layer 61-1 is disposed on the light incident side. The red phosphor including the Ce luminescent center is described in the first embodiment and is not described in detail here. For example, the yellow-green phosphor is a phosphor including a Ce luminescent center, such as YAG:Ce. The red phosphor in the first phosphor layer 61-1 is excited by green light and emits red light. The yellow-green phosphor in the second phosphor layer 61-2 is excited by blue light and emits yellow-green light. Thus, these phosphors convert output light emitted from the LD device 58-1 and the LD device 58-2 to light with a longer wavelength.

The operation of the fiber lighting apparatus 70 of the present embodiment will be described below. Blue light emitted from the LD device 58-1 and green light emitted from the LD device 58-2 are coaxially multiplexed by the dichroic mirror 71 and are incident on the optical fiber 72. Light incident on the optical fiber 72 is transmitted through the optical fiber 72 and is incident on the first phosphor layer 61-1 of the wavelength conversion member 61. Green light in the incident light excites the red phosphor in the first phosphor layer 61-1, and the first phosphor layer 61-1 emits red light. Light passing through the first phosphor layer 61-1 without absorption and red light emitted from the first phosphor layer 61-1 are incident on the second phosphor layer 61-2. Blue light in the incident light excites the yellow-green phosphor in the second phosphor layer 61-2, and the second phosphor layer 61-2 emits yellow-green light. Red light emitted from the first phosphor layer 61-1, yellow-green light emitted from the second phosphor layer 61-2, and blue light and green light not absorbed by the first phosphor layer 61-1 and the second phosphor layer 61-2 are emitted outward. These light beams emitted outward can be mixed to produce white light. The white light emitted from the wavelength conversion member 61 is applied to an object through the objective lens 73. Because the white light is composed of blue light, green light, yellow-green light, and red light, the fiber lighting apparatus 70 of the present embodiment can control each color light to adjust the color of the white light. Thus, the fiber lighting apparatus 70 of the present embodiment has high color controllability of white light to be emitted.

The fiber lighting apparatus 70 of the present embodiment can include a LD device as a solid-state light source. In the fiber lighting apparatus 70 of the present embodiment, the red phosphor in the wavelength conversion member 61 is a phosphor including Ce as a luminescent center and is less likely to reach luminance saturation even when excited by strong excitation light. Unlike known red phosphors including Eu as a luminescent center, therefore, the red phosphor in the present embodiment can be excited by a laser beam with a high energy density. Thus, the fiber lighting apparatus 70 of the present embodiment can include as a solid-state light source a LD device that emits light with a higher light power density than LEDs. Consequently, the fiber lighting apparatus 70 of the present embodiment can be compact and produce high power.

Although not shown in FIG. 25, a condenser lens may be disposed on the optical path between a light output end of the optical fiber 72 and the wavelength conversion member 61.

Although the wavelength conversion member 61 is disposed on the light output side of the optical fiber 72 in the present embodiment, the present disclosure is not limited to this structure. The wavelength conversion member 61 may be disposed on the light incident side of the optical fiber 72.

In this case, white light emitted from the wavelength conversion member 61 is incident on the optical fiber 72 and is transmitted to a target position through the optical fiber 72. Transmitted white light is emitted outward from the light output end of the optical fiber 72.

The fiber lighting apparatus of the present embodiment is also suitable for illumination in high places. Examples of lighting apparatuses installed in high places include lighting apparatuses for stadiums, expressways, tunnels, and bridges.

Figure 26:
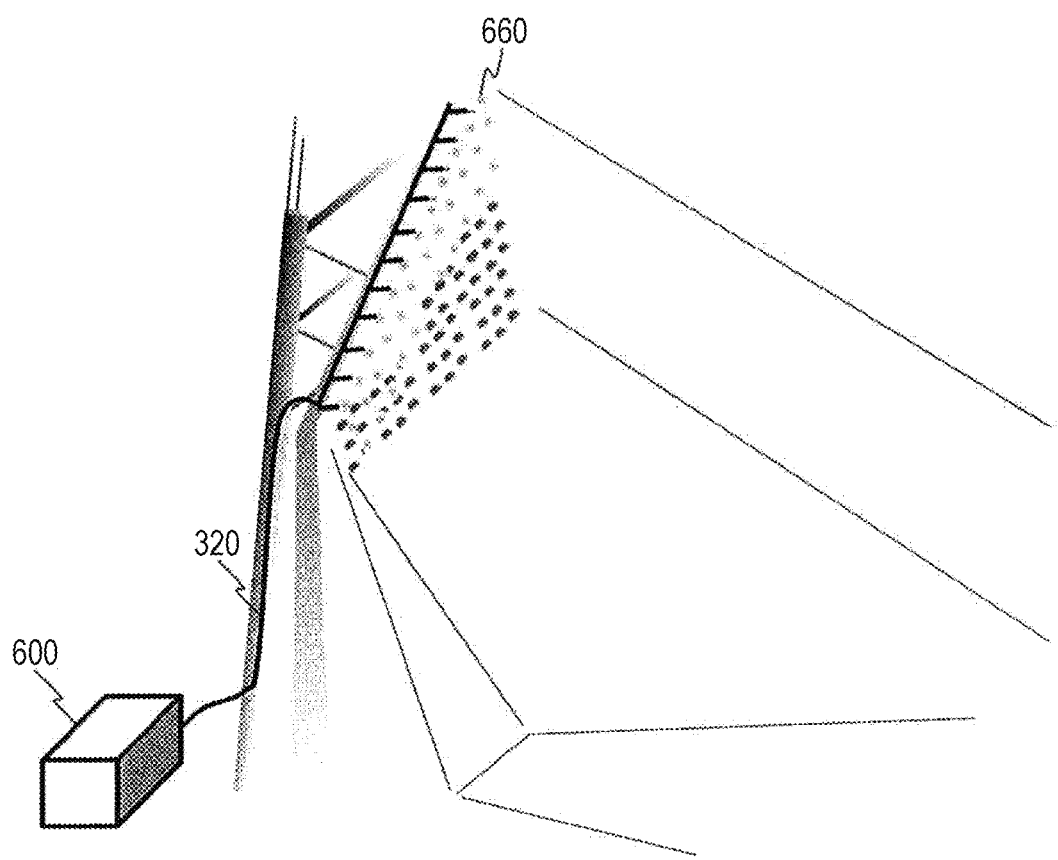
FIG. 26 is a schematic view of an example of a fiber lighting apparatus for high-place illumination according to the second embodiment.

FIG. 26 illustrates a fiber lighting apparatus for use in stadiums as an example of fiber lighting apparatuses for high-place illumination. This lighting apparatus includes a light source apparatus 600, an optical fiber 320, and illumination units 660. The light source apparatus 600 includes the LD device 58-1 and the LD device 58-2 as solid-state light sources and the dichroic mirror 71 illustrated in FIG. 25 and is installed on the ground (in a low place). The optical fiber 320 is divided into a plurality of optical fibers and couples the light source apparatus 600 to the illumination units 660. Each of the illumination units 660 is disposed near an end of the optical fiber 320 and is installed in a high place. The illumination units 660 include the wavelength conversion member 61 and the objective lens 73 illustrated in FIG. 25, for example. Light transmitted through the optical fiber 320 is emitted outward from the illumination units 660. The operation of the fiber lighting apparatus for high-place illumination is the same as the operation of the fiber lighting apparatus 70. Thus, the fiber lighting apparatus for high-place illumination can also emit high-power white light outward from the illumination units 660.

Such a structure can provide a compact and efficient stadium lighting apparatus with high maintainability. In known stadium illumination, many lamp light sources are installed in high places, which makes maintenance (such as lamp replacement) difficult. Furthermore, large-scale housings that can withstand high wind pressure in high places are required. In the present application example, the optical fiber can transmit light from the light source apparatus 600 disposed on the ground to the illumination units 660 disposed in a high place. Thus, a compact lighting apparatus with high maintainability can be provided.

Figure 27:
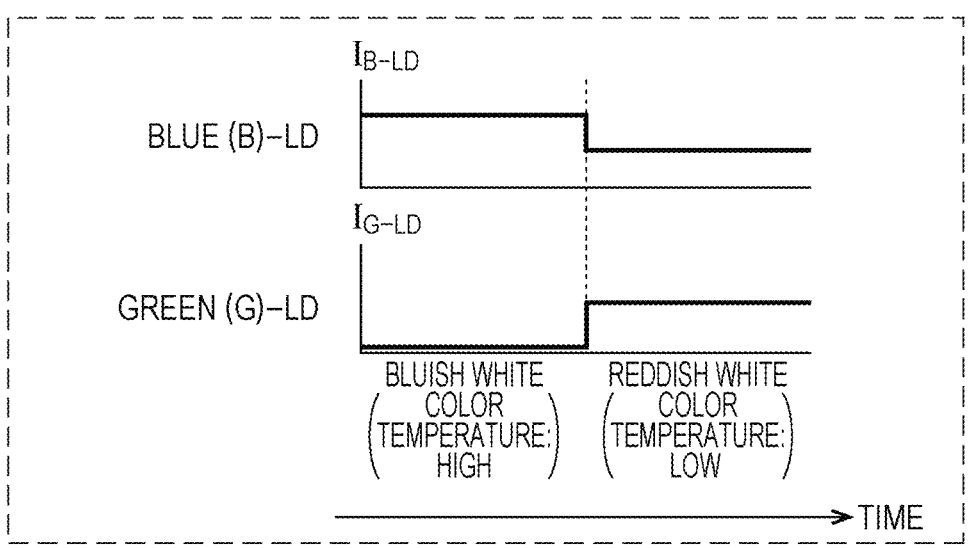
FIG. 27 is a current timing chart for illustrating an example of a method for driving the fiber lighting apparatus according to the second embodiment (current control)
Figure 28A:
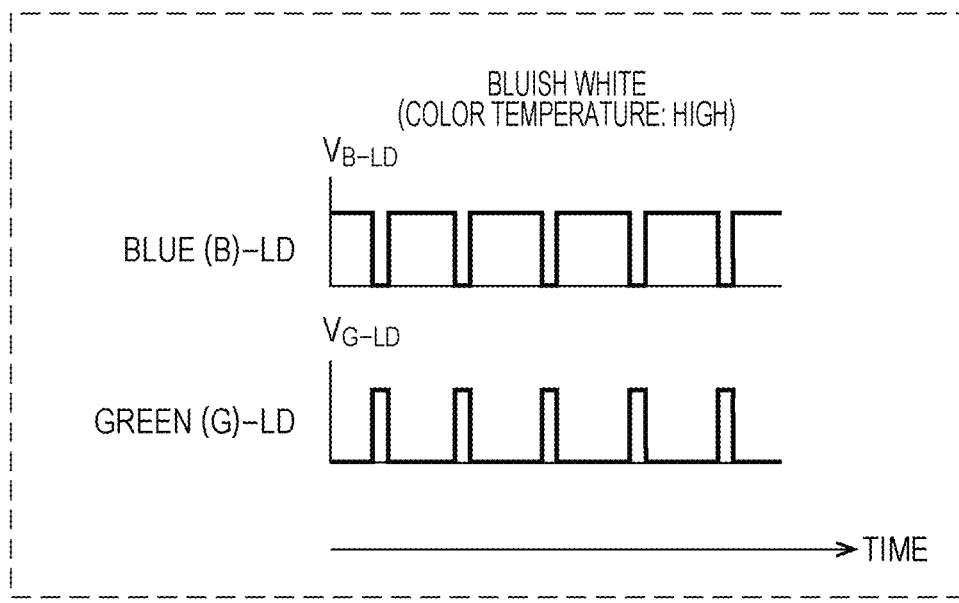
FIG. 28A is a voltage timing chart for illustrating an example of a method for driving the fiber lighting apparatus according to the second embodiment (PWM control)
Figure 28B:
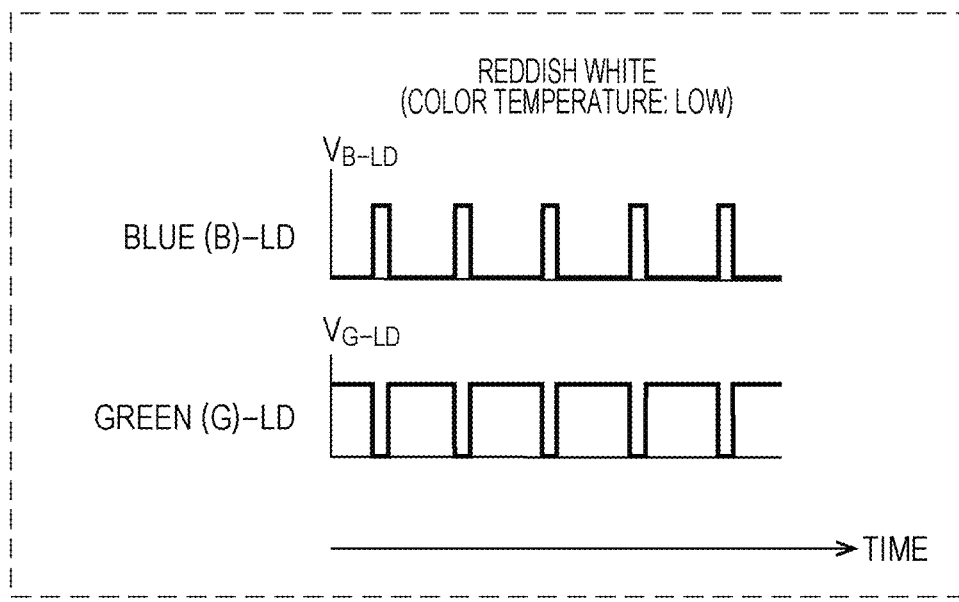
FIG. 28B is a voltage timing chart for illustrating another example of a method for driving the fiber lighting apparatus according to the second embodiment (PWM control)

FIG. 27 illustrates a control method for controlling the color tone of output light of the fiber lighting apparatus of the present embodiment. FIGS. 28A and 28B illustrate another control method for controlling the color tone of output light of the fiber lighting apparatus of the present embodiment. As described in the first embodiment, the red phosphor used in the fiber lighting apparatus of the present embodiment has low excitation efficiency and weak light emission for blue light. Thus, the main use of blue light as excitation light mainly induces the light emission of the yellow-green phosphor. Thus, the output white light is of white mainly including a mixture of blue and yellow-green and is bluish white light with high color temperature. In contrast, the use of blue and green in excitation light induces the light emission of the red phosphor. Thus, the output white light is of white including a mixture of green, blue, yellow-green, and red and is reddish white light with low color temperature. In this case, as illustrated in FIG. 27, the drive current of a blue (B)-LD, which emits blue excitation light, and the drive current of a green (G)-LD, which emits green excitation light, can be controlled to alter the color tone of output white light. More specifically, the drive current of the blue (B)-LD can be increased and the drive current of the green (G)-LD can be decreased to output bluish white light with high color temperature. The drive current of the blue (B)-LD can be decreased and the drive current of the green (G)-LD can be increased to output reddish white light with low color temperature. In another control method, as illustrated in FIGS. 28A and 28B, the drive voltage of the blue (B)-LD, which emits blue excitation light, and the drive voltage of the green (G)-LD, which emits green excitation light, are pulse-driven, and the color tone of output white light can be altered by pulse width modulation drive (PWM drive), in which the pulse width of each of the drive voltages is changed. More specifically, as illustrated in FIG. 28A, the pulse width of the drive voltage of the blue (B)-LD can be increased, and the pulse width of the green (G)-LD can be decreased to output bluish white light with high color temperature. Alternatively, as illustrated in FIG. 28B, the drive voltage pulse width of the blue (B)-LD can be decreased, and the pulse width of the green (G)-LD can be increased to output reddish white light with low color temperature.

Such a structure can provide a more compact lighting apparatus with higher maintainability than known stadium lighting apparatuses that include many lamps in high places. The lighting apparatus can adjust the color tone to each application.

Such a structure can also be applied to illumination for expressways and bridges as well as stadium illumination. Bridges are located above rivers, above the ocean, and in the mountains. Illuminators for bridges are disposed in high places and in strong winds. Thus, installation and maintenance of illuminators involve considerable danger, and therefore a fiber lighting apparatus according to the present application example is particularly desired. Such a structure can provide a more compact tunnel lighting apparatus with higher maintainability than known tunnel lighting apparatuses that include many lamps in high places over a long distance.

Third Embodiment

A third embodiment describes as an example of a fiber light source of the present disclosure an endoscopic fiber lighting apparatus that includes a LD that emits blue light and a LD that emits green light as solid-state light sources.

Figure 29:
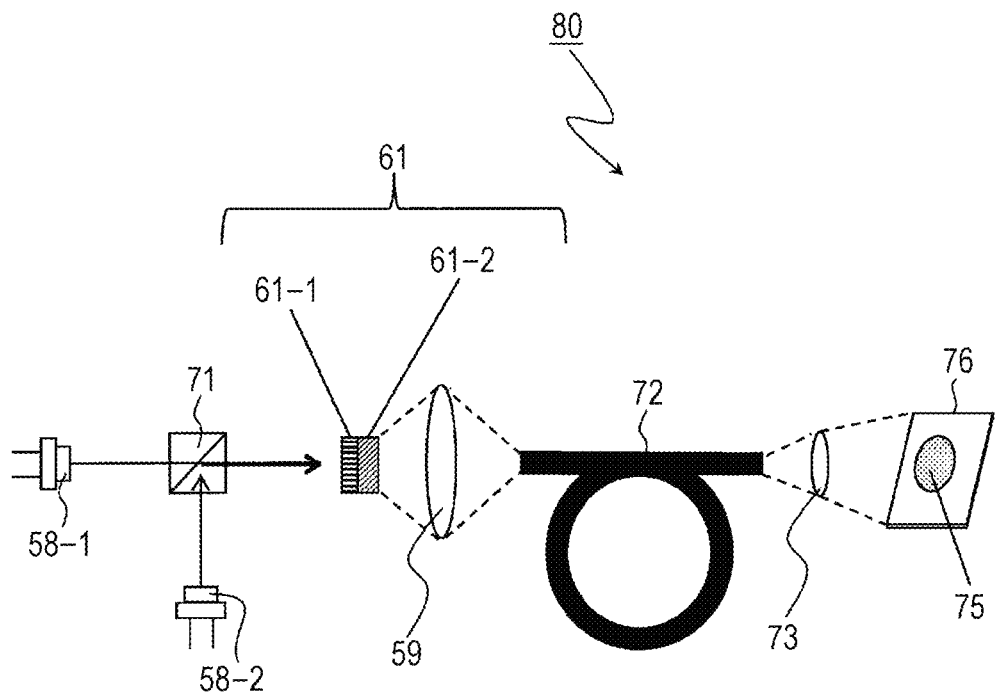
FIG. 29 is a schematic view of an endoscopic fiber lighting apparatus according to a third embodiment.

FIG. 29 is a schematic view of an endoscopic fiber lighting apparatus 80 according to the third embodiment.

The endoscopic fiber lighting apparatus 80 includes the LD device 58-1 and the LD device 58-2 as solid-state light sources, the dichroic mirror 71, the wavelength conversion member 61 as a wavelength convertor, a coupler lens 59, the optical fiber 72, and the objective lens 73.

The LD device 58-1 is a LD that emits blue light. The LD device 58-2 is a LD that emits green light The LD device 58-1 emits light in a blue region and has an emission spectrum peak in the wavelength range of 430 to 470 nm. More specifically, the LD device 58-1 is a LD device that emits blue light. The LD device 58-1 may be a GaN semiconductor laser, that is, a GaN LD. The LD device 58-2 emits light in a green region and has an emission spectrum peak in the wavelength range of 480 to 550 nm, desirably 510 to 540 nm. More specifically, the LD device 58-2 is a LD device that emits green light. The LD device 58-2 may be a GaN semiconductor laser, that is, a GaN LD. The LD device 58-2 may also be a YAG:Nd solid-state laser with a second harmonic generator.

Blue light emitted from the LD device 58-1 and green light emitted from the LD device 58-2 are coaxially multiplexed by the dichroic mirror 71 and are incident on the wavelength conversion member 61. Thus, the dichroic mirror 71 is disposed on the optical path between the LD devices 58-1 and 58-2 and the wavelength conversion member 61. The optical path is a common optical path of blue light and green light.

The wavelength conversion member 61 has a layered structure composed of a first phosphor layer 61-1 containing a red phosphor including Ce as a luminescent center and a second phosphor layer 61-2 containing a yellow-green phosphor. In the wavelength conversion member 61 in the present embodiment, the first phosphor layer 61-1 is disposed on the light incident side. The red phosphor including the Ce luminescent center is described in the first embodiment and is not described in detail here. For example, the yellow-green phosphor is a phosphor including Ce as a luminescent center, such as YAG:Ce. The red phosphor in the first phosphor layer 61-1 is excited by green light and emits red light. The yellow-green phosphor in the second phosphor layer 61-2 is excited by blue light and emits yellow-green light. Thus, these phosphors convert output light emitted from the LD device 58-1 and the LD device 58-2 to light with a longer wavelength. In the present embodiment, light emitted from the wavelength conversion member 61 is incident on the optical fiber 72 through the coupler lens 59.

The optical fiber 72 transmits incident light to a target position. In the endoscopic fiber lighting apparatus 80 of the present embodiment, the optical fiber 72 transmits light to the position of a lesion 75 in the body tissue 76. The objective lens 73 is disposed on the light output side of the optical fiber 72.

The operation of the endoscopic fiber lighting apparatus 80 of the present embodiment will be described below. Blue light emitted from the LD device 58-1 and green light emitted from the LD device 58-2 are coaxially multiplexed by the dichroic mirror 71 and are incident on the first phosphor layer 61-1 of the wavelength conversion member 61. Green light in the incident light excites the red phosphor in the first phosphor layer 61-1, and the first phosphor layer 61-1 emits red light. Light passing through the first phosphor layer 61-1 without absorption and red light emitted from the first phosphor layer 61-1 are incident on the second phosphor layer 61-2. Blue light in the incident light excites the yellow-green phosphor in the second phosphor layer 61-2, and the second phosphor layer 61-2 emits yellow-green light. Red light emitted from the first phosphor layer 61-1, yellow-green light emitted from the second phosphor layer 61-2, and blue light and green light not absorbed by the first phosphor layer 61-1 and the second phosphor layer 61-2 are emitted outward. These light beams emitted outward can be mixed to produce white light. White light emitted from the wavelength conversion member 61 is incident on the optical fiber 72 through the coupler lens 59. The white light incident on the optical fiber 72 is transmitted through and emitted from the optical fiber 72, and is incident on an object of the lesion 75 in the body tissue 76 through the objective lens 73. Because the white light is composed of blue light, green light, yellow-green light, and red light, the endoscopic fiber lighting apparatus 80 of the present embodiment can control each color light to adjust the color of the white light. Thus, the endoscopic fiber lighting apparatus 80 of the present embodiment has high color controllability of white light to be emitted.

The endoscopic fiber lighting apparatus 80 of the present embodiment can include a LD device as a solid-state light source. In the endoscopic fiber lighting apparatus 80 of the present embodiment, the red phosphor in the wavelength conversion member 61 is a phosphor including Ce as a luminescent center and is less likely to reach luminance saturation even when excited with strong excitation light. Unlike known red phosphors including Eu as a luminescent center, therefore, the red phosphor in the present embodiment can be excited by a laser beam with a high energy density. Thus, the endoscopic fiber lighting apparatus 80 of the present embodiment can include as a solid-state light source a LD device that emits light with a higher light power density than LEDs. Consequently, the endoscopic fiber lighting apparatus 80 of the present embodiment can be compact and produce high power.

Figure 30:
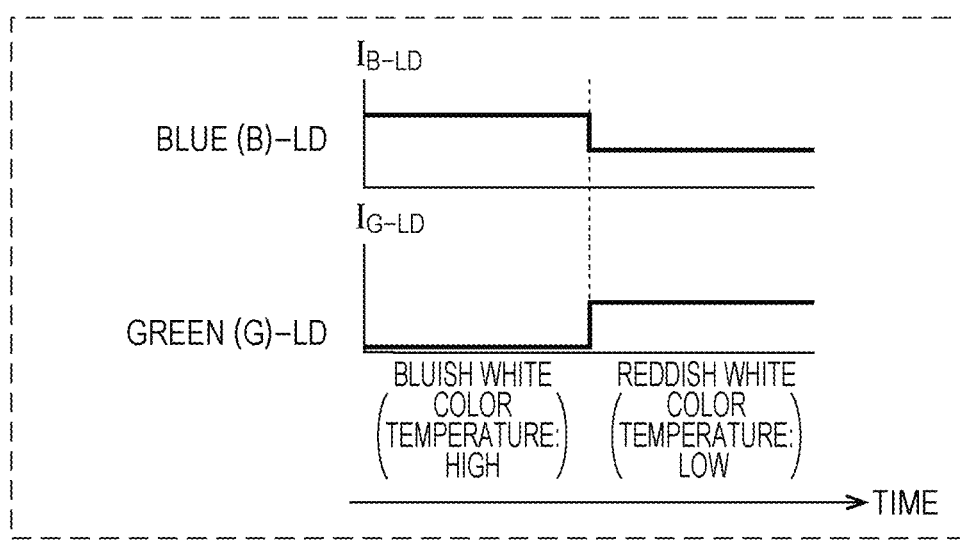
FIG. 30 is a current timing chart for illustrating an example of a method for driving the endoscopic fiber lighting apparatus according to the third embodiment (current control)
Figure 31A:
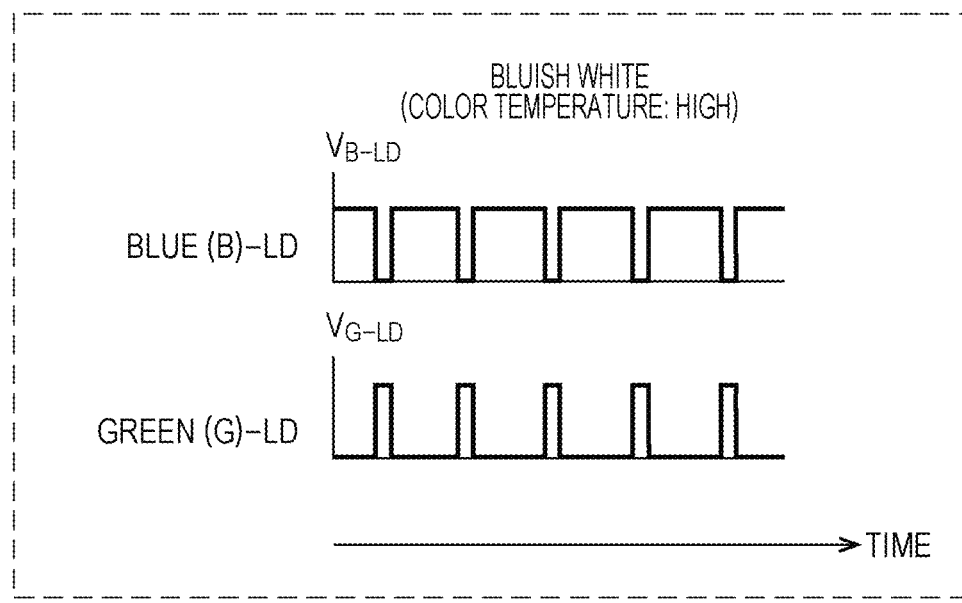
FIG. 31A is a voltage timing chart for illustrating an example of a method for driving the endoscopic fiber lighting apparatus according to the third embodiment (PWM control)
Figure 31B:
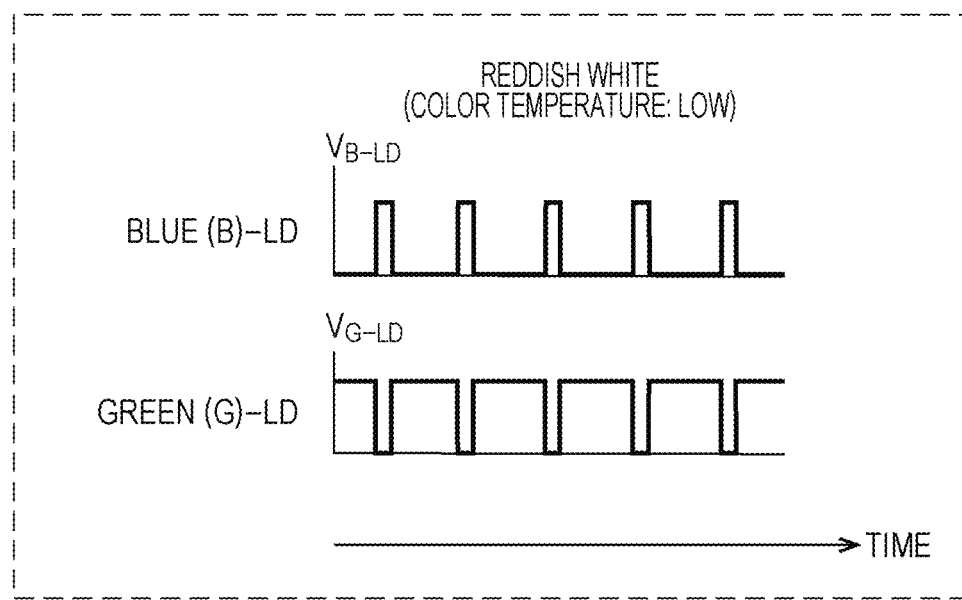
FIG. 31B is a voltage timing chart for illustrating another example of a method for driving the endoscopic fiber lighting apparatus according to the third embodiment (PWM control)

FIG. 30 illustrates a control method for controlling the color tone of output light of an endoscopic fiber lighting apparatus. FIGS. 31A and 31B illustrate another control method for controlling the color tone of output light of an endoscopic fiber lighting apparatus. As described in the first embodiment, the red phosphor used in the endoscopic fiber lighting apparatus of the present embodiment has low excitation efficiency and weak light emission for blue light. Thus, the main use of blue light as excitation light mainly induces the light emission of the yellow-green phosphor. Thus, the output white light is of white mainly including a mixture of blue and yellow-green and is bluish white light with high color temperature. In contrast, the use of blue and green in excitation light induces the light emission of the red phosphor. Thus, the output white light is of white including a mixture of green, blue, yellow-green, and red and is reddish white light with low color temperature. In this case, as illustrated in FIG. 30, the drive current of a blue (B)-LD, which emits blue excitation light, and the drive current of a green (G)-LD, which emits green excitation light, can be controlled to alter the color tone of output white light. More specifically, the drive current of the blue (B)-LD can be increased and the drive current of the green (G)-LD can be decreased to output bluish white light with high color temperature. The drive current of the blue (B)-LD can be decreased and the drive current of the green (G)-LD can be increased to output reddish white light with low color temperature. In another control method, as illustrated in FIGS. 31A and 31B, the drive voltage of the blue (B)-LD, which emits blue excitation light, and the drive voltage of the green (G)-LD, which emits green excitation light, are pulse-driven, and the color tone of output white light can be altered by pulse width modulation drive (PWM drive), in which the pulse width of each of the drive voltages is changed. More specifically, as illustrated in FIG. 31A, the pulse width of the drive voltage of the blue (B)-LD can be increased, and the pulse width of the green (G)-LD can be decreased to output bluish white light with high color temperature. Alternatively, as illustrated in FIG. 31B, the pulse width of the drive voltage of the blue (B)-LD can be decreased, and the pulse width of the green (G)-LD can be increased to output reddish white light with low color temperature.

With such a structure, light with absorption and reflection wavelengths characteristic of the lesion 75 in the body tissue 76 can be applied to an observation region to obtain a high-contrast diagnostic image.

The endoscopic fiber lighting apparatus of the present embodiment can be utilized in endoscopes.

Figure 32:
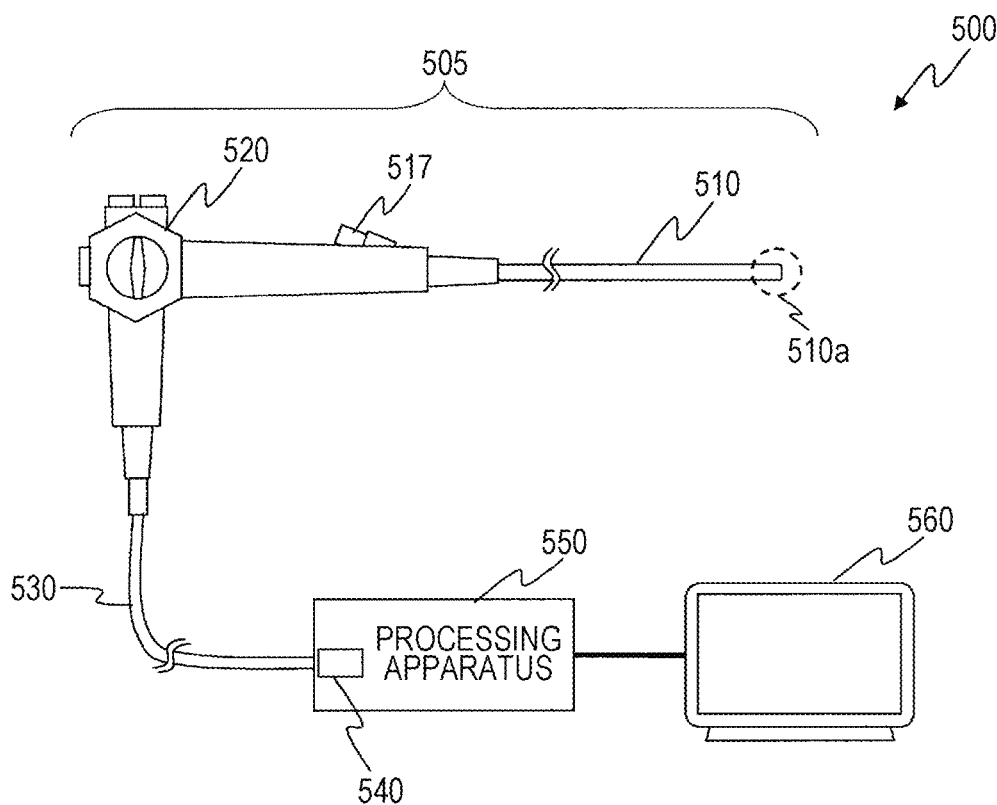
FIG. 32 is a schematic view of an endoscope according to the third embodiment.

FIG. 32 is a schematic view of an example of an endoscope system 500 that includes the endoscopic fiber lighting apparatus of the present embodiment. The endoscope system 500 includes an endoscope 505, a processing apparatus 550 coupled to the endoscope 505, and a display unit 560 coupled to the processing apparatus 550. The term "couple", as used herein, refers to electrical connection that allows electric signals to be sent and received.

The endoscope 505 includes an insert 510 to be inserted into the body cavity, a forceps insertion opening 517, a manipulating portion 520, and a cable 530 to be coupled to the processing apparatus 550. The insert 510 is an enlongated (or tubular) member made of a flexible material. The tip (end portion 510a) of the insert 510 may be configured to be bent by the operator.

The end portion 510a includes a light-emitting device, an image sensor, and an optical system. Thus, a light output portion of the endoscopic fiber lighting apparatus of the present embodiment corresponds to a light-emitting device. More specifically, for example, the end portion 510a includes as a light-emitting device the light output end of the optical fiber 72 of the endoscopic fiber lighting apparatus 80 illustrated in FIG. 29 and includes the objective lens 73 as an optical system. The light-emitting device irradiates an object with light. Reflected light is converged by the optical system and is incident on an imaging plane of the image sensor. In response to this, the image sensor outputs an electric signal depending on the amount of light received per pixel.

The manipulating portion 520 includes various switches and buttons for manipulating the endoscope 505. For example, the manipulating portion 520 may include a power switch, an on/off switch for illumination, an angle knob for changing the direction of the end portion 510a, a button for injecting air or water through the end portion 510a, and a release button for instructing the start and stop of imaging.

The cable 530 includes a light guide (that is, an optical fiber) that can absorb excitation light from the excitation light source 540 at one end thereof and emit the excitation light from the other end thereof and a signal line for transmitting electric signals from the image sensor to the processing apparatus 550. In addition to these, the cable 530 may include a water and air supply pipe. The excitation light source 540 corresponds to a solid-state light source of the endoscopic fiber lighting apparatus of the present embodiment. More specifically, the excitation light source 540 includes the LD device 58-1 and the LD device 58-2 of the endoscopic fiber lighting apparatus 80 illustrated in FIG. 29.

The processing apparatus 550 includes the excitation light source 540, a processor, such as a CPU, an image-processing circuit, a memory, and an input/output interface. Excitation light emitted from the excitation light source 540 is transmitted through the light guide in the cable 530 and is incident on the light-emitting device in the end portion 510a. In response to this, the light-emitting device emits light. The processing apparatus 550 processes electric signals sent from the image sensor and produces and outputs image signals. The image signals are transmitted to the display unit 560.

Figure 33:
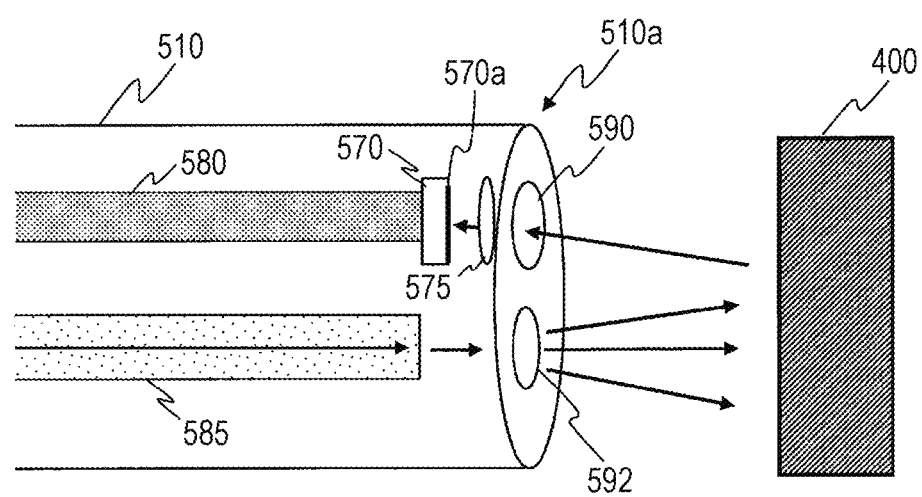
FIG. 33 is a schematic view of the inner structure of an end portion of the endoscope according to the third embodiment.

FIG. 33 is a simplified view of the inner structure of the end portion 510a of the insert 510. The endoscope 505 includes a tip (the light output end of the optical fiber) of a light guide 585 as a light-emitting device, an image sensor 570, and an optical system 575 in the end portion 510a. The optical system 575 faces an imaging place 570a of the image sensor 570.

Light emitted from a tip of the light guide 585 is emitted outward through an opening for illumination 592. Light emitted from the tip of the light guide 585 is described above in detail as light emitted from the optical fiber 72 of the endoscopic fiber lighting apparatus 80 and is not described in detail here. An optical system for diffusing or converging light (for example, the objective lens 73 in the endoscopic fiber lighting apparatus 80) may be disposed near the opening for illumination 592.

The image sensor 570 is coupled to a signal line 580. The signal line 580 transmits electric signals emitted from the image sensor 570 to the processing apparatus 550. For example, the image sensor 570 is an image sensor, such as a charge coupled device (CCD) or a complementary metal oxide semiconductor (CMOS) sensor. Photodetector cells (for example, photodiodes) are arranged on the imaging place 570a of the image sensor 570. The photodetector cells output by photoelectric conversion an electric signal depending on the intensity of light received (also referred to as the amount of light received). The photodetector cells may face color filters. The color filters are arranged in two dimension (typically in a square grid). For example, the color filters may have a typical Bayer pattern, in which a unit of four color filters, that is, a red filter, two green filters, and a blue filter is repeatedly arranged. Each photodetector cell and a color filter facing the photodetector cell constitute one pixel. The color filters may be omitted.

Light emitted from the light guide 585 is directed to an object 400 (for example, a lesion in the body tissue) through the opening for illumination 592. Part of the light is reflected by the object 400 and passes through an observation opening 590. Light passing through the observation opening 590 is converged onto the imaging place 570a of the image sensor 570 via the optical system 575 including an objective lens. Consequently, an image of the object 400 is formed on the imaging place 570a. The photodetector cells output an electric signal corresponding to the image. The signal line 580 transmits the electric signal to the processing apparatus 550.

The processing apparatus 550 produces an image signal based on the transmitted electric signal. For example, the processing apparatus 550 produces an image signal based on the transmitted electric signal by performing image processing, such as color interpolation, white balance adjustment, gamma correction, noise reduction, and/or color conversion. The image processing is performed by an image-processing circuit, such as a digital signal processor (DSP), in the processing apparatus 550. The image signal thus produced is transmitted from the processing apparatus 550 to the display unit 560. The display unit 560 displays an image based on the image signal. Thus, the operator can observe a picture of the object 400.

FIG. 33 illustrates a simplified inner structure of the end portion 510a. Typically, the end portion 510a may further include other components not illustrated in the figure, such as an opening for forceps and a water and air supply nozzle. These will be briefly described below.

Figure 34:
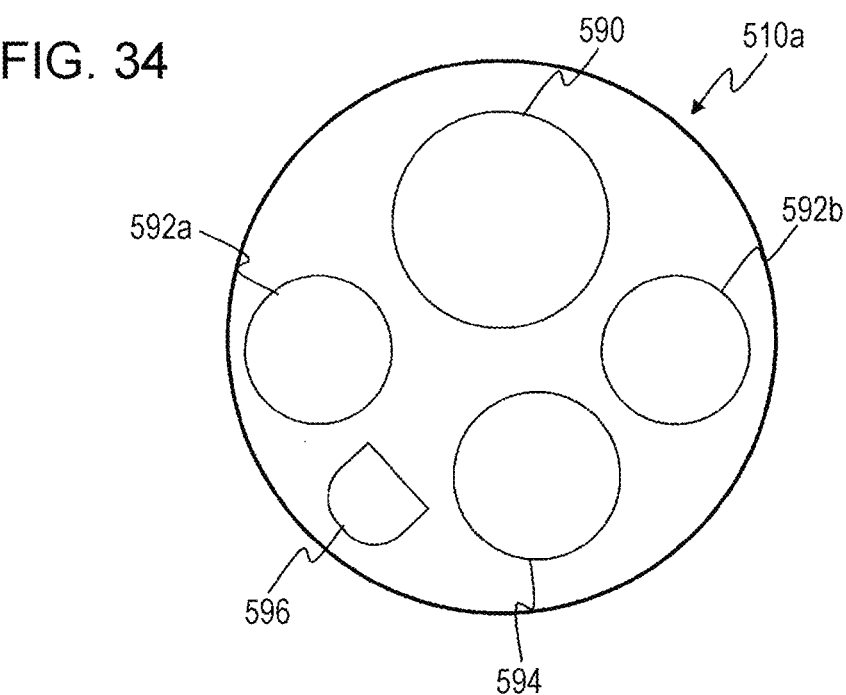
FIG. 34 is a schematic view of an end of the end portion of the endoscope according to the third embodiment.

FIG. 34 is a schematic view of the end portion 510a viewed from the object 400 in one structure example. The end portion 510a includes two openings for illumination 592a and 592b, an opening for forceps 594, and a water and air supply nozzle 596. The optical fiber 72 and the objective lens 73 in the endoscopic fiber lighting apparatus 80 of the present embodiment are disposed behind each of the openings for illumination 592a and 592b. Forceps inserted through the forceps insertion opening 517 pass through the opening for forceps 594. The water and air supply nozzle 596 injects water or air to wash away blood or mucus adhering to the end portion 510a. The openings for illumination 592a and 592b are symmetrically disposed about the central axis. This can prevent a shadow from being formed during the imaging process.

Advantageously, the endoscope of the present embodiment includes the endoscopic fiber lighting apparatus 80 of the present embodiment and can easily identify a very small lesion site, such as cancer. Light emitted from the endoscopic fiber lighting apparatus 80 of the present embodiment contains blue light. Hemoglobin in blood absorbs blue light. Thus, blue light irradiation allows capillary vessels on the surface to be emerged. However, the use of blue light alone is insufficient in the amount of light. Light emitted from the endoscopic fiber lighting apparatus 80 of the present embodiment is white light including green light and red light in addition to blue light. This can produce generally clear images. As described above, the endoscopic fiber lighting apparatus 80 of the present embodiment can modulate the color tone of output white light to bluish white light and reddish white light, for example. Thus, light with absorption and reflection wavelengths characteristic of a lesion can be chosen and applied to an observation region to obtain a high-contrast diagnostic image.

Furthermore, the endoscopic fiber lighting apparatus 80 of the present embodiment can advantageously omit a color filter, which is required in known endoscopes.

Figure 35:
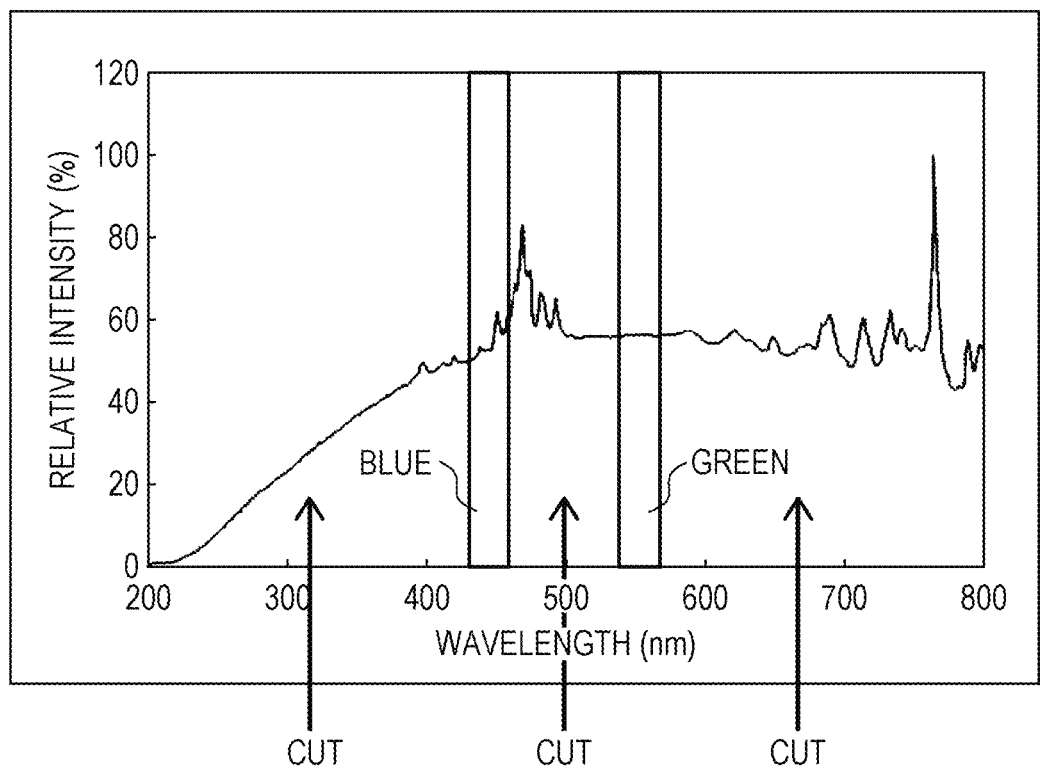
FIG. 35 is an emission spectrum of a known xenon lamp.

FIG. 35 is an emission spectrum of a known xenon lamp. The emission spectrum has a broad intensity distribution throughout the entire wavelength band of visible light. Thus, the use of light in a blue wavelength band and light in a green wavelength band requires color filters for removing light in the other wavelength bands. Such color filters increase optical loss and decrease efficiency. Diagnostic imaging of the difference in state between a surface layer portion and a deep layer portion of a tissue utilizing the difference in contrast from an image produced by using ordinary white light requires a mechanism for switching these color filters or a fiber for introducing another white light.

In contrast, the endoscopic fiber lighting apparatus 80 of the present embodiment can change the drive current or drive pulse width of the solid-state light sources, that is, the LD device 58-1, which emits blue light, and the LD device 58-2, which emits green light, to continuously produce white light with a strong blue light component to white light with a strong red component. Thus, observation light with optimum contrast and brightness for diagnosis can be emitted. Furthermore, an endoscope system for finer diagnostic imaging can be provided by displaying the difference in chromaticness and chromaticity of images taken with observation light beams with different color tones by image processing.

Fourth Embodiment

Figure 36:
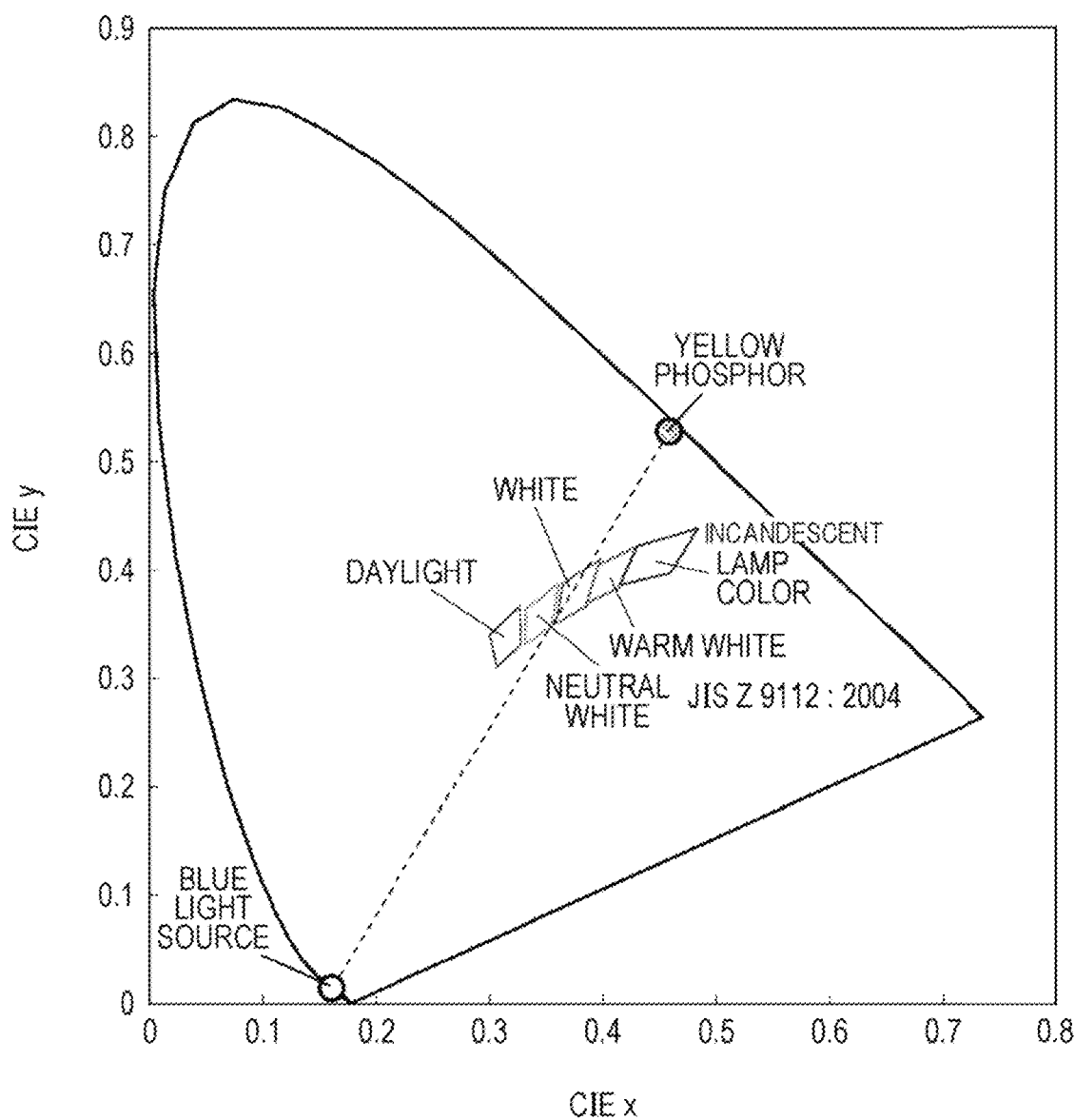
FIG. 36 is a graph of CIE chromaticity coordinates.
Figure 37:
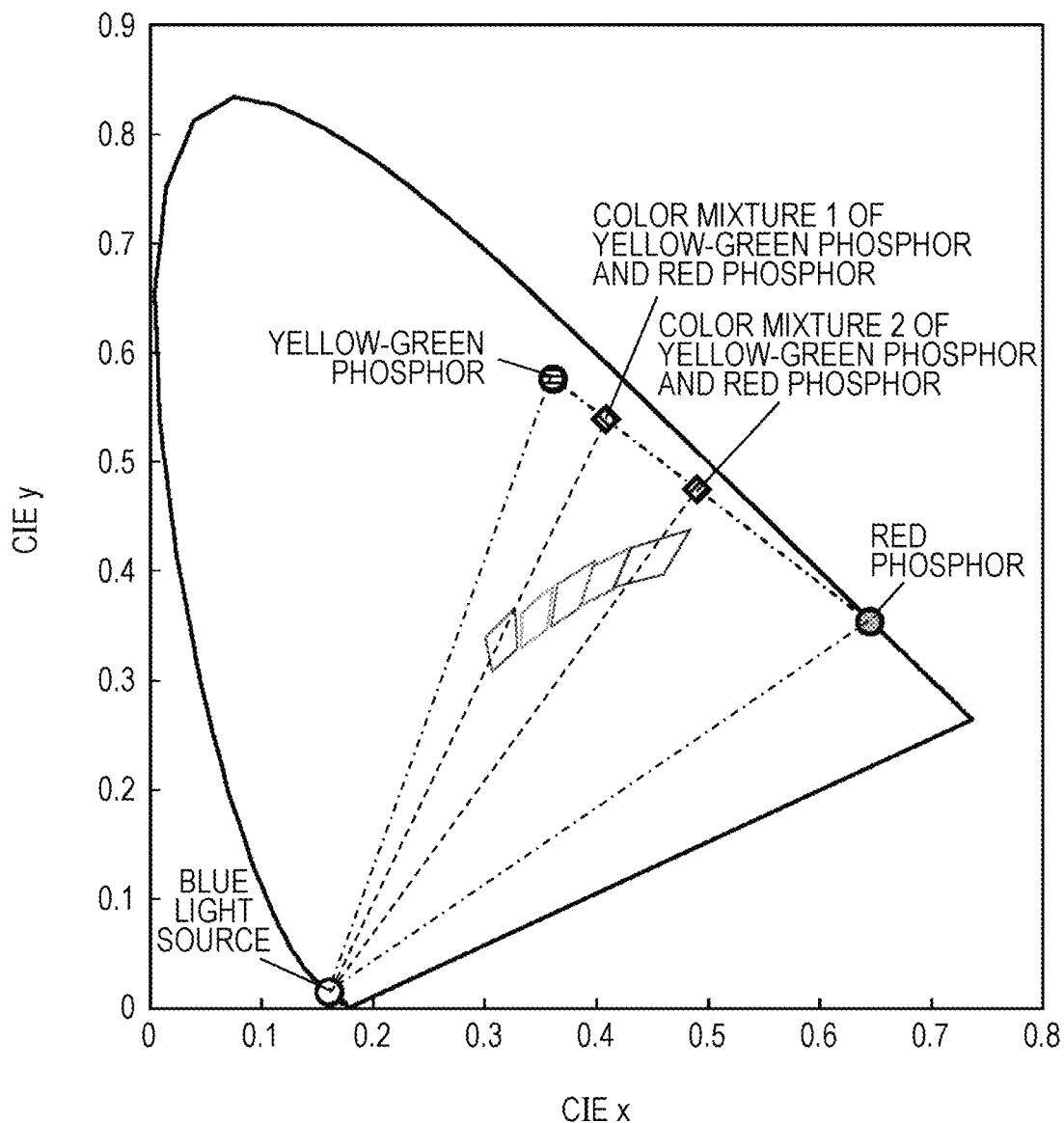
FIG. 37 is a graph of CIE chromaticity coordinates.
Figure 38:
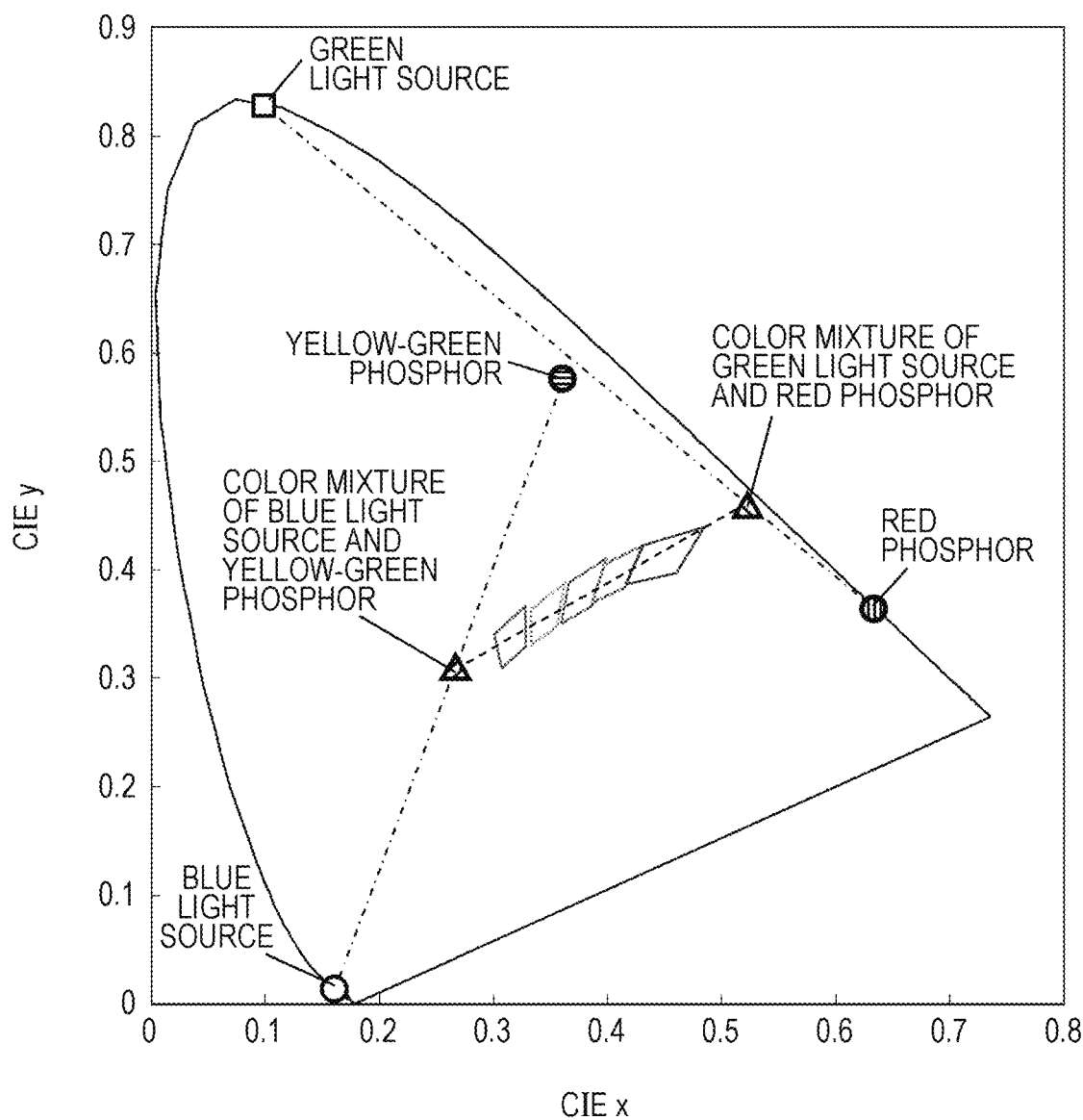
FIG. 38 is a graph of CIE chromaticity coordinates.

FIGS. 36 to 38 illustrate CIE chromaticity coordinates. White colors include incandescent lamp color, warm white, white, neutral white, and daylight. JIS Z 9112:2004 defines the chromaticity coordinates of these white colors listed in Table 19.

point of the yellow phosphor and the chromaticity point of the blue light source. Thus, for example, an artificial white light source including a combination of a yellow phosphor (CIEx=0.458, CIEy=0.528) and a blue light source (CIEx=0.161, CIEy=0.014) illustrated in FIG. 36 can produce only white.

By contrast, an RGB white light source including a combination of a yellow-green phosphor, a red phosphor, and a blue light source can reproduce colors in the triangular area formed by the straight lines between the chromaticity point of the yellow-green phosphor, the chromaticity point of the red phosphor, and the chromaticity point of the blue light source. Thus, the mixing ratio of the yellow-green phosphor to the red phosphor can be changed to produce all white lights of incandescent lamp color, warm white, white, neutral white, and daylight. For example, at the chromaticity point of a color mixture 1 of the yellow-green phosphor (CIEx=0.361, CIEy=0.576) and the red phosphor (CIEx=0.645, CIEy=0.353) illustrated in FIG. 37, the yellow-green phosphor and the red phosphor can be mixed to produce daylight. At the chromaticity point of a color mixture 2 of the yellow-green phosphor and the red phosphor in the figure, the yellow-green phosphor and the red phosphor can be mixed to produce the incandescent lamp color.

However, the RGB white light source system cannot alter the hue of white light unless the blend ratio of phosphors is changed. More specifically, a white light source configured to produce daylight cannot produce the incandescent lamp color. Thus, in order to produce a light-emitting device that can alter the hue, for example, a light source device that produces daylight and a light source device that produces the incandescent lamp color are combined, and the brightness of each of the light source devices is changed to alter the hue. Thus, light source devices that can alter the hue are larger than light source devices that produce a single hue.

A white light source system of the present embodiment can freely alter the hue of the white light source. A fiber light source of a white light source of the present embodiment includes the red phosphor, the yellow-green phosphor, the blue light source, and the green light source described in any of the embodiments, modified examples, and examples, for example. The white light source includes a wavelength convertor containing the red phosphor and other phosphor(s) (for example, the yellow-green phosphor), a blue light source that emits blue light, and a green light source that emits green light. The red phosphor is excited by at least part of the green light to emit second light. The second light has a spectrum with a peak wavelength in the range of 600 to 700 nm. Another phosphor is excited by at least part of the blue light to emit third light. The third light has a spectrum

TABLE 19

| Daylight D | | Neutral white N | | White W | | Warm white WW | | Incandescent lamp color L | |
|---|---|---|---|---|---|---|---|---|---|
| CIE x | CIE y | CIE x | CIE y | CIE x | CIE y | CIE x | CIE y | CIE x | CIE y |
| 0.2998 | 0.3396 | 0.3616 | 0.3875 | 0.3985 | 0.4102 | 0.4305 | 0.4218 | 0.4834 | 0.4382 |
| 0.3064 | 0.3091 | 0.3552 | 0.3476 | 0.3849 | 0.3668 | 0.4141 | 0.3834 | 0.4594 | 0.3971 |
| 0.3282 | 0.3297 | 0.3324 | 0.3296 | 0.3584 | 0.3499 | 0.3856 | 0.3693 | 0.4153 | 0.3862 |
| 0.3274 | 0.3673 | 0.3326 | 0.3635 | 0.3652 | 0.388 | 0.3966 | 0.4044 | 0.4305 | 0.4218 |

An artificial white light source including a combination of a yellow phosphor and a blue light source can reproduce only colors on the straight line between the chromaticity with a peak wavelength in the range of 500 to 600 nm. Synthesized light of green light passing through the wavelength convertor and the second light emitted from the wavelength convertor has a chromaticity point satisfying 0.48<CIEx<0.60 and 0.40<CIEy<0.49. Synthesized light of blue light passing through the wavelength convertor and the third light emitted from the wavelength convertor has a chromaticity point satisfying 0.15<CIEx<0.30 and 0.20<CIEy<0.36.

For example, in a white light source system of the present embodiment, for example, as illustrated in FIG. 38, a blue light source (CIEx=0.161, CIEy=0.014) can be used to induce the light emission of a yellow-green phosphor (CIEx=0.361, CIEy=0.576), thereby reproducing the chromaticity point of a color mixture of the blue light source and the yellow-green phosphor. Alternatively, a green light source (CIEx=0.098, CIEy=0.828) can be used to induce the light emission of a red phosphor (CIEx=0.634, CIEy=0.364), thereby reproducing the chromaticity point of a color mixture of the green light source and the red phosphor. Because colors on the straight lines between these chromaticity points can be reproduced, the outputs of the blue light source and the green light source can be changed to produce all white lights of incandescent lamp color, warm white, white, neutral white, and daylight. Thus, the white light source system of the present embodiment can alter the hue without an increase in its size.

The fiber light source of the present embodiment may include a control circuit that controls a solid-state light source to change the intensity of blue light and the intensity of green light. The control circuit controls a solid-state light source to change synthesized light of green light and blue light passing through the wavelength convertor and second light and third light emitted from the wavelength convertor from one selected from the group consisting of daylight, neutral white, white, warm white, and incandescent lamp color to another selected from the group. Thus, synthesized light emitted from the fiber light source is changed from one white (for example, daylight) to another white (for example, warm white).

Figure 39:
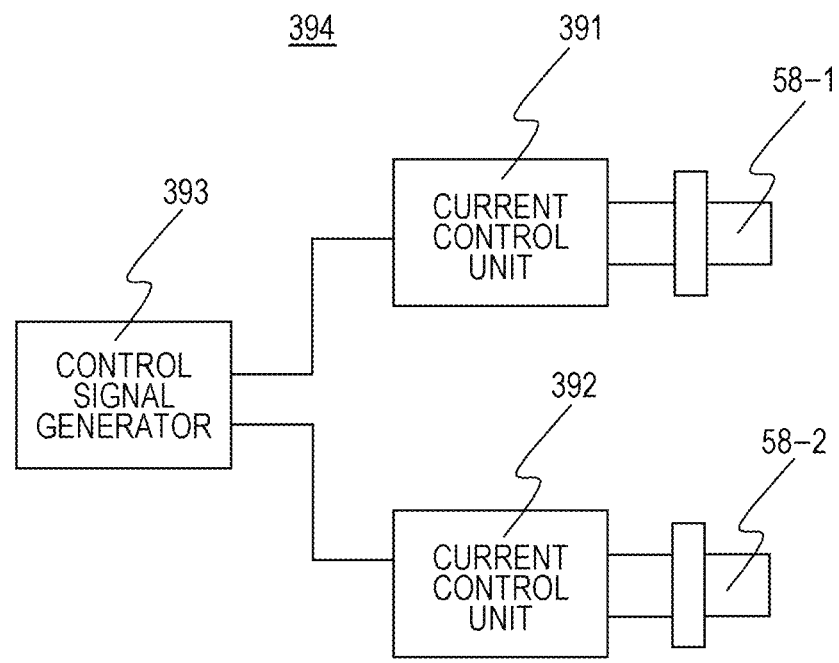
FIG. 39 is a block diagram of an example of a light source drive unit.

FIG. 39 is a block diagram of an example of a light source drive unit of the present embodiment. A light source drive unit 394 drives a light source to alter the hue of white light as described above. The light source drive unit 394 can be applied to any of the embodiments described above. The light source drive unit 394 includes the LD device 58-1, which is a blue light source, the LD device 58-2, which is a green light source, current control units 391 and 392, and a control signal generator 393. The current control unit 391 outputs a drive current to the LD device 58-1 and drives the LD device 58-1. The current control unit 392 outputs a drive current to the LD device 58-2 and drives the LD device 58-2. The control signal generator 393 outputs a control signal to the current control units 391 and 392 and independently controls a drive current output from the current control units 391 and 392. This can independently control the light outputs of the LD devices 58-1 and 58-2 and can alter the hue of white light to produce all white lights.

Figure 40:
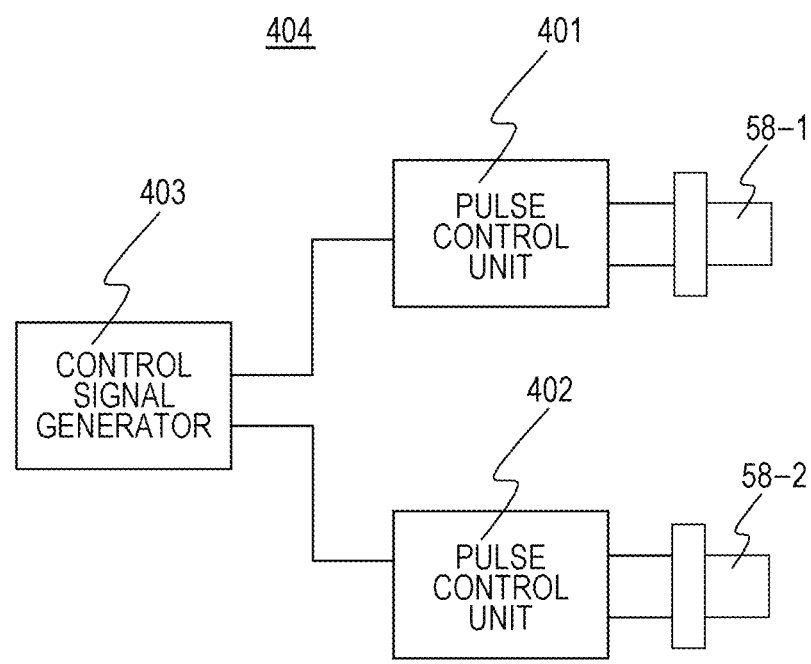
FIG. 40 is a block diagram of another example of the light source drive unit.

FIG. 40 is a block diagram of another example of the light source drive unit of the present embodiment. A light source drive unit 404 may drive a light source by another method to alter the hue of white light as described above. The light source drive unit 404 has the same structure as the light source drive unit 394 except that the current control units 391 and 392 and the control signal generator 393 are substituted by pulse control units 401 and 402 and a control signal generator 403. The pulse control unit 401 outputs a drive pulse to the LD device 58-1 and drives the LD device 58-1. The pulse control unit 402 outputs a drive pulse to the LD device 58-2 and drives the LD device 58-2. The control signal generator 403 outputs a control signal to the pulse control units 401 and 402 and independently controls the pulse width of a drive pulse output from the pulse control units 401 and 402. This can independently control the light outputs of the LD devices 58-1 and 58-2 and can alter the hue of white light to produce all white lights.

In the present disclosure, all or part of a unit, an apparatus, a member, or a portion, or all or part of a functional block illustrated in a figure may be implemented by one or more electronic circuits including a semiconductor device, a semiconductor integrated circuit (IC), or a large scale integration (LSI). LSI or IC may be integrated on one chip or a plurality of chips. For example, a functional block other than a memory device may be integrated on one chip. LSI or IC herein may also be a system LSI, a very large scale integration (VLSI), or an ultralarge scale integration (ULSI), depending on the degree of integration. A field programmable gate array (FPGA) programmed after the manufacture of LSI or a reconfigurable logic device, which allows reconfiguration of the junction relationship in LSI or setup of a circuit block in LSI, can also be used for the same purpose.

Furthermore, the function or operation of all or part of a unit, an apparatus, a member, or a portion may be performed by software processing. In this case, software is stored on one or a plurality of nontemporary recording media, such as a ROM, an optical disk, or a hard disk drive. When the software runs on a processing unit (processor), the function specified by the software is performed by the processing unit (processor) and a peripheral device. A system or apparatus may include one or a plurality of nontemporary recording media on which software is stored, a processing unit (processor), and a required hardware device, for example, an interface.

At least two selected from the group consisting of embodiments, modified examples, and examples of the present disclosure may be appropriately combined.

A fiber light source of the present disclosure is suitable for illumination in high places as well as for general lighting apparatuses and can be used as a light source of a lighting apparatus for stadiums, expressways, tunnels, and bridges, for example. A fiber light source of the present disclosure can be used as a light source in endoscopic lighting apparatuses.

What is claimed is:
1. A fiber light source comprising:
   a solid-state light source;
   a wavelength convertor; and
   an optical fiber, wherein
      the solid-state light source is configured to emit first light, the first light including blue light with a peak wavelength in a range of 430 to 470 nm, inclusive, and green light with a peak wavelength in a range of 480 to 550 nm, inclusive,
      the wavelength convertor is disposed on a light output side or a light incident side of the optical fiber and contains a red phosphor,
      the red phosphor includes Ce as a luminescent center, and is configured to be excited by at least part of the green light to emit second light,
      the second light has a spectrum with a maximum peak wavelength in a range of 600 to 700 nm, inclusive, and
      the red phosphor contains a nitride or an oxynitride as a host material.

2. The fiber light source according to claim 1, wherein the peak wavelength of the green light is in a range of 510 to 540 nm, inclusive.

3. The fiber light source according to claim 1, wherein
the wavelength convertor includes a first phosphor layer and a second phosphor layer,
the first phosphor layer contains a first phosphor, the first phosphor being the red phosphor, and
the second phosphor layer contains a second phosphor, the second phosphor being a phosphor different from the first phosphor.

4. The fiber light source according to claim 3, wherein
an excitation efficiency of the red phosphor is lower for the blue light than for the green light,
the second phosphor is configured to be excited by at least part of the blue light, and
the first phosphor layer is disposed closer to a light incident side of the wavelength convertor than the second phosphor layer.

5. The fiber light source according to claim 3, wherein the second phosphor is at least one selected from the group consisting of a yellow phosphor and a green phosphor.

6. The fiber light source according to claim 1, wherein the solid-state light source includes a GaN semiconductor laser.

7. The fiber light source according to claim 6, wherein
the GaN semiconductor laser is configured to emit the blue light, and
the solid-state light source further includes a YAG:Nd solid-state laser that is configured to emit the green light and that includes a second harmonic generator.

8. The fiber light source according to claim 1, wherein each of all phosphors in the wavelength convertor has a 1/e afterglow value of not more than 100 ns.

9. The fiber light source according to claim 1, wherein the red phosphor contains a host material, the host material containing Y or a lanthanoid element other than Ce.

10. A fiber light source comprising:
a solid-state light source;
a wavelength convertor; and
an optical fiber, wherein
the solid-state light source is configured to emit first light, the first light including blue light with a peak wavelength in a range of 430 to 470 nm, inclusive, and green light with a peak wavelength in a range of 480 to 550 nm, inclusive,
the wavelength convertor is disposed on a light output side or a light incident side of the optical fiber and contains a red phosphor,
the red phosphor includes Ce as a luminescent center, and is configured to be excited by at least part of the green light to emit second light,
the second light has a spectrum with a maximum peak wavelength in a range of 600 to 700 nm, inclusive, and
the red phosphor contains an oxide as a host material.

11. The fiber light source according to claim 1, wherein the red phosphor contains a host material having a tetragonal crystal structure.

12. The fiber light source according to claim 1, wherein the red phosphor contains a crystal phase having a chemical composition $Ce_xM_{3-x-y}\beta_{6\gamma 11-z}$,
wherein M denotes one or two or more elements selected from the group consisting of Sc, Y, La, Pr, Nd, Sm, Eu, Gd, Tb, Dy, Ho, Er, Tm, Yb, and Lu,
β includes Si in an amount of not less than 50% by mole of a total amount of Si,
γ includes N in an amount of not less than 80% by mole of a total amount of N, and
x, y and z satisfy
$0<x\leq 0.6$,
$0\leq y\leq 1.0$, and
$0\leq z\leq 1.0$.

13. The fiber light source according to claim 12, wherein the red phosphor contains a crystal phase having a chemical composition of $Ce_xM_{3-x}Si_{6-q}Al_qN_{11-z}$, where q satisfies $0\leq q\leq 2.0$.

14. The fiber light source according to claim 13, wherein the red phosphor contains a crystal phase having a chemical composition of $Ce_xLa_{3-x}Si_{6-q}Al_qN_{11-z}$, where q satisfies $0<q\leq 2.0$.

15. The fiber light source according to claim 13, wherein the red phosphor contains a crystal phase having a chemical composition of $Ce_xY_pLa_{3-x-p}Si_6N_{11}$, where p and x satisfy $(1.5-x)\leq p\leq (3-x)$.

16. The fiber light source according to claim 1, wherein the wavelength convertor further contains a phosphor containing a garnet crystal including Ce as a luminescent center.

17. The fiber light source according to claim 1, wherein
the solid-state light source includes a blue laser that is configured to emit the blue light and a green laser that is configured to emit the green light, and
the fiber light source further includes a dichroic mirror by which the blue light and the green light are coaxially multiplexed to be incident on the optical fiber.

18. The fiber light source according to claim 1, further comprising:
a coupler lens that is disposed on the light incident side of the optical fiber and enables light to be incident on the optical fiber.

19. The fiber light source according to claim 1, wherein the wavelength convertor is disposed on the light output side of the optical fiber and receives the first light from the solid-state light source through the optical fiber.

20. The fiber light source according to claim 19, further comprising:
a condenser lens disposed on an optical path between a light output end of the optical fiber and the wavelength convertor, and
an objective lens disposed on a light output side of the wavelength convertor.

21. The fiber light source according to claim 1, wherein the wavelength convertor is disposed on the light incident side of the optical fiber, the fiber light source further comprising:
a condenser lens disposed on an optical path between the wavelength convertor and a light incident end of the optical fiber, and
an objective lens disposed on the light output side of the optical fiber.

22. An endoscope comprising:
a fiber light source; and
an image sensor for outputting an electric signal depending on an amount of light received, the light being emitted from the fiber light source and reflected by an object, wherein
the fiber light source includes a solid-state light source, a wavelength convertor, and an optical fiber,
the solid-state light source is configured to emit first light, the first light including blue light with a peak wavelength in a range of 430 to 470 nm, inclusive, and green light with a peak wavelength in a range of 480 to 550 nm, inclusive, the wavelength convertor is disposed on a light output side or a light incident side of the optical fiber and contains a red phosphor, the red phosphor includes Ce as a luminescent center, and is configured to be excited by at least part of the green light to emit second light, the second light has a spectrum with a maximum peak wavelength in a range of 600 to 700 nm, inclusive, and the red phosphor contains a nitride or an oxynitride as a host material.

23. The fiber light source according to claim 1, wherein the wavelength convertor further contains a phosphor that is configured to be excited by at least part of the blue light to emit third light, the third light has a spectrum with a peak wavelength in a range of 500 to 600 nm, inclusive, first synthesized light of the green light passing through the wavelength convertor and the second light emitted from the wavelength convertor has a chromaticity point satisfying $0.48 < CIEx < 0.60$ and $0.40 < CIEy < 0.49$, and second synthesized light of the blue light passing through the wavelength convertor and the third light emitted from the wavelength convertor has a chromaticity point satisfying $0.15 < CIEx < 0.30$ and $0.20 < CIEy < 0.36$.

24. The fiber light source according to claim 23, further comprising a controller configured to control the solid-state light source to change an intensity of the blue light and an intensity of the green light to change color of third synthesized light of the first synthesized light and the second synthesized light from one selected from the group consisting of daylight, neutral white, white, warm white, and incandescent lamp color to another selected from the group consisting of daylight, neutral white, white, warm white, and incandescent lamp color.

* * * * *